United States Patent [19]
Fukuda

[11] Patent Number: 6,111,089
[45] Date of Patent: Aug. 29, 2000

[54] TROPHININ, TROPHININ-ASSISTING PROTEINS AND METHODS TO INHIBIT IMPLANTATION

[75] Inventor: Michiko N. Fukuda, San Diego, Calif.

[73] Assignee: The Burnham Institute, La Jolla, Calif.

[21] Appl. No.: 08/808,599

[22] Filed: Feb. 28, 1997

Related U.S. Application Data

[63] Continuation-in-part of application No. 08/439,818, May 12, 1995, Pat. No. 5,654,145, which is a continuation-in-part of application No. 08/317,522, Oct. 4, 1994, Pat. No. 5,599,918.

[51] Int. Cl.[7] ..................................................... C12N 15/12
[52] U.S. Cl. .................... 536/23.5; 536/24.3; 536/24.31; 435/69.1; 435/320.1; 435/325; 435/252.3; 435/254.11; 530/350
[58] Field of Search .................................. 536/23.5, 24.3, 536/24.31; 530/350; 435/69.1, 320.1, 325, 252.3, 254.11

[56] References Cited

U.S. PATENT DOCUMENTS 5,599,918  2/1997  Fukuda ................................... 536/23.1

FOREIGN PATENT DOCUMENTS

WO 96/10414  4/1996  WIPO .

OTHER PUBLICATIONS

Hillier et al., the WashU–Merck EST project, locus T74465, Mar. 1995.

Ausubel et al., Short protocols in Molecular Biology, Wiley & sons, Chapter 6, 1989.

Fukuda et al., "Trophinin and tastin, a novel cell adhesion molecule complex with potential involvement in embryo implantation." *Genes & Devel.*, 9:1199–1210 (1995).

Dirnhofer and Berger, "Vaccination for Birth Control." *Int. Arch Allergy Immunol.*, 108:350–354 (1995).

Kemp and Pearson, "Protein kinase recognition sequence motifs." *Trends Biochem. Sci.*, 15:342–346 (1990).

Gonzalez et al., "Identification of Substrate Recognition Determinants for Human ERK1 and ERK2 Protein Kinases." *J. Biol. Chem.*, 266(33):22159–22163 (1991).

Adams et al., "Sequence identification of 2,375 human brain genes," *Nature*, 355:632–634 (1992).

Stewart and Denell, "Mutations in the Drosophila Gene Encoding Ribosomal Protein S6 Cause Tissue Overgrowth." *Mol. Cell Biol.*, 13(4):2524–2535 (1993).

Minoru Fukuda, "Lysosomal Membrane Glycoproteins." *J. Biol. Chem.*, 266(32):21327–21330 (1991).

Pullman and Bodmer, "Cloning and characterization of a gene that regulates cell adhesion." *Nature*, 356:529–532 (1992).

*Primary Examiner*—Lorraine Spector
*Assistant Examiner*—Eliane Lazar-Wesley
*Attorney, Agent, or Firm*—Campbell & Flores LLP

[57] ABSTRACT

The present invention provides a method to prevent pregnancy in an individual by administering a trophinin vaccine, which can elicit an immune response in the individual administered the vaccine. The method utilizes mammalian trophinin and peptides derived thereof from human or mice. The method also utilizes a nucleic acid molecule encoding trophinin as the trophinin vaccine, which is expressed in the individual administered the vaccine. The nucleic acid molecule can further encode a trophinin-assisting protein that can be co-expressed with trophinin in the individual administered the vaccine. The invention also provides a method to prevent adhesion between a trophoblast cell and a uterine epithelial cell by administering a trophinin vaccine or peptides thereof. The invention further provides an adjuvant or a carrier protein to enhance the immune response to the trophinin vaccine. The invention also provides mammalian trophinin active fragments, antibodies to the fragments, nucleic acid molecules encoding the fragments and nucleic acid probes that can hybridize to the nucleic acid molecules.

18 Claims, 4 Drawing Sheets

```
  1 MDINCLTREELGDDAQAWSR      215 FSGGANSS              432 FGGSPSTNTG
 21 FSFEIEPRAQENADPTTNVL      223 FSGTPSTSAP            442 FGGTLSTSVS
 41 FNQGATTRNS                233 FCNAASIS              452 FGASSSTSSD
 51 FSDGAGIS                  241 FGGAPSTSTS            462 FGGTLSTSVS
 59 FGGITNPSGG                251 FSTASIS               472 FGGSSGANAG
 69 FGGISNPSGG                258 FGGAPSTSTSLSTASIS     482 FGGTLNSSTS
 79 FGGISNPSGG                275 FGGAPSTSTS            492 FGGAISTSTG
 89 FGGISNPSGG                285 FSTASIS               502 FGSALNNSAN
 99 FGGISNPSGG                292 FGGAPSTSTSLSTASIS     512 FGGAISTS
109 FGGISNPSGG                309 FGGAPSINSSSGGSSVS     520 FSGVLNSSAS
119 FGGISNPSGG                326 FGGAPTTSTS            530 FGGAINTSAG
129 FGGISNPSGG                336 FSGGPCIS              540 FGSTLNSSAS
139 FGGISNPSGG                344 FGGAPCTTASISGGASSG    550 FGSALSTSAS
149 FGGISNPSGG                362 FGSTLCSTNPG           560 FGGVLNGRAG
159 FGGISNPSGG                373 FSALSTNTS             570 FGGALNTNAT
169 FGGISNPSGG                382 FGSAPTTSTV            580 FGGVLNGSAG
179 FGGRNSIT                  392 FSGAVSTTTG            590 FGGAMNTNAT
187 FGSVPNTSAN                402 FGGTLSTSVC            600 FGGALNSNAG
197 FSSAPSIS                  412 FGSSPYSGAG            610 FGGAISTSTN
205 FGDTPNTSTS                422 FGGTLSTSIS            620 FGGALNNSAG

FIG. 1A                     FIG. 1B                    FIG. 1C
```

| | | | | |
|---|---|---|---|---|
| 630 | FGGAMNTSAS | 824 | FGNGLSTSAG | 1022 FSGGPSTGAG |
| 640 | FGGVLNNSAG | 834 | FGNGLGTSAG | 1032 FCSGPSTGG |
| 650 | FGGAINTSAN | 844 | FDSSLGTSTG | 1041 FGGGPSTGPG |
| 660 | FGGALTNSAG | 854 | FGGSLGPSAS | 1051 FGGPSTGPG |
| 670 | FGGAISTSAS | 864 | FNGGLGTSTG | 1060 FGGPSTGGG |
| 680 | FGGALNNSAG | 874 | FGGGLGTSTD | 1069 FGGPNTGGG |
| 690 | FGGAISTSAS | 884 | FSGGLNHNAD | 1078 FGGPSTGGG |
| 700 | FGGALNNSAG | 894 | FNGGLGNSAG | 1087 FGGPSTGGG |
| 710 | FGGAISTNAS | 904 | FNGGLNTNTD | 1096 FGGPSTGGG |
| 720 | FGGAISNSPD | 914 | FGGELGTSAG | 1105 FGGPSTAAG |
| 730 | FGGAFSTSVG | 924 | FGDGLGSSTS | 1114 FGSGLSTSTG |
| 740 | FGGTLNTTD | 934 | FGAGLVTSDG | 1124 FGGGLNTSAG |
| 749 | FGSNHSNSIS | 944 | FAGNLGTNTG | 1134 FSGGPPSTGTG |
| 759 | FGSAPTTSVS | 954 | FGGTLGTGAG | 1145 FGGGASSHGGCG |
| 769 | FGGSHSTNLC | 964 | FSVSLNNGNG | 1157 FPYG |
| 779 | FGGAPSTSLC | 974 | FGNGPNAS | |
| 789 | FGSASNTNLC | 982 | FNRGLNTIIG | |
| 799 | FGGSNSTNC | 992 | FGSGSNTSNG | |
| 808 | FSGATSAN | 1002 | FTGEPNTGSS | |
| 816 | FNEGHSIS | 1012 | FSNGPSSIVG | |

```
M  MDINCLTREELGDDAQAWSRFSFEIEPRAQENADPTTNVLFNQGATTRNSFSDG  54
     ||| |||||||||||:|||||||||||||||| :|||  :|||  ::||  ||
H  MDIDCLTREELGDDSQAWSRFSFEIEARAQENADASTNVFSRGASTRAGFSDR  54
```

FIG. 2A

```
M  NGFGNGPNASFNRGLNTIIGFGSGSNTSNGFTGEPNTGSSFSNGPSSIVGFSGGPSTGAG  1031
      ||| |||||  ||| |||||||||||||| |||| : ||  |  |||||||||||||||||| :|
H  DGFGSRPNASFDRGLSTIIGFGSGSNTSTGFTGEPSTSTGFSSGPSSIVGFSSGGPSTGVG  694

M  FCSGPSTGGFGGGPSTGPGFGG  1053
   |||||||||   || |||||  ||||
H  FCSGPSTSGFSGGPSTGAGFGG  716
```

FIG. 2B

SEQUENCE LISTING (1) GENERAL INFORMATION:

(iii) NUMBER OF SEQUENCES: 41

(2) INFORMATION FOR SEQ ID NO:1:

(i) SEQUENCE CHARACTERISTICS:
       (A) LENGTH: 2524 base pairs
       (B) TYPE: nucleic acid
       (C) STRANDEDNESS: single
       (D) TOPOLOGY: linear (ix) FEATURE:
       (A) NAME/KEY: CDS
       (B) LOCATION: 28..2275

(xi) SEQUENCE DESCRIPTION: SEQ ID NO:1:

```
GTGGCTGGGC CCTGGAATTG GGATGAC ATG GAT ATC GAC TGC CTA ACA AGG                51
                              Met Asp Ile Asp Cys Leu Thr Arg
                                1               5

GAA GAG TTA GGC GAT GAT TCT CAG GCC TGG AGC AGA TTT TCA TTT GAA              99
Glu Glu Leu Gly Asp Asp Ser Gln Ala Trp Ser Arg Phe Ser Phe Glu
         10                  15                  20

ATT GAG GCC AGA GCC CAA GAA AAT GCA GAT GCC AGC ACC AAC GTC AAC             147
Ile Glu Ala Arg Ala Gln Glu Asn Ala Asp Ala Ser Thr Asn Val Asn
 25                  30                  35                  40

TTC AGC AGA GGA GCT AGT ACC AGG GCT GGC TTC AGC GAT CGT GCT AGT             195
Phe Ser Arg Gly Ala Ser Thr Arg Ala Gly Phe Ser Asp Arg Ala Ser
                 45                  50                  55

ATT AGC TTC AAT GGT GCA CCC AGC TCC AGT GGT GGC TTC AGT GGT GGA             243
Ile Ser Phe Asn Gly Ala Pro Ser Ser Ser Gly Gly Phe Ser Gly Gly
             60                  65                  70

CCT GGC ATT ACC TTT GGT GTT GCA CCC AGC ACC AGT GCC AGC TTC AGC             291
Pro Gly Ile Thr Phe Gly Val Ala Pro Ser Thr Ser Ala Ser Phe Ser
         75                  80                  85

AAT ACA GCC AGC ATT AGC TTT GGT GGT ACA CTG AGC ACT AGC TCC AGC             339
Asn Thr Ala Ser Ile Ser Phe Gly Gly Thr Leu Ser Thr Ser Ser Ser
 90                  95                 100

TTC AGC AGC GCA GCC AGC ATT AGC TTT GGT TGT GCA CAC AGC ACC AGC             387
Phe Ser Ser Ala Ala Ser Ile Ser Phe Gly Cys Ala His Ser Thr Ser
105                 110                 115                 120

ACT AGT TTC AGC AGT GAA GCC AGC ATT AGC TTT GGT GGC ATG CCT TGT             435
Thr Ser Phe Ser Ser Glu Ala Ser Ile Ser Phe Gly Gly Met Pro Cys
                125                 130                 135

ACC AGT GCC AGC TTT AGT GGT GGA GTC AGC TCT AGT TTT AGT GGC CCA             483
Thr Ser Ala Ser Phe Ser Gly Gly Val Ser Ser Ser Phe Ser Gly Pro
            140                 145                 150

CTC AGC ACC AGT GCC ACT TTC AGT GGT GGA GCC AGC TCT GGC TTT GGA             531
Leu Ser Thr Ser Ala Thr Phe Ser Gly Gly Ala Ser Ser Gly Phe Gly
        155                 160                 165

GGC ACA CTC AGC ACC ACG GCT GGC TTT AGT GGT GTA CTC AGC ACT AGC             579
Gly Thr Leu Ser Thr Thr Ala Gly Phe Ser Gly Val Leu Ser Thr Ser
    170                 175                 180

ACC AGC TTT GGC AGT GCA CCC ACA ACG AGC ACA GTC TTC AGT AGT GCG             627
Thr Ser Phe Gly Ser Ala Pro Thr Thr Ser Thr Val Phe Ser Ser Ala
185                 190                 195                 200

CTT AGC ACC AGC ACT GGC TTT GGA GGC ATA CTC AGC ACC AGT GTC TGT             675
Leu Ser Thr Ser Thr Gly Phe Gly Gly Ile Leu Ser Thr Ser Val Cys
                205                 210                 215

TTT GGT GGC TCT CCC AGC TCC AGT GGT AGC TTT GGT GGT ACA CTC AGT             723
```

```
Phe Gly Gly Ser Pro Ser Ser Gly Ser Phe Gly Gly Thr Leu Ser
            220                 225                 230

ACC AGT ATC TGC TTC GGT GGC TCT CCC TGC ACC AGC ACT GGC TTT GGA          771
Thr Ser Ile Cys Phe Gly Gly Ser Pro Cys Thr Ser Thr Gly Phe Gly
        235                 240                 245

GGC ACA CTT AGC ACC AGT GTC TCC TTT GGT GGC TCT TCC AGC ACC AGT          819
Gly Thr Leu Ser Thr Ser Val Ser Phe Gly Gly Ser Ser Ser Thr Ser
250                 255                 260

GCC AAT TTT GGT GGT ACA CTA AGT ACC AGC ATC TGC TTT GAT GGC TCT          867
Ala Asn Phe Gly Gly Thr Leu Ser Thr Ser Ile Cys Phe Asp Gly Ser
265                 270                 275                 280

CCC AGC ACT GGT GCT GGC TTT GGT GGT GCT CTC AAC ACC AGT GCC AGC          915
Pro Ser Thr Gly Ala Gly Phe Gly Gly Ala Leu Asn Thr Ser Ala Ser
                285                 290                 295

TTT GGC AGT GTG CTC AAC ACC AGT ACT GGT TTT GGT GGT GCT ATG AGC          963
Phe Gly Ser Val Leu Asn Thr Ser Thr Gly Phe Gly Gly Ala Met Ser
            300                 305                 310

ACC AGT GCT GAC TTT GGC GGT ACA CTA AGC ACC AGT GTC TGC TTT GGT         1011
Thr Ser Ala Asp Phe Gly Gly Thr Leu Ser Thr Ser Val Cys Phe Gly
        315                 320                 325

GGC TCT CCT GGC ACC AGT GTC AGC TTT GGC AGT GCA CTC AAC ACC AAT         1059
Gly Ser Pro Gly Thr Ser Val Ser Phe Gly Ser Ala Leu Asn Thr Asn
330                 335                 340

GCT GGT TAT GGT GGT GCT GTC AGC ACC AAC ACT GAC TTT GGT GGT ACA         1107
Ala Gly Tyr Gly Gly Ala Val Ser Thr Asn Thr Asp Phe Gly Gly Thr
345                 350                 355                 360

CTA AGC ACC AGC GTC TGT TTT GGT GGC TCT CCC AGC ACC AGT GCT GGC         1155
Leu Ser Thr Ser Val Cys Phe Gly Gly Ser Pro Ser Thr Ser Ala Gly
                365                 370                 375

TTT GGT GGT GCA CTC AAC ACC AAT GCC AGC TTT GGC TGT GCC GTC AGC         1203
Phe Gly Gly Ala Leu Asn Thr Asn Ala Ser Phe Gly Cys Ala Val Ser
            380                 385                 390

ACC AGT GCC AGC TTC AGT GGT GCT GTC AGC ACC AGT GCT TGC TTC AGT         1251
Thr Ser Ala Ser Phe Ser Gly Ala Val Ser Thr Ser Ala Cys Phe Ser
        395                 400                 405

GGT GCA CCA ATC ACC AAC CCT GGC TTT GGC GGT GCA TTT AGC ACC AGT         1299
Gly Ala Pro Ile Thr Asn Pro Gly Phe Gly Gly Ala Phe Ser Thr Ser
410                 415                 420

GCT GGC TTC GGT GGT GCA CTT AGT ACC GCT GCT GAC TTC GGT GGT ACT         1347
Ala Gly Phe Gly Gly Ala Leu Ser Thr Ala Ala Asp Phe Gly Gly Thr
425                 430                 435                 440

CCC AGC AAC AGC ATT GGC TTT GGT GCT GCT CCC AGC ACC AGT GTC AGC         1395
Pro Ser Asn Ser Ile Gly Phe Gly Ala Ala Pro Ser Thr Ser Val Ser
                445                 450                 455

TTT GGT GGT GCT CAT GGC ACC AGC CTC TGT TTT GGT GGA GCT CCC AGC         1443
Phe Gly Gly Ala His Gly Thr Ser Leu Cys Phe Gly Gly Ala Pro Ser
            460                 465                 470

ACC AGC CTC TGC TTT GGC AGT GCA TCT AAT ACT AAC CTA TGC TTT GGT         1491
Thr Ser Leu Cys Phe Gly Ser Ala Ser Asn Thr Asn Leu Cys Phe Gly
        475                 480                 485

GGC CCT CCT AGC ACC AGT GCC TGC TTT AGT GGT GCT ACC AGC CCT AGT         1539
Gly Pro Pro Ser Thr Ser Ala Cys Phe Ser Gly Ala Thr Ser Pro Ser
490                 495                 500

TTT TGT GAT GGA CCC AGC ACC AGT ACC GGT TTC AGC TTT GGC AAT GGG         1587
Phe Cys Asp Gly Pro Ser Thr Ser Thr Gly Phe Ser Phe Gly Asn Gly
505                 510                 515                 520

TTA AGC ACC AAT GCT GGA TTT GGT GGT GGA CTG AAC ACC AGT GCT GGC         1635
Leu Ser Thr Asn Ala Gly Phe Gly Gly Gly Leu Asn Thr Ser Ala Gly
                525                 530                 535
```

```
TTT GGT GGT GGC CTA GGC ACC AGT GCT GGC TTC AGT GGT GGC CTA AGC        1683
Phe Gly Gly Gly Leu Gly Thr Ser Ala Gly Phe Ser Gly Gly Leu Ser
            540                 545                 550

ACA AGT TCT GGC TTT GAT GGT GGG CTA GGT ACC AGC GCT GGC TTC GGT        1731
Thr Ser Ser Gly Phe Asp Gly Gly Leu Gly Thr Ser Ala Gly Phe Gly
                555                 560                 565

GGA GGA CCA GGC ACC AGC ACT GGT TTT GGT GGT GGA CTG GGC ACC AGT        1779
Gly Gly Pro Gly Thr Ser Thr Gly Phe Gly Gly Gly Leu Gly Thr Ser
    570                 575                 580

GCT GGC TTC AGT GGC GGA CTG GGC ACC AGT GCT GGC TTT GGT GGT GGA        1827
Ala Gly Phe Ser Gly Gly Leu Gly Thr Ser Ala Gly Phe Gly Gly Gly
585                 590                 595                 600

CTG GTC ACT AGT GAT GGC TTT GGT GGT GGA CTG GGC ACC AAT GCT AGT        1875
Leu Val Thr Ser Asp Gly Phe Gly Gly Gly Leu Gly Thr Asn Ala Ser
                605                 610                 615

TTC GGC AGC ACA CTT GGC ACC AGT GCT GGC TTT AGT GGT GGC CTC AGC        1923
Phe Gly Ser Thr Leu Gly Thr Ser Ala Gly Phe Ser Gly Gly Leu Ser
                620                 625                 630

ACC AGC GAT GGC TTT GGC AGT AGG CCT AAT GCC AGC TTC GAC AGA GGA        1971
Thr Ser Asp Gly Phe Gly Ser Arg Pro Asn Ala Ser Phe Asp Arg Gly
    635                 640                 645

CTG AGT ACC ATC ATT GGC TTT GGC AGT GGT TCC AAC ACC AGC ACT GGC        2019
Leu Ser Thr Ile Ile Gly Phe Gly Ser Gly Ser Asn Thr Ser Thr Gly
650                 655                 660

TTT ACT GGC GAA CCC AGC ACC AGC ACG GGC TTC AGT AGT GGA CCC AGT        2067
Phe Thr Gly Glu Pro Ser Thr Ser Thr Gly Phe Ser Ser Gly Pro Ser
665                 670                 675                 680

TCT ATT GTT GGC TTC AGC GGT GGA CCA AGC ACT GGT GTT GGC TTC TGC        2115
Ser Ile Val Gly Phe Ser Gly Gly Pro Ser Thr Gly Val Gly Phe Cys
                685                 690                 695

AGT GGA CCA AGC ACC AGT GGC TTC AGC GGT GGA CCC AGC ACA GGA GCT        2163
Ser Gly Pro Ser Thr Ser Gly Phe Ser Gly Gly Pro Ser Thr Gly Ala
                700                 705                 710

GGC TTC GGC GGT GGA CCA AAC ACT GGT GCT GGC TTT GGT GGT GGA CCG        2211
Gly Phe Gly Gly Gly Pro Asn Thr Gly Ala Gly Phe Gly Gly Gly Pro
            715                 720                 725

AGC ACC AGT GCT GGC TTT GGC AGT GGA GCC GCC AGT CTT GGT GCC TGT        2259
Ser Thr Ser Ala Gly Phe Gly Ser Gly Ala Ala Ser Leu Gly Ala Cys
            730                 735                 740

GGC TTC TCG TAT GGC T AGTGAGGTTT CAGATACCGC TAATAAATTG CAGTAGTCCT      2315
Gly Phe Ser Tyr Gly
745

TCCCATGGAG CCAAAGTACC TTGGATCTTT GTCCACACAG CAGTCAAGGC AGTTATGGCC      2375

CATCAGCTGA GGGTGTCATG TGATGGAAAA ATCTGTTTGC TGTTCCTGCT TTATTGTTTG      2435

CTTTCTGTGT GCTGTCATAT TTTGGTATCA GAGTTACATT AAATTTGCAA AATGAAAAAA      2495

AAAAAAAAAA AAAAAAAAAA AAAAAAAA                                        2524

(2) INFORMATION FOR SEQ ID NO:2:

(i) SEQUENCE CHARACTERISTICS:
        (A) LENGTH: 749 amino acids
        (B) TYPE: amino acid
        (D) TOPOLOGY: linear (ii) MOLECULE TYPE: protein (xi) SEQUENCE DESCRIPTION: SEQ ID NO:2:

Met Asp Ile Asp Cys Leu Thr Arg Glu Glu Leu Gly Asp Asp Ser Gln
  1               5                  10                  15
```

-continued

```
Ala Trp Ser Arg Phe Ser Phe Glu Ile Glu Ala Arg Ala Gln Glu Asn
         20                  25                  30

Ala Asp Ala Ser Thr Asn Val Asn Phe Ser Arg Gly Ala Ser Thr Arg
         35                  40                  45

Ala Gly Phe Ser Asp Arg Ala Ser Ile Ser Phe Asn Gly Ala Pro Ser
         50                  55                  60

Ser Ser Gly Gly Phe Ser Gly Gly Pro Gly Ile Thr Phe Gly Val Ala
 65                  70                  75                  80

Pro Ser Thr Ser Ala Ser Phe Ser Asn Thr Ala Ser Ile Ser Phe Gly
                     85                  90                  95

Gly Thr Leu Ser Thr Ser Ser Phe Ser Ser Ala Ala Ser Ile Ser
                100                 105                 110

Phe Gly Cys Ala His Ser Thr Ser Thr Ser Phe Ser Ser Glu Ala Ser
            115                 120                 125

Ile Ser Phe Gly Gly Met Pro Cys Thr Ser Ala Ser Phe Ser Gly Gly
        130                 135                 140

Val Ser Ser Ser Phe Ser Gly Pro Leu Ser Thr Ser Ala Thr Phe Ser
145                 150                 155                 160

Gly Gly Ala Ser Ser Gly Phe Gly Gly Thr Leu Ser Thr Thr Ala Gly
                165                 170                 175

Phe Ser Gly Val Leu Ser Thr Ser Thr Ser Phe Gly Ser Ala Pro Thr
            180                 185                 190

Thr Ser Thr Val Phe Ser Ser Ala Leu Ser Thr Ser Thr Gly Phe Gly
        195                 200                 205

Gly Ile Leu Ser Thr Ser Val Cys Phe Gly Gly Ser Pro Ser Ser Ser
    210                 215                 220

Gly Ser Phe Gly Gly Thr Leu Ser Thr Ser Ile Cys Phe Gly Gly Ser
225                 230                 235                 240

Pro Cys Thr Ser Thr Gly Phe Gly Gly Thr Leu Ser Thr Ser Val Ser
                245                 250                 255

Phe Gly Gly Ser Ser Ser Thr Ser Ala Asn Phe Gly Gly Thr Leu Ser
            260                 265                 270

Thr Ser Ile Cys Phe Asp Gly Ser Pro Ser Thr Gly Ala Gly Phe Gly
        275                 280                 285

Gly Ala Leu Asn Thr Ser Ala Ser Phe Gly Ser Val Leu Asn Thr Ser
    290                 295                 300

Thr Gly Phe Gly Gly Ala Met Ser Thr Ser Ala Asp Phe Gly Gly Thr
305                 310                 315                 320

Leu Ser Thr Ser Val Cys Phe Gly Gly Ser Pro Gly Thr Ser Val Ser
                325                 330                 335

Phe Gly Ser Ala Leu Asn Thr Asn Ala Gly Tyr Gly Gly Ala Val Ser
            340                 345                 350

Thr Asn Thr Asp Phe Gly Gly Thr Leu Ser Thr Ser Val Cys Phe Gly
        355                 360                 365

Gly Ser Pro Ser Thr Ser Ala Gly Phe Gly Gly Ala Leu Asn Thr Asn
    370                 375                 380

Ala Ser Phe Gly Cys Ala Val Ser Thr Ser Ala Ser Phe Ser Gly Ala
385                 390                 395                 400

Val Ser Thr Ser Ala Cys Phe Ser Gly Ala Pro Ile Thr Asn Pro Gly
                405                 410                 415

Phe Gly Gly Ala Phe Ser Thr Ser Ala Gly Phe Gly Gly Ala Leu Ser
            420                 425                 430

Thr Ala Ala Asp Phe Gly Gly Thr Pro Ser Asn Ser Ile Gly Phe Gly
```

-continued

```
              435                 440                 445
Ala Ala Pro Ser Thr Ser Val Ser Phe Gly Gly Ala His Gly Thr Ser
    450                 455                 460
Leu Cys Phe Gly Gly Ala Pro Ser Thr Ser Leu Cys Phe Gly Ser Ala
465                 470                 475                 480
Ser Asn Thr Asn Leu Cys Phe Gly Gly Pro Pro Ser Thr Ser Ala Cys
                485                 490                 495
Phe Ser Gly Ala Thr Ser Pro Ser Phe Cys Asp Gly Pro Ser Thr Ser
            500                 505                 510
Thr Gly Phe Ser Phe Gly Asn Gly Leu Ser Thr Asn Ala Gly Phe Gly
            515                 520                 525
Gly Gly Leu Asn Thr Ser Ala Gly Phe Gly Gly Leu Gly Thr Ser
    530                 535                 540
Ala Gly Phe Ser Gly Gly Leu Ser Thr Ser Ser Gly Phe Asp Gly Gly
545                 550                 555                 560
Leu Gly Thr Ser Ala Gly Phe Gly Gly Pro Gly Thr Ser Thr Gly
                565                 570                 575
Phe Gly Gly Gly Leu Gly Thr Ser Ala Gly Phe Ser Gly Gly Leu Gly
            580                 585                 590
Thr Ser Ala Gly Phe Gly Gly Leu Val Thr Ser Asp Gly Phe Gly
    595                 600                 605
Gly Gly Leu Gly Thr Asn Ala Ser Phe Gly Ser Thr Leu Gly Thr Ser
    610                 615                 620
Ala Gly Phe Ser Gly Gly Leu Ser Thr Ser Asp Gly Phe Gly Ser Arg
625                 630                 635                 640
Pro Asn Ala Ser Phe Asp Arg Gly Leu Ser Thr Ile Ile Gly Phe Gly
                645                 650                 655
Ser Gly Ser Asn Thr Ser Thr Gly Phe Thr Gly Glu Pro Ser Thr Ser
                660                 665                 670
Thr Gly Phe Ser Ser Gly Pro Ser Ser Ile Val Gly Phe Ser Gly Gly
            675                 680                 685
Pro Ser Thr Gly Val Gly Phe Cys Ser Gly Pro Ser Thr Ser Gly Phe
    690                 695                 700
Ser Gly Gly Pro Ser Thr Gly Ala Gly Phe Gly Gly Pro Asn Thr
705                 710                 715                 720
Gly Ala Gly Phe Gly Gly Gly Pro Ser Thr Ser Ala Gly Phe Gly Ser
                725                 730                 735
Gly Ala Ala Ser Leu Gly Ala Cys Gly Phe Ser Tyr Gly
                740                 745

(2) INFORMATION FOR SEQ ID NO:3:

(i) SEQUENCE CHARACTERISTICS:
        (A) LENGTH: 674 amino acids
        (B) TYPE: amino acid
        (D) TOPOLOGY: linear (xi) SEQUENCE DESCRIPTION: SEQ ID NO:3:

Phe Ser Gly Gly Pro Gly Ile Thr Phe Gly Val Ala Pro Ser Thr Ser
1               5                   10                  15
Ala Ser Phe Ser Asn Thr Ala Ser Ile Ser Phe Gly Gly Thr Leu Ser
                20                  25                  30
Thr Ser Ser Ser Phe Ser Ser Ala Ala Ser Ile Ser Phe Gly Cys Ala
        35                  40                  45
His Ser Thr Ser Thr Ser Phe Ser Ser Glu Ala Ser Ile Ser Phe Gly
```

```
              50                  55                  60
Gly Met Pro Cys Thr Ser Ala Ser Phe Ser Gly Val Ser Ser Ser
 65                  70                  75                  80

Phe Ser Gly Pro Leu Ser Thr Ser Ala Thr Phe Ser Gly Gly Ala Ser
                 85                  90                  95

Ser Gly Phe Gly Gly Thr Leu Ser Thr Thr Ala Gly Phe Ser Gly Val
                100                 105                 110

Leu Ser Thr Ser Thr Ser Phe Gly Ser Ala Pro Thr Thr Ser Thr Val
                115                 120                 125

Phe Ser Ser Ala Leu Ser Thr Ser Thr Gly Phe Gly Gly Ile Leu Ser
                130                 135                 140

Thr Ser Val Cys Phe Gly Gly Ser Pro Ser Ser Ser Gly Ser Phe Gly
145                 150                 155                 160

Gly Thr Leu Ser Thr Ser Ile Cys Phe Gly Gly Ser Pro Cys Thr Ser
                165                 170                 175

Thr Gly Phe Gly Gly Thr Leu Ser Thr Ser Val Ser Phe Gly Gly Ser
                180                 185                 190

Ser Ser Thr Ser Ala Asn Phe Gly Gly Thr Leu Ser Thr Ser Ile Cys
                195                 200                 205

Phe Asp Gly Ser Pro Ser Thr Gly Ala Gly Phe Gly Gly Ala Leu Asn
                210                 215                 220

Thr Ser Ala Ser Phe Gly Ser Val Leu Asn Thr Ser Thr Gly Phe Gly
225                 230                 235                 240

Gly Ala Met Ser Thr Ser Ala Asp Phe Gly Gly Thr Leu Ser Thr Ser
                245                 250                 255

Val Cys Phe Gly Gly Ser Pro Gly Thr Ser Val Ser Phe Gly Ser Ala
                260                 265                 270

Leu Asn Thr Asn Ala Gly Tyr Gly Gly Ala Val Ser Thr Asn Thr Asp
                275                 280                 285

Phe Gly Gly Thr Leu Ser Thr Ser Val Cys Phe Gly Gly Ser Pro Ser
                290                 295                 300

Thr Ser Ala Gly Phe Gly Gly Ala Leu Asn Thr Asn Ala Ser Phe Gly
305                 310                 315                 320

Cys Ala Val Ser Thr Ser Ala Ser Phe Ser Gly Ala Val Ser Thr Ser
                325                 330                 335

Ala Cys Phe Ser Gly Ala Pro Ile Thr Asn Pro Gly Phe Gly Gly Ala
                340                 345                 350

Phe Ser Thr Ser Ala Gly Phe Gly Gly Ala Leu Ser Thr Ala Ala Asp
                355                 360                 365

Phe Gly Gly Thr Pro Ser Asn Ser Ile Gly Phe Gly Ala Ala Pro Ser
                370                 375                 380

Thr Ser Val Ser Phe Gly Gly Ala His Gly Thr Ser Leu Cys Phe Gly
385                 390                 395                 400

Gly Ala Pro Ser Thr Ser Leu Cys Phe Gly Ser Ala Ser Asn Thr Asn
                405                 410                 415

Leu Cys Phe Gly Gly Pro Pro Ser Thr Ser Ala Cys Phe Ser Gly Ala
                420                 425                 430

Thr Ser Pro Ser Phe Cys Asp Gly Pro Ser Thr Ser Thr Gly Phe Ser
                435                 440                 445

Phe Gly Asn Gly Leu Ser Thr Gly Gly Gly Leu Asn Thr Ser
                450                 455                 460

Ala Gly Phe Gly Gly Gly Leu Gly Thr Ser Ala Gly Phe Ser Gly Gly
465                 470                 475                 480
```

```
Leu Ser Thr Ser Ser Gly Phe Asp Gly Gly Leu Gly Thr Ser Ala Gly
                485                 490                 495

Phe Gly Gly Gly Pro Gly Thr Ser Thr Gly Phe Gly Gly Leu Gly
        500                 505                 510

Thr Ser Ala Gly Phe Ser Gly Gly Leu Gly Thr Ser Ala Gly Phe Gly
        515                 520                 525

Gly Gly Leu Val Thr Ser Asp Gly Phe Gly Gly Leu Gly Thr Asn
        530                 535                 540

Ala Ser Phe Gly Ser Thr Leu Gly Thr Ser Ala Gly Phe Ser Gly Gly
545                 550                 555                 560

Leu Ser Thr Ser Asp Gly Phe Gly Ser Arg Pro Asn Ala Ser Phe Asp
                565                 570                 575

Arg Gly Leu Ser Thr Ile Ile Gly Phe Gly Ser Gly Ser Asn Thr Ser
                580                 585                 590

Thr Gly Phe Thr Gly Glu Pro Ser Thr Ser Thr Gly Phe Ser Ser Gly
                595                 600                 605

Pro Ser Ser Ile Val Gly Phe Ser Gly Gly Pro Ser Thr Gly Gly Phe
        610                 615                 620

Cys Ser Gly Pro Ser Thr Ser Gly Phe Ser Gly Gly Pro Ser Thr Gly
625                 630                 635                 640

Ala Gly Phe Gly Gly Gly Pro Asn Thr Gly Ala Gly Phe Gly Gly Gly
                645                 650                 655

Pro Ser Thr Ser Ala Gly Phe Gly Ser Gly Ala Ala Ser Leu Gly Ala
                660                 665                 670

Cys Gly
```

(2) INFORMATION FOR SEQ ID NO:4:

(i) SEQUENCE CHARACTERISTICS:
        (A) LENGTH: 2577 base pairs
        (B) TYPE: nucleic acid
        (C) STRANDEDNESS: single
        (D) TOPOLOGY: linear (ix) FEATURE:
        (A) NAME/KEY: CDS
        (B) LOCATION: 111..2445

(xi) SEQUENCE DESCRIPTION: SEQ ID NO:4:

```
CGCCAGGAAC AGCTTGAGGT ACCTGAGCCC TGCCCTCCAG CAGCACCCGA GAGGGTCAGG         60

AGAAAAGCGG AGGAAGCTGG GTAGGCCCTG AGGGGCCTCG GTAAGCCATC ATG ACC          116
                                                        Met Thr
                                                         1

ACC CGG CAA GCC ACG AAG GAT CCC CTC CTC CGG GGT GTA TCT CCT ACC         164
Thr Arg Gln Ala Thr Lys Asp Pro Leu Leu Arg Gly Val Ser Pro Thr
        5                  10                  15

CCT AGC AAG ATT CCG GTA CGC TCT CAG AAA CGC ACG CCT TTC CCC ACT         212
Pro Ser Lys Ile Pro Val Arg Ser Gln Lys Arg Thr Pro Phe Pro Thr
    20                  25                  30

GTT ACA TCG TGC GCC GTG GAC CAG GAG AAC CAA GAT CCA AGG AGA TGG         260
Val Thr Ser Cys Ala Val Asp Gln Glu Asn Gln Asp Pro Arg Arg Trp
35                  40                  45                  50

GTG CAG AAA CCA CCG CTC AAT ATT CAA CGC CCC CTC GTT GAT TCA GCA         308
Val Gln Lys Pro Pro Leu Asn Ile Gln Arg Pro Leu Val Asp Ser Ala
                55                  60                  65

GGC CCC AGG CCG AAA GCC AGG CAC CAG GCA GAG ACA TCA CAA AGA TTG         356
Gly Pro Arg Pro Lys Ala Arg His Gln Ala Glu Thr Ser Gln Arg Leu
            70                  75                  80
```

```
GTG GGG ATC AGT CAG CCT CGG AAC CCC TTG GAA GAG CTC AGG CCT AGC         404
Val Gly Ile Ser Gln Pro Arg Asn Pro Leu Glu Glu Leu Arg Pro Ser
            85                  90                  95

CCT AGG GGT CAA AAT GTG GGG CCT GGG CCC CCT GCC CAG ACA GAG GCT         452
Pro Arg Gly Gln Asn Val Gly Pro Gly Pro Pro Ala Gln Thr Glu Ala
    100                 105                 110

CCA GGG ACC ATA GAG TTT GTG GCT GAC CCT GCA GCC CTG GCC ACC ATC         500
Pro Gly Thr Ile Glu Phe Val Ala Asp Pro Ala Ala Leu Ala Thr Ile
115                 120                 125                 130

CTG TCA GGT GAG GGT GTG AAG AGC TGT CAC CTG GGG CGC CAG CCT AGT         548
Leu Ser Gly Glu Gly Val Lys Ser Cys His Leu Gly Arg Gln Pro Ser
                135                 140                 145

CTG GCT AAA AGA GTA CTG GTT CGA GGA AGT CAG GGA GGC ACC ACC CAG         596
Leu Ala Lys Arg Val Leu Val Arg Gly Ser Gln Gly Gly Thr Thr Gln
            150                 155                 160

AGG GTC CAG GGT GTT CGG GCC TCT GCA TAT TTG GCC CCC AGA ACC CCC         644
Arg Val Gln Gly Val Arg Ala Ser Ala Tyr Leu Ala Pro Arg Thr Pro
        165                 170                 175

ACC CAC CGA CTG GAC CCT GCC AGG GCT TCC TGC TTC TCT AGG CTG GAG         692
Thr His Arg Leu Asp Pro Ala Arg Ala Ser Cys Phe Ser Arg Leu Glu
    180                 185                 190

GGA CCA GGA CCT CGA GGC CGG ACA TTG TGC CCC CAG AGG CTA CAG GCT         740
Gly Pro Gly Pro Arg Gly Arg Thr Leu Cys Pro Gln Arg Leu Gln Ala
195                 200                 205                 210

CTG ATT TCA CCT TCA GGA CCT TCC TTT CAC CCT TCC ACT CAC CCC AGT         788
Leu Ile Ser Pro Ser Gly Pro Ser Phe His Pro Ser Thr His Pro Ser
                215                 220                 225

TTC CAG GAG CTA AGA AGG GAG ACA GCT GGC AGC AGC CGG ACT TCA GTG         836
Phe Gln Glu Leu Arg Arg Glu Thr Ala Gly Ser Ser Arg Thr Ser Val
            230                 235                 240

AGC CAG GCC TCA GGA TTG CTC CTG GAG ACC CCA GTC CAG CCT GCT TTC         884
Ser Gln Ala Ser Gly Leu Leu Leu Glu Thr Pro Val Gln Pro Ala Phe
        245                 250                 255

TCT CTT CCT AAA GGA GAA CGC GAG GTT GTC ACT CAC TCA GAT GAA GGA         932
Ser Leu Pro Lys Gly Glu Arg Glu Val Val Thr His Ser Asp Glu Gly
    260                 265                 270

GGT GTG GCC TCT CTT GGT CTG GCC CAG CGA GTA CCA TTA AGA GAA AAC         980
Gly Val Ala Ser Leu Gly Leu Ala Gln Arg Val Pro Leu Arg Glu Asn
275                 280                 285                 290

CGA GAA ATG TCA CAT ACC AGG GAC AGC CAT GAC TCC CAC CTG ATG CCC        1028
Arg Glu Met Ser His Thr Arg Asp Ser His Asp Ser His Leu Met Pro
                295                 300                 305

TCC CCT GCC CCT GTG GCC CAG CCC TTG CCT GGC CAT GTG GTG CCA TGT        1076
Ser Pro Ala Pro Val Ala Gln Pro Leu Pro Gly His Val Val Pro Cys
            310                 315                 320

CCA TCA CCC TTT GGA CGG GCT CAG CGT GTA CCC TCC CCA GGC CCT CCA        1124
Pro Ser Pro Phe Gly Arg Ala Gln Arg Val Pro Ser Pro Gly Pro Pro
        325                 330                 335

ACT CTG ACC TCA TAT TCA GTG TTG CGG CGT CTC ACC GTT CAA CCT AAA        1172
Thr Leu Thr Ser Tyr Ser Val Leu Arg Arg Leu Thr Val Gln Pro Lys
    340                 345                 350

ACC CGG TTC ACA CCC ATG CCA TCA ACC CCC AGA GTT CAG CAG GCC CAG        1220
Thr Arg Phe Thr Pro Met Pro Ser Thr Pro Arg Val Gln Gln Ala Gln
355                 360                 365                 370

TGG CTG CGT GGT GTC TCC CCT CAG TCC TGC TCT GAA GAT CCT GCC CTG        1268
Trp Leu Arg Gly Val Ser Pro Gln Ser Cys Ser Glu Asp Pro Ala Leu
                375                 380                 385

CCC TGG GAG CAG GTT GCC GTC CGG TTG TTT GAC CAG GAG AGT TGT ATA        1316
Pro Trp Glu Gln Val Ala Val Arg Leu Phe Asp Gln Glu Ser Cys Ile
```

-continued

```
                390                      395                      400
AGG TCA CTG GAG GGT TCT GGG AAA CCA CCG GTG GCC ACT CCT TCT GGA      1364
Arg Ser Leu Glu Gly Ser Gly Lys Pro Pro Val Ala Thr Pro Ser Gly
            405                      410                      415

CCC CAC TCT AAC AGA ACC CCC AGC CTC CAG GAG GTG AAG ATT CAA CGC      1412
Pro His Ser Asn Arg Thr Pro Ser Leu Gln Glu Val Lys Ile Gln Arg
        420                      425                      430

ATC GGT ATC CTG CAA CAG CTG TTG AGA CAG GAA GTA GAG GGG CTG GTA      1460
Ile Gly Ile Leu Gln Gln Leu Leu Arg Gln Glu Val Glu Gly Leu Val
435                      440                      445                      450

GGG GGC CAG TGT GTC CCT CTT AAT GGA GGC TCT TCT CTG GAT ATG GTT      1508
Gly Gly Gln Cys Val Pro Leu Asn Gly Gly Ser Ser Leu Asp Met Val
                455                      460                      465

GAA CTT CAG CCC CTG CTG ACT GAG ATT TCT AGA ACT CTG AAT GCC ACA      1556
Glu Leu Gln Pro Leu Leu Thr Glu Ile Ser Arg Thr Leu Asn Ala Thr
            470                      475                      480

GAG CAT AAC TCT GGG ACT TCC CAC CTT CCT GGA CTG TTA AAA CAC TCA      1604
Glu His Asn Ser Gly Thr Ser His Leu Pro Gly Leu Leu Lys His Ser
        485                      490                      495

GGG CTG CCA AAG CCC TGT CTT CCA GAG GAG TGC GGG GAA CCA CAG CCC      1652
Gly Leu Pro Lys Pro Cys Leu Pro Glu Glu Cys Gly Glu Pro Gln Pro
    500                      505                      510

TGC CCT CCG GCA GAG CCT GGG CCC CCA GAG GCC TTC TGT AGG AGT GAG      1700
Cys Pro Pro Ala Glu Pro Gly Pro Pro Glu Ala Phe Cys Arg Ser Glu
515                      520                      525                      530

CCT GAG ATA CCA GAG CCC TCC CTC CAG GAA CAG CTT GAA GTA CCA GAG      1748
Pro Glu Ile Pro Glu Pro Ser Leu Gln Glu Gln Leu Glu Val Pro Glu
                535                      540                      545

CCC TAC CCT CCA GCA GAA CCC AGG CCC CTA GAG TCC TGC TGT AGG AGT      1796
Pro Tyr Pro Pro Ala Glu Pro Arg Pro Leu Glu Ser Cys Cys Arg Ser
            550                      555                      560

GAG CCT GAG ATA CCG GAG TCC TCT CGC CAG GAA CAG CTT GAG GTA CCT      1844
Glu Pro Glu Ile Pro Glu Ser Ser Arg Gln Glu Gln Leu Glu Val Pro
        565                      570                      575

GAG CCC TGC CCT CCA GCA GAA CCC AGG CCC CTA GAG TCC TAC TGT AGG      1892
Glu Pro Cys Pro Pro Ala Glu Pro Arg Pro Leu Glu Ser Tyr Cys Arg
    580                      585                      590

ATT GAG CCT GAG ATA CCG GAG TCC TCT CGC CAG GAA CAG CTT GAG GTA      1940
Ile Glu Pro Glu Ile Pro Glu Ser Ser Arg Gln Glu Gln Leu Glu Val
595                      600                      605                      610

CCT GAG CCC TGC CCT CCA GCA GAA CCC GGG CCC CTT CAG CCC AGC ACC      1988
Pro Glu Pro Cys Pro Pro Ala Glu Pro Gly Pro Leu Gln Pro Ser Thr
                615                      620                      625

CAG GGG CAG TCT GGA CCC CCA GGG CCC TGC CCT AGG GTA GAG CTG GGG      2036
Gln Gly Gln Ser Gly Pro Pro Gly Pro Cys Pro Arg Val Glu Leu Gly
            630                      635                      640

GCA TCA GAG CCC TGC ACC CTG GAA CAT AGA AGT CTA GAG TCC AGT CTA      2084
Ala Ser Glu Pro Cys Thr Leu Glu His Arg Ser Leu Glu Ser Ser Leu
        645                      650                      655

CCA CCC TGC TGC AGT CAG TGG GCT CCA GCA ACC ACC AGC CTG ATC TTC      2132
Pro Pro Cys Cys Ser Gln Trp Ala Pro Ala Thr Thr Ser Leu Ile Phe
    660                      665                      670

TCT TCC CAA CAC CCG CTT TGT GCC AGC CCC CCT ATC TGC TCA CTC CAG      2180
Ser Ser Gln His Pro Leu Cys Ala Ser Pro Pro Ile Cys Ser Leu Gln
675                      680                      685                      690

TCT TTG AGA CCC CCA GCA GGC CAG GCA GGC CTC AGC AAT CTG GCC CCT      2228
Ser Leu Arg Pro Pro Ala Gly Gln Ala Gly Leu Ser Asn Leu Ala Pro
                695                      700                      705

CGA ACC CTA GCC CTG AGG GAG AGC CTC AAA TCG TGT TTA ACC GCC ATC      2276
```

```
Arg Thr Leu Ala Leu Arg Glu Ser Leu Lys Ser Cys Leu Thr Ala Ile
        710                 715                 720

CAC TGC TTC CAC GAG GCT CGT CTG GAC GAT GAG TGT GCC TTT TAC ACC      2324
His Cys Phe His Glu Ala Arg Leu Asp Asp Glu Cys Ala Phe Tyr Thr
        725                 730                 735

AGC CGA GCC TCT CCC TCA GGC CCC ACC CGG GTC TGC ACC AAC CCT GTG      2372
Ser Arg Ala Ser Pro Ser Gly Pro Thr Arg Val Cys Thr Asn Pro Val
    740                 745                 750

GCT ACA TTA CTC GAA TGG CAG GAT GCC CTG TGT TTC ATT CCA GTT GGT      2420
Ala Thr Leu Leu Glu Trp Gln Asp Ala Leu Cys Phe Ile Pro Val Gly
755                 760                 765                 770

TCT GCT GCC CCC CAG GGC TCT CCA T GATGAGACAA CCACTCCTGC              2465
Ser Ala Ala Pro Gln Gly Ser Pro
                775

CCTGCCGTAC TTCTTCCTTT TAGCCCTTAT TTATTGTCGG TCTGCCCATG GGACTGGGAG    2525

CCGCCCACTT TTGTCCTCAA TAAAGTTTCT AAAGTAAAAA AAAAAAAAAA AA            2577

(2) INFORMATION FOR SEQ ID NO:5:

(i) SEQUENCE CHARACTERISTICS:
        (A) LENGTH: 778 amino acids
        (B) TYPE: amino acid
        (D) TOPOLOGY: linear (ii) MOLECULE TYPE: protein (xi) SEQUENCE DESCRIPTION: SEQ ID NO:5:

Met Thr Thr Arg Gln Ala Thr Lys Asp Pro Leu Leu Arg Gly Val Ser
 1               5                  10                  15

Pro Thr Pro Ser Lys Ile Pro Val Arg Ser Gln Lys Arg Thr Pro Phe
            20                  25                  30

Pro Thr Val Thr Ser Cys Ala Val Asp Gln Glu Asn Gln Asp Pro Arg
        35                  40                  45

Arg Trp Val Gln Lys Pro Pro Leu Asn Ile Gln Arg Pro Leu Val Asp
    50                  55                  60

Ser Ala Gly Pro Arg Pro Lys Ala Arg His Gln Ala Glu Thr Ser Gln
65                  70                  75                  80

Arg Leu Val Gly Ile Ser Gln Pro Arg Asn Pro Leu Glu Glu Leu Arg
                85                  90                  95

Pro Ser Pro Arg Gly Gln Asn Val Gly Pro Gly Pro Ala Gln Thr
            100                 105                 110

Glu Ala Pro Gly Thr Ile Glu Phe Val Ala Asp Pro Ala Leu Ala
        115                 120                 125

Thr Ile Leu Ser Gly Glu Gly Val Lys Ser Cys His Leu Gly Arg Gln
130                 135                 140

Pro Ser Leu Ala Lys Arg Val Leu Val Arg Gly Ser Gln Gly Gly Thr
145                 150                 155                 160

Thr Gln Arg Val Gln Gly Val Arg Ala Ser Ala Tyr Leu Ala Pro Arg
                165                 170                 175

Thr Pro Thr His Arg Leu Asp Pro Ala Arg Ala Ser Cys Phe Ser Arg
            180                 185                 190

Leu Glu Gly Pro Gly Pro Arg Gly Arg Thr Leu Cys Pro Gln Arg Leu
        195                 200                 205

Gln Ala Leu Ile Ser Pro Ser Gly Pro Ser Phe His Pro Ser Thr His
    210                 215                 220

Pro Ser Phe Gln Glu Leu Arg Arg Glu Thr Ala Gly Ser Ser Arg Thr
225                 230                 235                 240
```

```
Ser Val Ser Gln Ala Ser Gly Leu Leu Glu Thr Pro Val Gln Pro
            245                 250                 255

Ala Phe Ser Leu Pro Lys Gly Arg Glu Val Val Thr His Ser Asp
            260                 265                 270

Glu Gly Gly Val Ala Ser Leu Gly Leu Ala Gln Arg Val Pro Leu Arg
            275                 280                 285

Glu Asn Arg Glu Met Ser His Thr Arg Asp Ser His Asp Ser His Leu
            290                 295                 300

Met Pro Ser Pro Ala Pro Val Ala Gln Pro Leu Pro Gly His Val Val
305                 310                 315                 320

Pro Cys Pro Ser Pro Phe Gly Arg Ala Gln Arg Val Pro Ser Pro Gly
                325                 330                 335

Pro Pro Thr Leu Thr Ser Tyr Ser Val Leu Arg Arg Leu Thr Val Gln
            340                 345                 350

Pro Lys Thr Arg Phe Thr Pro Met Pro Ser Thr Pro Arg Val Gln Gln
            355                 360                 365

Ala Gln Trp Leu Arg Gly Val Ser Pro Gln Ser Cys Ser Glu Asp Pro
            370                 375                 380

Ala Leu Pro Trp Glu Gln Val Ala Val Arg Leu Phe Asp Gln Glu Ser
385                 390                 395                 400

Cys Ile Arg Ser Leu Glu Gly Ser Gly Lys Pro Val Ala Thr Pro
            405                 410                 415

Ser Gly Pro His Ser Asn Arg Thr Pro Ser Leu Gln Glu Val Lys Ile
            420                 425                 430

Gln Arg Ile Gly Ile Leu Gln Gln Leu Leu Arg Gln Glu Val Glu Gly
            435                 440                 445

Leu Val Gly Gly Gln Cys Val Pro Leu Asn Gly Gly Ser Ser Leu Asp
450                 455                 460

Met Val Glu Leu Gln Pro Leu Leu Thr Glu Ile Ser Arg Thr Leu Asn
465                 470                 475                 480

Ala Thr Glu His Asn Ser Gly Thr Ser His Leu Pro Gly Leu Leu Lys
            485                 490                 495

His Ser Gly Leu Pro Lys Pro Cys Leu Pro Glu Glu Cys Gly Glu Pro
            500                 505                 510

Gln Pro Cys Pro Pro Ala Glu Pro Gly Pro Pro Glu Ala Phe Cys Arg
            515                 520                 525

Ser Glu Pro Glu Ile Pro Glu Pro Ser Leu Gln Glu Gln Leu Glu Val
            530                 535                 540

Pro Glu Pro Tyr Pro Pro Ala Glu Pro Arg Pro Leu Glu Ser Cys Cys
545                 550                 555                 560

Arg Ser Glu Pro Glu Ile Pro Glu Ser Arg Gln Glu Gln Leu Glu
            565                 570                 575

Val Pro Glu Pro Cys Pro Pro Ala Glu Pro Arg Pro Leu Glu Ser Tyr
            580                 585                 590

Cys Arg Ile Glu Pro Glu Ile Pro Glu Ser Ser Arg Gln Glu Gln Leu
            595                 600                 605

Glu Val Pro Glu Pro Cys Pro Pro Ala Glu Pro Gly Pro Leu Gln Pro
            610                 615                 620

Ser Thr Gln Gly Gln Ser Gly Pro Pro Gly Pro Cys Pro Arg Val Glu
625                 630                 635                 640

Leu Gly Ala Ser Glu Pro Cys Thr Leu Glu His Arg Ser Leu Glu Ser
            645                 650                 655
```

```
Ser Leu Pro Pro Cys Cys Ser Gln Trp Ala Pro Ala Thr Thr Ser Leu
            660                 665                 670

Ile Phe Ser Ser Gln His Pro Leu Cys Ala Ser Pro Ile Cys Ser
            675                 680                 685

Leu Gln Ser Leu Arg Pro Pro Ala Gly Gln Ala Gly Leu Ser Asn Leu
    690                 695                 700

Ala Pro Arg Thr Leu Ala Leu Arg Glu Ser Leu Lys Ser Cys Leu Thr
705                 710                 715                 720

Ala Ile His Cys Phe His Glu Ala Arg Leu Asp Asp Glu Cys Ala Phe
                725                 730                 735

Tyr Thr Ser Arg Ala Ser Pro Ser Gly Pro Thr Arg Val Cys Thr Asn
            740                 745                 750

Pro Val Ala Thr Leu Leu Glu Trp Gln Asp Ala Leu Cys Phe Ile Pro
            755                 760                 765

Val Gly Ser Ala Ala Pro Gln Gly Ser Pro
770                 775
```

(2) INFORMATION FOR SEQ ID NO:6:

(i) SEQUENCE CHARACTERISTICS:
        (A) LENGTH: 1293 base pairs
        (B) TYPE: nucleic acid
        (C) STRANDEDNESS: single
        (D) TOPOLOGY: linear (ix) FEATURE:
        (A) NAME/KEY: CDS
        (B) LOCATION: 70..988

(xi) SEQUENCE DESCRIPTION: SEQ ID NO:6:

```
AATTCGCGTG CCATAGAGAT GTTCATGAAC AAGAACCCTC CTGCCAGGCG CACCCTGGCT           60

GACATCATC ATG GAG AAG CTG ACT GAG AAG CAG ACA GAG GTT GAG ACA             108
          Met Glu Lys Leu Thr Glu Lys Gln Thr Glu Val Glu Thr
            1               5                  10

GTC ATG TCA GAG GTG TCG GGC TTC CCT ATG CCC CAG CTG GAC CCC CGG           156
Val Met Ser Glu Val Ser Gly Phe Pro Met Pro Gln Leu Asp Pro Arg
 15                  20                  25

GTC CTA GAA GTG TAC AGG GGG GTC CGG GAG GTA TTA TCT AAG TAC CGC           204
Val Leu Glu Val Tyr Arg Gly Val Arg Glu Val Leu Ser Lys Tyr Arg
 30                  35                  40                  45

AGT GGA AAA CTG CCC AAG GCA TTT AAG ATC ATC CCT GCA CTC TCC AAC           252
Ser Gly Lys Leu Pro Lys Ala Phe Lys Ile Ile Pro Ala Leu Ser Asn
                 50                  55                  60

TGG GAG CAA ATC CTC TAC GTC ACA GAG CCG GAG GCC TGG ACT GCA GCT           300
Trp Glu Gln Ile Leu Tyr Val Thr Glu Pro Glu Ala Trp Thr Ala Ala
             65                  70                  75

GCC ATG TAC CAG GCC ACC AGG ATT TTT GCC TCT AAC CTG AAG GAA CGC           348
Ala Met Tyr Gln Ala Thr Arg Ile Phe Ala Ser Asn Leu Lys Glu Arg
         80                  85                  90

ATG GCC CAG CGC TTC TAC AAC CTT GTC CTG CTC CCT CGA GTA CGA GAT           396
Met Ala Gln Arg Phe Tyr Asn Leu Val Leu Leu Pro Arg Val Arg Asp
     95                 100                 105

GAC GTT GGT GAA TAC AAA CGA CTC AAC TTC CAT CTC TAC ATG GCT CTC           444
Asp Val Gly Glu Tyr Lys Arg Leu Asn Phe His Leu Tyr Met Ala Leu
110                 115                 120                 125

AAG AAG GCC CTT TTC AAA CCT GGA GCC TGG TTC AAA GGG ATC CTG ATT           492
Lys Lys Ala Leu Phe Lys Pro Gly Ala Trp Phe Lys Gly Ile Leu Ile
                130                 135                 140

CCA CTG TGC GAG TCT GGC ACT TGT ACC CTC CGG GAA GCC ATC ATT GTG           540
Pro Leu Cys Glu Ser Gly Thr Cys Thr Leu Arg Glu Ala Ile Ile Val
```

-continued

```
                     145                 150                 155
GGT AGC ATC ATC ACC AAG TGC TCC ATC CCT GTG TTG CAC TCC AGT GCG        588
Gly Ser Ile Ile Thr Lys Cys Ser Ile Pro Val Leu His Ser Ser Ala
        160                 165                 170

GCC ATG CTG AAA ATT GCT GAG ATG GAA TAC AGC GGT GCC AAC AGC ATC        636
Ala Met Leu Lys Ile Ala Glu Met Glu Tyr Ser Gly Ala Asn Ser Ile
175                 180                 185

TTC CTG CGA CTG CTG CTG GAT AAG AAG TAT GCA CTG CCT TAC CGG GTG        684
Phe Leu Arg Leu Leu Leu Asp Lys Lys Tyr Ala Leu Pro Tyr Arg Val
190                 195                 200                 205

CTG GAT GCC CTA GTC TTC CAC TTC CTG GGG TTC CGG ACA GAG AAG CGT        732
Leu Asp Ala Leu Val Phe His Phe Leu Gly Phe Arg Thr Glu Lys Arg
                210                 215                 220

GAA CTG CCT GTG CTG TGG CAC CAG TGC CTC CTG ACT TTG GTC CAG CGC        780
Glu Leu Pro Val Leu Trp His Gln Cys Leu Leu Thr Leu Val Gln Arg
                225                 230                 235

TAC AAG GCC GAC TTG GCC ACA GAC CAG AAA GAG GCC CTC TTA GAA CTG        828
Tyr Lys Ala Asp Leu Ala Thr Asp Gln Lys Glu Ala Leu Leu Glu Leu
            240                 245                 250

CTC CGG CTG CAG CCC CAT CCA CAG CTA TCG CCC GAA ATC AGG CGT GAG        876
Leu Arg Leu Gln Pro His Pro Gln Leu Ser Pro Glu Ile Arg Arg Glu
        255                 260                 265

CTT CAG AGT GCA GCC CCC GCA TGT GGA AGA TGT CCC CAT CAC CGT GGA        924
Leu Gln Ser Ala Ala Pro Ala Cys Gly Arg Cys Pro His His Arg Gly
270                 275                 280                 285

GTG AGG AAA ACA GTC AGC TTG TCC TGG CCA AAG GGG TTT GGA AGG ACA        972
Val Arg Lys Thr Val Ser Leu Ser Trp Pro Lys Gly Phe Gly Arg Thr
                290                 295                 300

CCA AGA CCC CGT TGG T GACTGAAGAT GACACTGAGC TTTAATGGCT GAAGACCCAG     1028
Pro Arg Pro Arg Trp
                305

ATCAGGGCAG TGACCAGATC ACAGGGACAT CTGTGGCTCC CAGTCCAGGA CAGGAAGGAC     1088

TGAGGGTCTG GCTGGTTCCC TCTTCCATTC TAGGCCCTTA TCCCTGTTTA GTTCTGAGAG     1148

CCAACTTGAG ATACCATATG CTAGCATTCC CAGTCCCCAG CTGGGGCTTG GTGTGAGTAC     1208

TTTTTCTATG GCTATTGTGT CAGGTCACTG TGGATAAAGG CAAAGACAGA TATTTATTGA     1268

AAAAAAAAAA AAAAAAAAAA AAAAA                                           1293

(2) INFORMATION FOR SEQ ID NO:7:

(i) SEQUENCE CHARACTERISTICS:
        (A) LENGTH: 306 amino acids
        (B) TYPE: amino acid
        (D) TOPOLOGY: linear (ii) MOLECULE TYPE: protein (xi) SEQUENCE DESCRIPTION: SEQ ID NO:7:

Met Glu Lys Leu Thr Glu Lys Gln Thr Glu Val Glu Thr Val Met Ser
1               5                   10                  15

Glu Val Ser Gly Phe Pro Met Pro Gln Leu Asp Pro Arg Val Leu Glu
            20                  25                  30

Val Tyr Arg Gly Val Arg Glu Val Leu Ser Lys Tyr Arg Ser Gly Lys
        35                  40                  45

Leu Pro Lys Ala Phe Lys Ile Ile Pro Ala Leu Ser Asn Trp Glu Gln
    50                  55                  60

Ile Leu Tyr Val Thr Glu Pro Glu Ala Trp Thr Ala Ala Ala Met Tyr
65                  70                  75                  80
```

```
Gln Ala Thr Arg Ile Phe Ala Ser Asn Leu Lys Glu Arg Met Ala Gln
             85                  90                  95

Arg Phe Tyr Asn Leu Val Leu Leu Pro Arg Val Arg Asp Asp Val Gly
            100                 105                 110

Glu Tyr Lys Arg Leu Asn Phe His Leu Tyr Met Ala Leu Lys Lys Ala
            115                 120                 125

Leu Phe Lys Pro Gly Ala Trp Phe Lys Gly Ile Leu Ile Pro Leu Cys
    130                 135                 140

Glu Ser Gly Thr Cys Thr Leu Arg Glu Ala Ile Ile Val Gly Ser Ile
145                 150                 155                 160

Ile Thr Lys Cys Ser Ile Pro Val Leu His Ser Ser Ala Ala Met Leu
                165                 170                 175

Lys Ile Ala Glu Met Glu Tyr Ser Gly Ala Asn Ser Ile Phe Leu Arg
            180                 185                 190

Leu Leu Leu Asp Lys Lys Tyr Ala Leu Pro Tyr Arg Val Leu Asp Ala
            195                 200                 205

Leu Val Phe His Phe Leu Gly Phe Arg Thr Glu Lys Arg Glu Leu Pro
    210                 215                 220

Val Leu Trp His Gln Cys Leu Leu Thr Leu Val Gln Arg Tyr Lys Ala
225                 230                 235                 240

Asp Leu Ala Thr Asp Gln Lys Glu Ala Leu Leu Glu Leu Leu Arg Leu
            245                 250                 255

Gln Pro His Pro Gln Leu Ser Pro Glu Ile Arg Arg Glu Leu Gln Ser
            260                 265                 270

Ala Ala Pro Ala Cys Gly Arg Cys Ser His His Arg Gly Val Arg Lys
            275                 280                 285

Thr Val Ser Leu Ser Trp Pro Lys Gly Phe Gly Arg Thr Pro Arg Pro
    290                 295                 300

Arg Trp
305

(2) INFORMATION FOR SEQ ID NO:8:

(i) SEQUENCE CHARACTERISTICS:
        (A) LENGTH: 2223 base pairs
        (B) TYPE: nucleic acid
        (C) STRANDEDNESS: single
        (D) TOPOLOGY: linear (ix) FEATURE:
        (A) NAME/KEY: CDS
        (B) LOCATION: 199..2223

(xi) SEQUENCE DESCRIPTION: SEQ ID NO:8:

CACCTCTGTC GTTCCCCAGT GTTCCACAAG AAGAAACCTT ACGTCAGGCC CCTGCTGGAC        60

TCCCCCGAGA AACTCTGTTC CAATCCCGCG TTCTTCCTCC CAAAGAAATT CCTTCTTTGT       120

CTCCCACCAT TCCCCGTCAA GGCTCCCTGC CCCAAACTTC CAGTGCTCCC AAGCAAGAGA       180

CTTCTGGCTG GATGCCAC ATG TGC TCC AGA AGG GAC CCT CAC TCC TGT GTT        231
                    Met Cys Ser Arg Arg Asp Pro His Ser Cys Val
                     1               5                  10

CTG CCG CTT CTG AGC AAG AGA CTT CTC TCC AGG GCC CCC TGG CTT CCC        279
Leu Pro Leu Leu Ser Lys Arg Leu Leu Ser Arg Ala Pro Trp Leu Pro
            15                  20                  25

AGG AAG GGA CCC AGT ATC CAC CCC CAG CTG GTG GTG AAC AAG AAG CCT        327
Arg Lys Gly Pro Ser Ile His Pro Gln Leu Val Val Asn Lys Lys Pro
        30                  35                  40

CCC TTC TCT CCC ACT CCC CCC ACC ACC AGG AAG CCC CCG CTC ACT CCC        375
```

-continued

```
         Pro Phe Ser Pro Thr Pro Pro Thr Thr Arg Lys Pro Pro Leu Thr Pro
                     45                  50                  55

CTG AAG CTC CTG AGA AAG ACC CCT GAC CCT TCC CCA ACA GTT CCC GAG             423
Leu Lys Leu Leu Arg Lys Thr Pro Asp Pro Ser Pro Thr Val Pro Glu
 60                  65                  70                  75

ACT GAC ATG GAC CCG CTG CTC CAG AGC CCG GTT TCC CAA AAG GAC ACC             471
Thr Asp Met Asp Pro Leu Leu Gln Ser Pro Val Ser Gln Lys Asp Thr
                     80                  85                  90

CCT TTC CAG ATC TCT TCT GGA GTC CAG AAG GAA CAG CCG CTC CCC ACG             519
Pro Phe Gln Ile Ser Ser Gly Val Gln Lys Glu Gln Pro Leu Pro Thr
                 95                 100                 105

GGA GAG ATC ACC CGC TTG GGT GTG TGG GCT GCC GTC CAA GCA GTG GAG             567
Gly Glu Ile Thr Arg Leu Gly Val Trp Ala Ala Val Gln Ala Val Glu
            110                 115                 120

AGG AAG CTG GAG GCC CAG GCC ATG AGG CTA CTG ACC CTG GAA GGC AGG             615
Arg Lys Leu Glu Ala Gln Ala Met Arg Leu Leu Thr Leu Glu Gly Arg
        125                 130                 135

ACG GGG ACA AAT GAA AAG AAG ATA GCC GAC TGC GAG AAG ACA GCC GTG             663
Thr Gly Thr Asn Glu Lys Lys Ile Ala Asp Cys Glu Lys Thr Ala Val
140                 145                 150                 155

GAG TTC GCG AAC CAT CTG GAG AGC AAG TGG GTC GTG TTG GGG ACC CTG             711
Glu Phe Ala Asn His Leu Glu Ser Lys Trp Val Val Leu Gly Thr Leu
                160                 165                 170

CTG CAG GAG TAT GGG CTG CAG CAG AGG CGG CTG GAG AAC ATG GAG AAC             759
Leu Gln Glu Tyr Gly Leu Gln Gln Arg Arg Leu Glu Asn Met Glu Asn
                175                 180                 185

CTG CTG AAA AAC AGA AAT TTC TGG ATC CTG CGG CTG CCC CCC GGC AGC             807
Leu Leu Lys Asn Arg Asn Phe Trp Ile Leu Arg Leu Pro Pro Gly Ser
            190                 195                 200

AAT GGA GAA GTT CCC AAG GTC CCT GTC ACA TTT GAT GAT GTT GCT GTG             855
Asn Gly Glu Val Pro Lys Val Pro Val Thr Phe Asp Asp Val Ala Val
205                 210                 215

CAC TTC TCG GAG CAG GAG TGG GGA AAC CTG TCT GAG TGG CAG AAG GAG             903
His Phe Ser Glu Gln Glu Trp Gly Asn Leu Ser Glu Trp Gln Lys Glu
220                 225                 230                 235

CTC TAC AAG AAC GTG ATG AGG GGC AAC TAC GAG TCC CTG GTT TCC ATG             951
Leu Tyr Lys Asn Val Met Arg Gly Asn Tyr Glu Ser Leu Val Ser Met
                240                 245                 250

GAC TAT GCA ATT TCC AAA CCA GAC CTC ATG TCA CAG ATG GAG CGC GGG             999
Asp Tyr Ala Ile Ser Lys Pro Asp Leu Met Ser Gln Met Glu Arg Gly
                255                 260                 265

GAG CGG CCC ACC ATG CAG GAG CAG GAA GAC TCT GAG GAG GGC GAA ACG            1047
Glu Arg Pro Thr Met Gln Glu Gln Glu Asp Ser Glu Glu Gly Glu Thr
            270                 275                 280

CCG ACA GAT CCC AGT GCT GCG CAC GAT GGG ATC GTG ATT AAG ATC GAG            1095
Pro Thr Asp Pro Ser Ala Ala His Asp Gly Ile Val Ile Lys Ile Glu
285                 290                 295

GTA CAG ACC AAC GAC GAG GGC TCA GAA AGT TTG GAG ACA CCT GAG CCC            1143
Val Gln Thr Asn Asp Glu Gly Ser Glu Ser Leu Glu Thr Pro Glu Pro
300                 305                 310                 315

CTG ATG GGA CAG GTG GAA GAG CAC GGC TTC CAG GAC TCA GAG CTG GGT            1191
Leu Met Gly Gln Val Glu Glu His Gly Phe Gln Asp Ser Glu Leu Gly
                320                 325                 330

GAN CCC TGT GGG GAA CAG CCA GAC CTG GAC ATG CAG GAG CCA GAG AAC            1239
Xaa Pro Cys Gly Glu Gln Pro Asp Leu Asp Met Gln Glu Pro Glu Asn
                335                 340                 345

ACG CTG GAG GAG TCC ACG GAA GGC TCC AGC GAG TTC AGC GAA CTG AAG            1287
Thr Leu Glu Glu Ser Thr Glu Gly Ser Ser Glu Phe Ser Glu Leu Lys
350                 355                 360
```

```
CAG ATG CTG GTG CAG CAG AGG AAC TGC ACG GAG GGG ATC GTG ATC AAG      1335
Gln Met Leu Val Gln Gln Arg Asn Cys Thr Glu Gly Ile Val Ile Lys
    365                 370                 375

ACA GAG GAA CAA GAC GAG GAG GAA GAA GAG GAG GAG GAG GAT GAG CTG      1383
Thr Glu Glu Gln Asp Glu Glu Glu Glu Glu Glu Glu Glu Asp Glu Leu
380                 385                 390                 395

CCG CAG CAC TTG CAA TCC CTT GGG CAG CTG TCC GGG AGA TAT GAG GCC      1431
Pro Gln His Leu Gln Ser Leu Gly Gln Leu Ser Gly Arg Tyr Glu Ala
                400                 405                 410

AGT ATG TAC CAG ACC CCG CTG CCC GGG GAG ATG TCC CCC GAG GGC GAG      1479
Ser Met Tyr Gln Thr Pro Leu Pro Gly Glu Met Ser Pro Glu Gly Glu
            415                 420                 425

GAG AGC CCC CCG CCC CTG CAG GTT GGA AAC CCC GCA GTG AAA AGG CTG      1527
Glu Ser Pro Pro Pro Leu Gln Val Gly Asn Pro Ala Val Lys Arg Leu
        430                 435                 440

GCG CCC TCC GTG CAC GGT GAG CGG GAC CTG AGC GAG AAC CGC GGG GGC      1575
Ala Pro Ser Val His Gly Glu Arg Asp Leu Ser Glu Asn Arg Gly Gly
    445                 450                 455

TCG AGC CAG CAG AGT GGG AAC CGG CGC GGC GAG CGG CCC TTC ACA TGC      1623
Ser Ser Gln Gln Ser Gly Asn Arg Arg Gly Glu Arg Pro Phe Thr Cys
460                 465                 470                 475

ATG GAG TGC GGC AAG AGC TTC CGC CTG AAG ATC AAC CTC ATC ATC CAC      1671
Met Glu Cys Gly Lys Ser Phe Arg Leu Lys Ile Asn Leu Ile Ile His
                480                 485                 490

CAC CAG CGC AAC CAA CAT CAA GGA GGG GGC CCT ACG AGT GCG CCG AAT      1719
His Gln Arg Asn Gln His Gln Gly Gly Gly Pro Thr Ser Ala Pro Asn
            495                 500                 505

GTG AGA TCA GCT TTC CGG CAC AAG CAA CAG CTC ACG CTG CAC CAG CGC      1767
Val Arg Ser Ala Phe Arg His Lys Gln Gln Leu Thr Leu His Gln Arg
        510                 515                 520

ATC CAC CGC GTG CGC GGA GGC TGC GTC TCA CCC GAA CGC GGG CCC ACG      1815
Ile His Arg Val Arg Gly Gly Cys Val Ser Pro Glu Arg Gly Pro Thr
    525                 530                 535

TTC AAC CCC AAG NAC GCG CTC AAG CCG CGT CCC AAG TCA CCC AGC TCT      1863
Phe Asn Pro Lys Xaa Ala Leu Lys Pro Arg Pro Lys Ser Pro Ser Ser
540                 545                 550                 555

GGT AGC GGC GGC GGT GGC CCT AAG CCC TAC AAG TGC CCC GAG TGC GAC      1911
Gly Ser Gly Gly Gly Gly Pro Lys Pro Tyr Lys Cys Pro Glu Cys Asp
                560                 565                 570

AGC AGC TTC AGC CAC AAG TCC AGC CTG ACT AAA CAC CAG ATC ACG CAC      1959
Ser Ser Phe Ser His Lys Ser Ser Leu Thr Lys His Gln Ile Thr His
            575                 580                 585

ACG GGT GAG CGG CCC TAC ACG TGC CCC GAG TGC AAG AAG AGC TTC CGC      2007
Thr Gly Glu Arg Pro Tyr Thr Cys Pro Glu Cys Lys Lys Ser Phe Arg
        590                 595                 600

CTG CAC ATC AGC TTG GTG ATC CAT CAG CGC GTG CAC GCG GGC AAG CAT      2055
Leu His Ile Ser Leu Val Ile His Gln Arg Val His Ala Gly Lys His
    605                 610                 615

GAG GTC TCC TTC ATC TGC AGC CTG TGC GGC AAG AGC TTC AGC CGC CCC      2103
Glu Val Ser Phe Ile Cys Ser Leu Cys Gly Lys Ser Phe Ser Arg Pro
620                 625                 630                 635

TCG CAC CTG CTG CGC CAC CAG CGG ACT CAC ACA GGC GAG CGG CCC TTC      2151
Ser His Leu Leu Arg His Gln Arg Thr His Thr Gly Glu Arg Pro Phe
                640                 645                 650

AAG TGC CCC GAG TGC GAG AAG AGC TTC AGC GAG AAG TCC AAG CTC ACC      2199
Lys Cys Pro Glu Cys Glu Lys Ser Phe Ser Glu Lys Ser Lys Leu Thr
            655                 660                 665

AAC CAC TGC CGC GTG CAC TCG CGC                                      2223
Asn His Cys Arg Val His Ser Arg
            670                 675
```

(2) INFORMATION FOR SEQ ID NO:9:

(i) SEQUENCE CHARACTERISTICS:
        (A) LENGTH: 675 amino acids
        (B) TYPE: amino acid
        (D) TOPOLOGY: linear (ii) MOLECULE TYPE: protein (xi) SEQUENCE DESCRIPTION: SEQ ID NO:9:

```
Met Cys Ser Arg Arg Asp Pro His Ser Cys Val Leu Pro Leu Leu Ser
 1               5                  10                  15

Lys Arg Leu Leu Ser Arg Ala Pro Trp Leu Pro Arg Lys Gly Pro Ser
            20                  25                  30

Ile His Pro Gln Leu Val Val Asn Lys Lys Pro Pro Phe Ser Pro Thr
        35                  40                  45

Pro Pro Thr Thr Arg Lys Pro Leu Thr Pro Leu Lys Leu Leu Arg
    50                  55                  60

Lys Thr Pro Asp Pro Ser Pro Thr Val Pro Glu Thr Asp Met Asp Pro
 65                  70                  75                  80

Leu Leu Gln Ser Pro Val Ser Gln Lys Asp Thr Pro Phe Gln Ile Ser
                85                  90                  95

Ser Gly Val Gln Lys Glu Gln Pro Leu Pro Thr Gly Glu Ile Thr Arg
            100                 105                 110

Leu Gly Val Trp Ala Ala Val Gln Ala Val Glu Arg Lys Leu Glu Ala
        115                 120                 125

Gln Ala Met Arg Leu Leu Thr Leu Glu Gly Arg Thr Gly Thr Asn Glu
130                 135                 140

Lys Lys Ile Ala Asp Cys Glu Lys Thr Ala Val Glu Phe Ala Asn His
145                 150                 155                 160

Leu Glu Ser Lys Trp Val Val Leu Gly Thr Leu Leu Gln Glu Tyr Gly
                165                 170                 175

Leu Gln Gln Arg Arg Leu Glu Asn Met Glu Asn Leu Leu Lys Asn Arg
            180                 185                 190

Asn Phe Trp Ile Leu Arg Leu Pro Pro Gly Ser Asn Gly Glu Val Pro
        195                 200                 205

Lys Val Pro Val Thr Phe Asp Asp Val Ala Val His Phe Ser Glu Gln
210                 215                 220

Glu Trp Gly Asn Leu Ser Glu Trp Gln Lys Glu Leu Tyr Lys Asn Val
225                 230                 235                 240

Met Arg Gly Asn Tyr Glu Ser Leu Val Ser Met Asp Tyr Ala Ile Ser
                245                 250                 255

Lys Pro Asp Leu Met Ser Gln Met Glu Arg Gly Glu Arg Pro Thr Met
            260                 265                 270

Gln Glu Gln Glu Asp Ser Glu Glu Gly Thr Pro Thr Asp Pro Ser
        275                 280                 285

Ala Ala His Asp Gly Ile Val Ile Lys Ile Glu Val Gln Thr Asn Asp
    290                 295                 300

Glu Gly Ser Glu Ser Leu Glu Thr Pro Glu Pro Leu Met Gly Gln Val
305                 310                 315                 320

Glu Glu His Gly Phe Gln Asp Ser Glu Leu Gly Xaa Pro Cys Gly Glu
                325                 330                 335

Gln Pro Asp Leu Asp Met Gln Gly Pro Glu Asn Thr Leu Glu Glu Ser
            340                 345                 350
```

```
Thr Glu Gly Ser Ser Glu Phe Ser Glu Leu Lys Gln Met Leu Val Gln
            355                 360                 365

Gln Arg Asn Cys Thr Glu Gly Ile Val Ile Lys Thr Glu Glu Gln Asp
        370                 375                 380

Glu Glu Glu Glu Glu Glu Glu Asp Glu Leu Pro Gln His Leu Gln
385                 390                 395                 400

Ser Leu Gly Gln Leu Ser Gly Arg Tyr Glu Ala Ser Met Tyr Gln Thr
                405                 410                 415

Pro Leu Pro Gly Glu Met Ser Pro Gly Glu Glu Ser Pro Pro
            420                 425                 430

Leu Gln Val Gly Asn Pro Ala Val Lys Arg Leu Ala Pro Ser Val His
            435                 440                 445

Gly Glu Arg Asp Leu Ser Glu Asn Arg Gly Gly Ser Ser Gln Gln Ser
450                 455                 460

Gly Asn Arg Arg Gly Glu Arg Pro Phe Thr Cys Met Glu Cys Gly Lys
465                 470                 475                 480

Ser Phe Arg Leu Lys Ile Asn Leu Ile Ile His His Gln Arg Asn Gln
                485                 490                 495

His Gln Gly Gly Gly Pro Thr Ser Ala Pro Asn Val Arg Ser Ala Phe
            500                 505                 510

Arg His Lys Gln Gln Leu Thr Leu His Gln Arg Ile His Arg Val Arg
            515                 520                 525

Gly Gly Cys Val Ser Pro Glu Arg Gly Pro Thr Phe Asn Pro Lys Xaa
            530                 535                 540

Ala Leu Lys Pro Arg Pro Lys Ser Pro Ser Ser Gly Ser Gly Gly Gly
545                 550                 555                 560

Gly Pro Lys Pro Tyr Lys Cys Pro Glu Cys Asp Ser Ser Phe Ser His
                565                 570                 575

Lys Ser Ser Leu Thr Lys His Gln Ile Thr His Thr Gly Glu Arg Pro
            580                 585                 590

Tyr Thr Cys Pro Glu Cys Lys Lys Ser Phe Arg Leu His Ile Ser Leu
            595                 600                 605

Val Ile His Gln Arg Val His Ala Gly Lys His Glu Val Ser Phe Ile
610                 615                 620

Cys Ser Leu Cys Gly Lys Ser Phe Ser Arg Pro Ser His Leu Leu Arg
625                 630                 635                 640

His Gln Arg Thr His Thr Gly Glu Arg Pro Phe Lys Cys Pro Glu Cys
            645                 650                 655

Glu Lys Ser Phe Ser Glu Lys Ser Lys Leu Thr Asn His Cys Arg Val
                660                 665                 670

His Ser Arg
    675
```

(2) INFORMATION FOR SEQ ID NO:10:

(i) SEQUENCE CHARACTERISTICS:
        (A) LENGTH: 9 amino acids
        (B) TYPE: amino acid
        (D) TOPOLOGY: linear (xi) SEQUENCE DESCRIPTION: SEQ ID NO:10:

```
Phe Glu Ile Glu Ala Arg Ala Gln Glu
1               5
```

(2) INFORMATION FOR SEQ ID NO:11:

```
    (i) SEQUENCE CHARACTERISTICS:
        (A) LENGTH: 9 amino acids
        (B) TYPE: amino acid
        (D) TOPOLOGY: linear (xi) SEQUENCE DESCRIPTION: SEQ ID NO:11:

Asp Gln Glu Asn Gln Asp Pro Arg Arg
1               5

(2) INFORMATION FOR SEQ ID NO:12:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (xi) SEQUENCE DESCRIPTION: SEQ ID NO:12:

GGAATTCATG AGCGATGGCT TTGGCAGTAG                                    30

(2) INFORMATION FOR SEQ ID NO:13:

(i) SEQUENCE CHARACTERISTICS:
        (A) LENGTH: 33 base pairs
        (B) TYPE: nucleic acid
        (C) STRANDEDNESS: single
        (D) TOPOLOGY: linear (xi) SEQUENCE DESCRIPTION: SEQ ID NO:13:

CGTCGACTCA GTTTGGTCCA CCGCCGAAGC CAG                                33

(2) INFORMATION FOR SEQ ID NO:14:

(i) SEQUENCE CHARACTERISTICS:
        (A) LENGTH: 32 base pairs
        (B) TYPE: nucleic acid
        (C) STRANDEDNESS: single
        (D) TOPOLOGY: linear (xi) SEQUENCE DESCRIPTION: SEQ ID NO:14:

GGAATTCATG GATGGCTCTC CCAGCACTGG TG                                 32

(2) INFORMATION FOR SEQ ID NO:15:

(i) SEQUENCE CHARACTERISTICS:
        (A) LENGTH: 31 base pairs
        (B) TYPE: nucleic acid
        (C) STRANDEDNESS: single
        (D) TOPOLOGY: linear (xi) SEQUENCE DESCRIPTION: SEQ ID NO:15:

GCAGCTGAGT GCTGGTGCTT AGTGTACCAC C                                  31

(2) INFORMATION FOR SEQ ID NO:16:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (xi) SEQUENCE DESCRIPTION: SEQ ID NO:16:

GGAATTCATG CCCAGCAACA GCATTGGC                                      28

(2) INFORMATION FOR SEQ ID NO:17:

(i) SEQUENCE CHARACTERISTICS:
```

```
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO:17:

GCAGCTGAGT ACTGGTGCTG GGTCCATCAC AAAAAC                                36

(2) INFORMATION FOR SEQ ID NO:18:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (xi) SEQUENCE DESCRIPTION: SEQ ID NO:18:

GGAATTCATG GATATCGACT GCCTA                                           25

(2) INFORMATION FOR SEQ ID NO:19:

(i) SEQUENCE CHARACTERISTICS:
        (A) LENGTH: 29 base pairs
        (B) TYPE: nucleic acid
        (C) STRANDEDNESS: single
        (D) TOPOLOGY: linear (xi) SEQUENCE DESCRIPTION: SEQ ID NO:19:

GCAGCTGAGT CTGGAGCTGG GTGCACCAT                                       29

(2) INFORMATION FOR SEQ ID NO:20:

(i) SEQUENCE CHARACTERISTICS:
        (A) LENGTH: 87 amino acids
        (B) TYPE: amino acid
        (D) TOPOLOGY: linear (xi) SEQUENCE DESCRIPTION: SEQ ID NO:20:

Asp Gly Ser Pro Ser Thr Gly Ala Gly Phe Gly Gly Ala Leu Asn Thr
1               5                   10                  15

Ser Ala Ser Phe Gly Ser Val Leu Asn Thr Ser Thr Gly Phe Gly Gly
            20                  25                  30

Ala Met Ser Thr Ser Ala Asp Phe Gly Gly Thr Leu Ser Thr Ser Val
        35                  40                  45

Cys Phe Gly Gly Ser Pro Gly Thr Ser Val Ser Phe Gly Ser Ala Leu
    50                  55                  60

Asn Thr Asn Ala Gly Tyr Gly Gly Ala Val Ser Thr Asn Thr Asp Phe
65                  70                  75                  80

Gly Gly Thr Leu Ser Thr Ser
                85

(2) INFORMATION FOR SEQ ID NO:21:

(i) SEQUENCE CHARACTERISTICS:
        (A) LENGTH: 72 amino acids
        (B) TYPE: amino acid
        (D) TOPOLOGY: linear (xi) SEQUENCE DESCRIPTION: SEQ ID NO:21:

Pro Ser Asn Ser Ile Gly Phe Gly Ala Ala Pro Ser Thr Ser Val Ser
1               5                   10                  15

Phe Gly Gly Ala His Gly Thr Ser Leu Cys Phe Gly Gly Ala Pro Ser
            20                  25                  30
```

```
Thr Ser Leu Cys Phe Gly Ser Ala Ser Asn Thr Asn Leu Cys Phe Gly
        35                  40                  45

Gly Pro Pro Ser Thr Ser Ala Cys Phe Ser Gly Ala Thr Ser Pro Ser
    50                  55                  60

Phe Cys Asp Gly Pro Ser Thr Ser
65                  70
```

(2) INFORMATION FOR SEQ ID NO:22:

(i) SEQUENCE CHARACTERISTICS:
        (A) LENGTH: 86 amino acids
        (B) TYPE: amino acid
        (D) TOPOLOGY: linear (xi) SEQUENCE DESCRIPTION: SEQ ID NO:22:

```
Ser Asp Gly Phe Gly Ser Arg Pro Asn Ala Ser Phe Asp Arg Gly Leu
1               5                   10                  15

Ser Thr Ile Ile Gly Phe Gly Ser Gly Ser Asn Thr Ser Thr Gly Phe
            20                  25                  30

Thr Gly Glu Pro Ser Thr Ser Thr Gly Phe Ser Gly Pro Ser Ser
        35                  40                  45

Ile Val Gly Phe Ser Gly Gly Pro Ser Thr Gly Val Gly Phe Cys Ser
    50                  55                  60

Gly Pro Ser Thr Ser Gly Phe Ser Gly Gly Pro Ser Thr Gly Ala Gly
65                  70                  75                  80

Phe Gly Gly Gly Pro Asn
                85
```

(2) INFORMATION FOR SEQ ID NO:23:

(i) SEQUENCE CHARACTERISTICS:
        (A) LENGTH: 3483 base pairs
        (B) TYPE: nucleic acid
        (C) STRANDEDNESS: single
        (D) TOPOLOGY: linear (ix) FEATURE:
        (A) NAME/KEY: CDS
        (B) LOCATION: 1..3481

(xi) SEQUENCE DESCRIPTION: SEQ ID NO:23:

```
ATG GAT ATT AAC TGC CTA ACA AGG GAA GAG TTG GGT GAT GAT GCG CAG        48
Met Asp Ile Asn Cys Leu Thr Arg Glu Glu Leu Gly Asp Asp Ala Gln
1               5                   10                  15

GCC TGG AGC AGA TTT TCC TTT GAA ATT GAA CCC AGA GCC CAA GAA AAT        96
Ala Trp Ser Arg Phe Ser Phe Glu Ile Glu Pro Arg Ala Gln Glu Asn
            20                  25                  30

GCA GAT CCT ACC ACT AAT GTC CTC TTC AAC CAA GGA GCT ACT ACC AGA       144
Ala Asp Pro Thr Thr Asn Val Leu Phe Asn Gln Gly Ala Thr Thr Arg
        35                  40                  45

AAT AGC TTT AGT GAT GGT GCT GGT ATT AGC TTT GGT GGT ATA ACC AAC       192
Asn Ser Phe Ser Asp Gly Ala Gly Ile Ser Phe Gly Gly Ile Thr Asn
    50                  55                  60

CCC AGT GGT GGC TTT GGT GGC ATA TCC AAC CCC AGT GGT GGC TTT GGT       240
Pro Ser Gly Gly Phe Gly Gly Ile Ser Asn Pro Ser Gly Gly Phe Gly
65                  70                  75                  80

GGC ATA TCC AAC CCC AGT GGT GGC TTT GGT GGC ATA TCC AAC CCC AGT       288
Gly Ile Ser Asn Pro Ser Gly Gly Phe Gly Gly Ile Ser Asn Pro Ser
                85                  90                  95

GGT GGC TTT GGT GGC ATA TCC AAC CCC AGT GGT GGC TTT GGT GGC ATA       336
Gly Gly Phe Gly Gly Ile Ser Asn Pro Ser Gly Gly Phe Gly Gly Ile
            100                 105                 110
```

-continued

| | |
|---|---|
| TCC AAC CCC AGT GGT GGC TTT GGT GGC ATA TCC AAC CCC AGT GGT GGC<br>Ser Asn Pro Ser Gly Gly Phe Gly Gly Ile Ser Asn Pro Ser Gly Gly<br>               115                      120                    125 | 384 |
| TTT GGT GGC ATA TCC AAC CCC AGT GGT GGC TTT GGT GGC ATA TCC AAC<br>Phe Gly Gly Ile Ser Asn Pro Ser Gly Gly Phe Gly Gly Ile Ser Asn<br> 130                      135                      140 | 432 |
| CCC AGT GGT GGC TTT GGT GGC ATA TCC AAC CCC AGT GGT GGC TTT GGT<br>Pro Ser Gly Gly Phe Gly Gly Ile Ser Asn Pro Ser Gly Gly Phe Gly<br>145                  150                      155                 160 | 480 |
| GGC ATA TCC AAT CCC AGT GGT GGC TTT GGT GGC ATA TCC AAT CCC AGT<br>Gly Ile Ser Asn Pro Ser Gly Gly Phe Gly Gly Ile Ser Asn Pro Ser<br>               165                      170                    175 | 528 |
| GGT GGC TTT GGG GGC AGA AAT AGC ATT ACT TTT GGG AGT GTA CCC AAC<br>Gly Gly Phe Gly Gly Arg Asn Ser Ile Thr Phe Gly Ser Val Pro Asn<br>        180                      185                    190 | 576 |
| ACC TCT GCC AAC TTC AGC AGT GCG CCG AGC ATT AGC TTT GGT GAC ACA<br>Thr Ser Ala Asn Phe Ser Ser Ala Pro Ser Ile Ser Phe Gly Asp Thr<br>           195                      200                    205 | 624 |
| CCT AAC ACT AGC ACC AGT TTC AGT GGC GGA GCC AAC AGT AGC TTC AGT<br>Pro Asn Thr Ser Thr Ser Phe Ser Gly Gly Ala Asn Ser Ser Phe Ser<br>       210                      215                    220 | 672 |
| GGC ACA CCT AGT ACT AGT GCC CCT TTC TGT AAC GCA GCA AGC ATT AGC<br>Gly Thr Pro Ser Thr Ser Ala Pro Phe Cys Asn Ala Ala Ser Ile Ser<br>225                  230                      235                 240 | 720 |
| TTT GGT GGT GCA CCC AGC ACT AGC ACC AGC TTT AGC ACA GCG AGC ATT<br>Phe Gly Gly Ala Pro Ser Thr Ser Thr Ser Phe Ser Thr Ala Ser Ile<br>               245                      250                    255 | 768 |
| AGC TTT GGT GGT GCA CCC AGC ACT AGC ACC AGC TTA AGC ACA GCA AGC<br>Ser Phe Gly Gly Ala Pro Ser Thr Ser Thr Ser Leu Ser Thr Ala Ser<br>        260                      265                    270 | 816 |
| ATT AGC TTT GGT GGT GCA CCT AGC ACT AGC ACC AGC TTC AGC ACA GCG<br>Ile Ser Phe Gly Gly Ala Pro Ser Thr Ser Thr Ser Phe Ser Thr Ala<br>       275                      280                    285 | 864 |
| AGC ATT AGC TTT GGT GGT GCA CCC AGC ACT AGC ACC AGC TTA AGC ACA<br>Ser Ile Ser Phe Gly Gly Ala Pro Ser Thr Ser Thr Ser Leu Ser Thr<br>       290                      295                    300 | 912 |
| GCA AGC ATT AGC TTT GGT GGT GCA CCC AGC ATT AAT AGT AGT AGT GGT<br>Ala Ser Ile Ser Phe Gly Gly Ala Pro Ser Ile Asn Ser Ser Ser Gly<br>305                  310                      315                 320 | 960 |
| GGA TCC AGC GTT AGC TTT GGT GGT GCT CCT ACC ACC AGT ACC AGT TTC<br>Gly Ser Ser Val Ser Phe Gly Gly Ala Pro Thr Thr Ser Thr Ser Phe<br>               325                      330                    335 | 1008 |
| AGT GGT GGA CCC TGT ATT AGT TTT GGT GGT GCA CCT TGT ACC ACT GCC<br>Ser Gly Gly Pro Cys Ile Ser Phe Gly Gly Ala Pro Cys Thr Thr Ala<br>        340                      345                    350 | 1056 |
| AGT ATT AGT GGT GGA GCC AGC TCT GGC TTT GGA AGC ACG CTT TGC AGT<br>Ser Ile Ser Gly Gly Ala Ser Ser Gly Phe Gly Ser Thr Leu Cys Ser<br>       355                      360                    365 | 1104 |
| ACC AAC CCT GGC TTT AGT GCA CTC AGC ACA AAC ACC AGC TTC GGC AGT<br>Thr Asn Pro Gly Phe Ser Ala Leu Ser Thr Asn Thr Ser Phe Gly Ser<br>       370                      375                    380 | 1152 |
| GCA CCA ACT ACA AGC ACT GTG TTC AGT GGT GCA GTT AGT ACC ACC ACT<br>Ala Pro Thr Thr Ser Thr Val Phe Ser Gly Ala Val Ser Thr Thr Thr<br>385                  390                      395                 400 | 1200 |
| GGC TTT GGA GGC ACA CTT AGC ACC AGT GTC TGC TTT GGT AGT TCT CCC<br>Gly Phe Gly Gly Thr Leu Ser Thr Ser Val Cys Phe Gly Ser Ser Pro<br>               405                      410                    415 | 1248 |
| TAC TCT GGC GCT GGC TTT GGA GGC ACA CTT AGT ACC AGT ATC TCC TTT<br>Tyr Ser Gly Ala Gly Phe Gly Gly Thr Leu Ser Thr Ser Ile Ser Phe | 1296 |

-continued

```
                        420                     425                     430
GGT GGT TCT CCT AGC ACC AAT ACT GGT TTT GGT GGT ACA CTC AGC ACC                  1344
Gly Gly Ser Pro Ser Thr Asn Thr Gly Phe Gly Gly Thr Leu Ser Thr
        435                     440                     445

AGT GTT TCC TTC GGT GCT TCT TCT AGC ACC AGC TCT GAC TTT GGT GGC                  1392
Ser Val Ser Phe Gly Ala Ser Ser Ser Thr Ser Ser Asp Phe Gly Gly
        450                     455                     460

ACA CTA AGC ACT AGT GTC AGC TTT GGT GGC TCT TCT GGT GCC AAT GCT                  1440
Thr Leu Ser Thr Ser Val Ser Phe Gly Gly Ser Ser Gly Ala Asn Ala
465                     470                     475                     480

GGC TTT GGC GGT ACA CTC AAC AGC AGT ACC AGC TTT GGC GGT GCC ATC                  1488
Gly Phe Gly Gly Thr Leu Asn Ser Ser Thr Ser Phe Gly Gly Ala Ile
                485                     490                     495

AGC ACC AGC ACT GGC TTT GGC AGT GCA CTC AAT AAC AGT GCC AAC TTT                  1536
Ser Thr Ser Thr Gly Phe Gly Ser Ala Leu Asn Asn Ser Ala Asn Phe
                500                     505                     510

GGT GGT GCC ATA AGT ACC AGC TTT AGT GGT GTA CTC AAT AGC AGT GCC                  1584
Gly Gly Ala Ile Ser Thr Ser Phe Ser Gly Val Leu Asn Ser Ser Ala
                515                     520                     525

AGC TTT GGT GGT GCC ATC AAC ACC AGT GCT GGC TTC GGC AGT ACA CTC                  1632
Ser Phe Gly Gly Ala Ile Asn Thr Ser Ala Gly Phe Gly Ser Thr Leu
        530                     535                     540

AAC AGC AGT GCC AGC TTT GGC AGT GCA CTC AGC ACC AGT GCC AGC TTT                  1680
Asn Ser Ser Ala Ser Phe Gly Ser Ala Leu Ser Thr Ser Ala Ser Phe
545                     550                     555                     560

GGT GGT GTA CTC AAT GGC AGA GCT GGC TTT GGT GGT GCC TTG AAC ACC                  1728
Gly Gly Val Leu Asn Gly Arg Ala Gly Phe Gly Gly Ala Leu Asn Thr
                565                     570                     575

AAT GCC ACC TTT GGT GGT GTA CTC AAT GGC AGC GCT GGC TTT GGT GGT                  1776
Asn Ala Thr Phe Gly Gly Val Leu Asn Gly Ser Ala Gly Phe Gly Gly
        580                     585                     590

GCC ATG AAC ACC AAT GCC ACC TTC GGT GGC GCA CTG AAT AGT AAT GCC                  1824
Ala Met Asn Thr Asn Ala Thr Phe Gly Gly Ala Leu Asn Ser Asn Ala
                595                     600                     605

GGC TTT GGC GGT GCC ATC AGT ACG AGT ACC AAC TTC GGT GGC GCA CTG                  1872
Gly Phe Gly Gly Ala Ile Ser Thr Ser Thr Asn Phe Gly Gly Ala Leu
        610                     615                     620

AAT AAC AGC GCT GGC TTT GGC GGC GCC ATG AAC ACT AGT GCC AGC TTC                  1920
Asn Asn Ser Ala Gly Phe Gly Gly Ala Met Asn Thr Ser Ala Ser Phe
625                     630                     635                     640

GGT GGT GTA CTG AAT AAC AGT GCT GGC TTT GGC GGT GCC ATC AAC ACC                  1968
Gly Gly Val Leu Asn Asn Ser Ala Gly Phe Gly Gly Ala Ile Asn Thr
                645                     650                     655

AGT GCC AAC TTT GGT GGC GCA CTG ACT AAC AGT GCT GGC TTT GGC GGT                  2016
Ser Ala Asn Phe Gly Gly Ala Leu Thr Asn Ser Ala Gly Phe Gly Gly
                660                     665                     670

GCC ATC AGT ACG AGT GCC AGC TTT GGT GGT GCA CTG AAT AAC AGT GCT                  2064
Ala Ile Ser Thr Ser Ala Ser Phe Gly Gly Ala Leu Asn Asn Ser Ala
        675                     680                     685

GGC TTT GGT GGT GCC ATC AGT ACG AGT GCC AGC TTT GGT GGT GCA CTG                  2112
Gly Phe Gly Gly Ala Ile Ser Thr Ser Ala Ser Phe Gly Gly Ala Leu
        690                     695                     700

AAT AAC AGT GCT GGC TTT GGC GGT GCC ATC AGC ACC AAT GCC AGC TTT                  2160
Asn Asn Ser Ala Gly Phe Gly Gly Ala Ile Ser Thr Asn Ala Ser Phe
705                     710                     715                     720

GGT GGA GCA ATC AGC AAC AGT CCT GAC TTT GGT GGT GCA TTC AGT ACC                  2208
Gly Gly Ala Ile Ser Asn Ser Pro Asp Phe Gly Gly Ala Phe Ser Thr
                725                     730                     735

AGT GTT GGC TTT GGT GGC ACA CTT AAT ACC ACT GAC TTT GGT AGT AAC                  2256
```

-continued

```
Ser Val Gly Phe Gly Gly Thr Leu Asn Thr Thr Asp Phe Gly Ser Asn
            740                 745                 750

CAT AGC AAC AGC ATT AGC TTT GGC AGT GCT CCC ACT ACC AGC GTT AGC       2304
His Ser Asn Ser Ile Ser Phe Gly Ser Ala Pro Thr Thr Ser Val Ser
            755                 760                 765

TTT GGT GGG TCT CAT AGC ACT AAC CTC TGT TTC GGT GGA GCA CCC AGC       2352
Phe Gly Gly Ser His Ser Thr Asn Leu Cys Phe Gly Gly Ala Pro Ser
770                 775                 780

ACC AGT CTC TGT TTT GGC AGT GCA TCT AAC ACC AAC CTA TGC TTT GGA       2400
Thr Ser Leu Cys Phe Gly Ser Ala Ser Asn Thr Asn Leu Cys Phe Gly
785                 790                 795                 800

GGC TCT AAC AGC ACC AAC TGC TTT AGT GGT GCT ACC AGT GCC AAT TTC       2448
Gly Ser Asn Ser Thr Asn Cys Phe Ser Gly Ala Thr Ser Ala Asn Phe
                805                 810                 815

AAT GAG GGG CAC AGC ATC AGT TTT GGG AAT GGG CTA AGT ACC AGT GCT       2496
Asn Glu Gly His Ser Ile Ser Phe Gly Asn Gly Leu Ser Thr Ser Ala
            820                 825                 830

GGA TTT GGA AAT GGG CTG GGC ACC AGT GCT GGC TTT GAC AGC AGC CTT       2544
Gly Phe Gly Asn Gly Leu Gly Thr Ser Ala Gly Phe Asp Ser Ser Leu
            835                 840                 845

GGT ACC AGC ACT GGC TTT GGT GGA AGC TTA GGC CCC AGT GCT AGC TTC       2592
Gly Thr Ser Thr Gly Phe Gly Gly Ser Leu Gly Pro Ser Ala Ser Phe
850                 855                 860

AAT GGT GGC CTG GGC ACC AGC ACT GGC TTT GGC GGT GGA CTA GGC ACC       2640
Asn Gly Gly Leu Gly Thr Ser Thr Gly Phe Gly Gly Gly Leu Gly Thr
865                 870                 875                 880

AGC ACG GAT TTC AGT GGT GGA CTA AAT CAT AAT GCT GAC TTC AAT GGA       2688
Ser Thr Asp Phe Ser Gly Gly Leu Asn His Asn Ala Asp Phe Asn Gly
                885                 890                 895

GGA CTG GGT AAC AGT GCT GGC TTC AAT GGT GGA CTA AAC ACT AAC ACT       2736
Gly Leu Gly Asn Ser Ala Gly Phe Asn Gly Gly Leu Asn Thr Asn Thr
            900                 905                 910

GAT TTT GGT GGT GAA CTG GGC ACT AGC GCT GGC TTT GGT GAT GGA CTG       2784
Asp Phe Gly Gly Glu Leu Gly Thr Ser Ala Gly Phe Gly Asp Gly Leu
            915                 920                 925

GGC AGC AGC ACC AGC TTT GGT GCA GGA CTG GTC ACT AGT GAT GGC TTT       2832
Gly Ser Ser Thr Ser Phe Gly Ala Gly Leu Val Thr Ser Asp Gly Phe
            930                 935                 940

GCT GGT AAC CTG GGC ACC AAT ACT GGT TTT GGT GGC ACA CTT GGC ACT       2880
Ala Gly Asn Leu Gly Thr Asn Thr Gly Phe Gly Gly Thr Leu Gly Thr
945                 950                 955                 960

GGT GCA GGC TTT AGT GTA AGC CTC AAC AAT GGC AAT GGC TTT GGC AAT       2928
Gly Ala Gly Phe Ser Val Ser Leu Asn Asn Gly Asn Gly Phe Gly Asn
                965                 970                 975

GGG CCT AAT GCC AGC TTC AAC AGA GGA CTG AAT ACC ATC ATT GGC TTT       2976
Gly Pro Asn Ala Ser Phe Asn Arg Gly Leu Asn Thr Ile Ile Gly Phe
            980                 985                 990

GGC AGT GGT TCC AAC ACC AGC AAT GGC TTT ACT GGT GAA CCC AAC ACT       3024
Gly Ser Gly Ser Asn Thr Ser Asn Gly Phe Thr Gly Glu Pro Asn Thr
            995                 1000                1005

GGC TCC AGC TTA GTA ATG GAC CCC AGT CTA TTG TTG GCT TTA GTG GT        3072
Gly Ser Ser Phe Ser Asn Gly Pro Ser Ser Ile Val Gly Phe Ser Gly
            1010                1015                1020

GGA CCA AGC ACT GGT GCT GGC TTC TGC AGT GGA CCA AGC ACT GGT GGC       3120
Gly Pro Ser Thr Gly Ala Gly Phe Cys Ser Gly Pro Ser Thr Gly Gly
1025                1030                1035                1040

TTC GGT GGT GGA CCA AGT ACA GGA CCT GGC TTC GGT GGA CCA AGT ACA       3168
Phe Gly Gly Gly Pro Ser Thr Gly Pro Gly Phe Gly Gly Pro Ser Thr
                1045                1050                1055
```

```
GGA CCT GGC TTC GGT GGA CCA AGC ACT GGA GGT GGC TTT GGA GGA CCA        3216
Gly Pro Gly Phe Gly Gly Pro Ser Thr Gly Gly Gly Phe Gly Gly Pro
         1060                1065                1070

AAT ACT GGA GGT GGC TTT GGA GGA CCA AGC ACT GGA GGT GGC TTT GGA        3264
Asn Thr Gly Gly Gly Phe Gly Gly Pro Ser Thr Gly Gly Gly Phe Gly
         1075                1080                1085

GGA CCA AGC ACT GGA GGT GGC TTC GGA GGA CCA AGC ACT GGA GGT GGC        3312
Gly Pro Ser Thr Gly Gly Gly Phe Gly Gly Pro Ser Thr Gly Gly Gly
         1090                1095                1100

TTC GGA GGA CCA AGC ACT GCA GCT GGC TTT GGT AGT GGA CTG AGC ACC        3360
Phe Gly Gly Pro Ser Thr Ala Ala Gly Phe Gly Ser Gly Leu Ser Thr
1105                1110                1115                1120

AGC ACT GGC TTT GGT GGT GGA CTG AAT ACC AGT GCT GGA TTC AGT GGT        3408
Ser Thr Gly Phe Gly Gly Gly Leu Asn Thr Ser Ala Gly Phe Ser Gly
         1125                1130                1135

GGA CCG CCA AGC ACC GGT ACT GGC TTT GGT GGT GGA GCC TCT AGC CAT        3456
Gly Pro Pro Ser Thr Gly Thr Gly Phe Gly Gly Gly Ala Ser Ser His
         1140                1145                1150

GGT GGC TGT GGC TTC CCT TAC GGC T AG                                   3483
Gly Gly Cys Gly Phe Pro Tyr Gly
         1155                116
```

(2) INFORMATION FOR SEQ ID NO:24:

(i) SEQUENCE CHARACTERISTICS:
        (A) LENGTH: 1160 amino acids
        (B) TYPE: amino acid
        (D) TOPOLOGY: linear (ii) MOLECULE TYPE: protein (xi) SEQUENCE DESCRIPTION: SEQ ID NO:24:

```
Met Asp Ile Asn Cys Leu Thr Arg Glu Glu Leu Gly Asp Asp Ala Gln
1               5                   10                  15

Ala Trp Ser Arg Phe Ser Phe Glu Ile Glu Pro Arg Ala Gln Glu Asn
            20                  25                  30

Ala Asp Pro Thr Thr Asn Val Leu Phe Asn Gln Gly Ala Thr Thr Arg
        35                  40                  45

Asn Ser Phe Ser Asp Gly Ala Gly Ile Ser Phe Gly Gly Ile Thr Asn
    50                  55                  60

Pro Ser Gly Gly Phe Gly Gly Ile Ser Asn Pro Ser Gly Gly Phe Gly
65                  70                  75                  80

Gly Ile Ser Asn Pro Ser Gly Gly Phe Gly Gly Ile Ser Asn Pro Ser
                85                  90                  95

Gly Gly Phe Gly Gly Ile Ser Asn Pro Ser Gly Gly Phe Gly Gly Ile
            100                 105                 110

Ser Asn Pro Ser Gly Gly Phe Gly Gly Ile Ser Asn Pro Ser Gly Gly
        115                 120                 125

Phe Gly Gly Ile Ser Asn Pro Ser Gly Gly Phe Gly Gly Ile Ser Asn
    130                 135                 140

Pro Ser Gly Gly Phe Gly Gly Ile Ser Asn Pro Ser Gly Gly Phe Gly
145                 150                 155                 160

Gly Ile Ser Asn Pro Ser Gly Gly Phe Gly Gly Ile Ser Asn Pro Ser
                165                 170                 175

Gly Gly Phe Gly Gly Arg Asn Ser Ile Thr Phe Gly Ser Val Pro Asn
            180                 185                 190

Thr Ser Ala Asn Phe Ser Ser Ala Pro Ser Ile Ser Phe Gly Asp Thr
        195                 200                 205
```

-continued

```
Pro Asn Thr Ser Thr Ser Phe Ser Gly Gly Ala Asn Ser Ser Phe Ser
    210                 215                 220

Gly Thr Pro Ser Thr Ser Ala Pro Phe Cys Asn Ala Ala Ser Ile Ser
225                 230                 235                 240

Phe Gly Gly Ala Pro Ser Thr Ser Thr Ser Phe Ser Thr Ala Ser Ile
                245                 250                 255

Ser Phe Gly Gly Ala Pro Ser Thr Ser Thr Ser Leu Ser Thr Ala Ser
            260                 265                 270

Ile Ser Phe Gly Gly Ala Pro Ser Thr Ser Thr Ser Phe Ser Thr Ala
        275                 280                 285

Ser Ile Ser Phe Gly Gly Ala Pro Ser Thr Ser Thr Ser Leu Ser Thr
    290                 295                 300

Ala Ser Ile Ser Phe Gly Gly Ala Pro Ser Ile Asn Ser Ser Ser Gly
305                 310                 315                 320

Gly Ser Ser Val Ser Phe Gly Gly Ala Pro Thr Thr Ser Thr Ser Phe
                325                 330                 335

Ser Gly Gly Pro Cys Ile Ser Phe Gly Gly Ala Pro Cys Thr Thr Ala
            340                 345                 350

Ser Ile Ser Gly Gly Ala Ser Ser Gly Phe Gly Ser Thr Leu Cys Ser
        355                 360                 365

Thr Asn Pro Gly Phe Ser Ala Leu Ser Thr Asn Thr Ser Phe Gly Ser
    370                 375                 380

Ala Pro Thr Thr Ser Thr Val Phe Ser Gly Ala Val Ser Thr Thr Thr
385                 390                 395                 400

Gly Phe Gly Gly Thr Leu Ser Thr Ser Val Cys Phe Gly Ser Ser Pro
                405                 410                 415

Tyr Ser Gly Ala Gly Phe Gly Gly Thr Leu Ser Thr Ser Ile Ser Phe
            420                 425                 430

Gly Gly Ser Pro Ser Thr Asn Thr Gly Phe Gly Thr Leu Ser Thr
        435                 440                 445

Ser Val Ser Phe Gly Ala Ser Ser Ser Thr Ser Ser Asp Phe Gly Gly
    450                 455                 460

Thr Leu Ser Thr Ser Val Ser Phe Gly Gly Ser Ser Gly Ala Asn Ala
465                 470                 475                 480

Gly Phe Gly Gly Thr Leu Asn Ser Ser Thr Ser Phe Gly Ala Ile
                485                 490                 495

Ser Thr Ser Thr Gly Phe Gly Ser Ala Leu Asn Asn Ser Ala Asn Phe
            500                 505                 510

Gly Gly Ala Ile Ser Thr Ser Phe Ser Gly Val Leu Asn Ser Ser Ala
        515                 520                 525

Ser Phe Gly Gly Ala Ile Asn Thr Ser Ala Gly Phe Gly Ser Thr Leu
    530                 535                 540

Asn Ser Ser Ala Ser Phe Gly Ser Ala Leu Ser Thr Ser Ala Ser Phe
545                 550                 555                 560

Gly Gly Val Leu Asn Gly Arg Ala Gly Phe Gly Gly Ala Leu Asn Thr
                565                 570                 575

Asn Ala Thr Phe Gly Gly Val Leu Asn Gly Ser Ala Gly Phe Gly Gly
            580                 585                 590

Ala Met Asn Thr Asn Ala Thr Phe Gly Gly Ala Leu Asn Ser Asn Ala
        595                 600                 605

Gly Phe Gly Gly Ala Ile Ser Thr Ser Thr Asn Phe Gly Gly Ala Leu
    610                 615                 620

Asn Asn Ser Ala Gly Phe Gly Gly Ala Met Asn Thr Ser Ala Ser Phe
```

-continued

```
                625                 630                 635                 640
Gly Gly Val Leu Asn Asn Ser Ala Gly Phe Gly Gly Ala Ile Asn Thr
                    645                 650                 655
Ser Ala Asn Phe Gly Gly Ala Leu Thr Asn Ser Ala Gly Phe Gly Gly
                660                 665                 670
Ala Ile Ser Thr Ser Ala Ser Phe Gly Gly Ala Leu Asn Asn Ser Ala
            675                 680                 685
Gly Phe Gly Gly Ala Ile Ser Thr Ser Ala Ser Phe Gly Gly Ala Leu
        690                 695                 700
Asn Asn Ser Ala Gly Phe Gly Gly Ala Ile Ser Thr Asn Ala Ser Phe
705                 710                 715                 720
Gly Gly Ala Ile Ser Asn Ser Pro Asp Phe Gly Gly Ala Phe Ser Thr
                    725                 730                 735
Ser Val Gly Phe Gly Gly Thr Leu Asn Thr Thr Asp Phe Gly Ser Asn
                740                 745                 750
His Ser Asn Ser Ile Ser Phe Gly Ser Ala Pro Thr Thr Ser Val Ser
            755                 760                 765
Phe Gly Gly Ser His Ser Thr Asn Leu Cys Phe Gly Gly Ala Pro Ser
        770                 775                 780
Thr Ser Leu Cys Phe Gly Ser Ala Ser Asn Thr Asn Leu Cys Phe Gly
785                 790                 795                 800
Gly Ser Asn Ser Thr Asn Cys Phe Ser Gly Ala Thr Ser Ala Asn Phe
                    805                 810                 815
Asn Glu Gly His Ser Ile Ser Phe Gly Asn Gly Leu Ser Thr Ser Ala
                820                 825                 830
Gly Phe Gly Asn Gly Leu Gly Thr Ser Ala Gly Phe Asp Ser Ser Leu
            835                 840                 845
Gly Thr Ser Thr Gly Phe Gly Gly Ser Leu Gly Pro Ser Ala Ser Phe
        850                 855                 860
Asn Gly Gly Leu Gly Thr Ser Thr Gly Phe Gly Gly Leu Gly Thr
865                 870                 875                 880
Ser Thr Asp Phe Ser Gly Gly Leu Asn His Asn Ala Asp Phe Asn Gly
                    885                 890                 895
Gly Leu Gly Asn Ser Ala Gly Phe Asn Gly Gly Leu Asn Thr Asn Thr
                900                 905                 910
Asp Phe Gly Gly Glu Leu Gly Thr Ser Ala Gly Phe Gly Asp Gly Leu
            915                 920                 925
Gly Ser Ser Thr Ser Phe Gly Ala Gly Leu Val Thr Ser Asp Gly Phe
        930                 935                 940
Ala Gly Asn Leu Gly Thr Asn Thr Gly Phe Gly Gly Thr Leu Gly Thr
945                 950                 955                 960
Gly Ala Gly Phe Ser Val Ser Leu Asn Asn Gly Asn Gly Phe Gly Asn
                    965                 970                 975
Gly Pro Asn Ala Ser Phe Asn Arg Gly Leu Asn Thr Ile Ile Gly Phe
                980                 985                 990
Gly Ser Gly Ser Asn Thr Ser Asn Gly Phe Thr Gly Glu Pro Asn Thr
            995                 1000                1005
Gly Ser Ser Phe Ser Asn Gly Pro Ser Ser Ile Val Gly Phe Ser Gly
        1010                1015                1020
Gly Pro Ser Thr Gly Ala Gly Phe Cys Ser Gly Pro Ser Thr Gly Gly
1025                1030                1035                1040
Phe Gly Gly Gly Pro Ser Thr Gly Pro Gly Phe Gly Gly Pro Ser Thr
                    1045                1050                1055
```

```
Gly Pro Gly Phe Gly Gly Pro Ser Thr Gly Gly Phe Gly Gly Pro
            1060                1065                1070

Asn Thr Gly Gly Gly Phe Gly Gly Pro Ser Thr Gly Gly Phe Gly
            1075                1080                1085

Gly Pro Ser Thr Gly Gly Phe Gly Gly Pro Ser Thr Gly Gly Gly
            1090                1095                1100

Phe Gly Gly Pro Ser Thr Ala Ala Gly Phe Gly Ser Gly Leu Ser Thr
1105                1110                1115                1120

Ser Thr Gly Phe Gly Gly Gly Leu Asn Thr Ser Ala Gly Phe Ser Gly
                1125                1130                1135

Gly Pro Pro Ser Thr Gly Thr Gly Phe Gly Gly Ala Ser Ser His
                1140                1145                1150

Gly Gly Cys Gly Phe Pro Tyr Gly
            1155                1160

(2) INFORMATION FOR SEQ ID NO:25:

(i) SEQUENCE CHARACTERISTICS:
        (A) LENGTH: 9 amino acids
        (B) TYPE: amino acid
        (D) TOPOLOGY: linear (xi) SEQUENCE DESCRIPTION: SEQ ID NO:25:

Phe Asp Arg Gly Leu Ser Thr Ile Ile
1               5

(2) INFORMATION FOR SEQ ID NO:26:

(i) SEQUENCE CHARACTERISTICS:
        (A) LENGTH: 9 amino acids
        (B) TYPE: amino acid
        (D) TOPOLOGY: linear (xi) SEQUENCE DESCRIPTION: SEQ ID NO:26:

Thr Ile Ile Gly Phe Gly Ser Gly Ser
1               5

(2) INFORMATION FOR SEQ ID NO:27:

(i) SEQUENCE CHARACTERISTICS:
        (A) LENGTH: 15 amino acids
        (B) TYPE: amino acid
        (D) TOPOLOGY: linear (xi) SEQUENCE DESCRIPTION: SEQ ID NO:27:

Phe Asp Arg Gly Leu Ser Thr Ile Ile Gly Phe Gly Ser Gly Ser
1               5                   10                  15

(2) INFORMATION FOR SEQ ID NO:28:

(i) SEQUENCE CHARACTERISTICS:
        (A) LENGTH: 9 amino acids
        (B) TYPE: amino acid
        (D) TOPOLOGY: linear (xi) SEQUENCE DESCRIPTION: SEQ ID NO:28:

Ser Ile Val Gly Phe Ser Gly Gly Pro
1               5

(2) INFORMATION FOR SEQ ID NO:29:

(i) SEQUENCE CHARACTERISTICS:
        (A) LENGTH: 9 amino acids
```

(B) TYPE: amino acid
        (D) TOPOLOGY: linear (xi) SEQUENCE DESCRIPTION: SEQ ID NO:29:

Phe Asn Arg Gly Leu Asn Thr Ile Ile
1               5

(2) INFORMATION FOR SEQ ID NO:30:

(i) SEQUENCE CHARACTERISTICS:
        (A) LENGTH: 15 amino acids
        (B) TYPE: amino acid
        (D) TOPOLOGY: linear (xi) SEQUENCE DESCRIPTION: SEQ ID NO:30:

Phe Asn Arg Gly Leu Asn Thr Ile Ile Gly Phe Gly Ser Gly Ser
1               5                   10                  15

(2) INFORMATION FOR SEQ ID NO:31:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (xi) SEQUENCE DESCRIPTION: SEQ ID NO:31:

AAGGATCCAA TGGGCCTAAT GCCAGCT                                    27

(2) INFORMATION FOR SEQ ID NO:32:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (xi) SEQUENCE DESCRIPTION: SEQ ID NO:32:

ATCTCGAGTG TACTTGGTCC ACCACCGA                                   28

(2) INFORMATION FOR SEQ ID NO:33:

(i) SEQUENCE CHARACTERISTICS:
        (A) LENGTH: 29 base pairs
        (B) TYPE: nucleic acid
        (C) STRANDEDNESS: single
        (D) TOPOLOGY: linear (xi) SEQUENCE DESCRIPTION: SEQ ID NO:33:

TTGGATCCAC ATGGATATTA ACTGCCTAA                                  29

(2) INFORMATION FOR SEQ ID NO:34:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (xi) SEQUENCE DESCRIPTION: SEQ ID NO:34:

CCAGAATTCA AGCTATTTCT GGTAGTAGCT                                 30

(2) INFORMATION FOR SEQ ID NO:35:

(i) SEQUENCE CHARACTERISTICS:
        (A) LENGTH: 54 amino acids
        (B) TYPE: amino acid (D) TOPOLOGY: linear (xi) SEQUENCE DESCRIPTION: SEQ ID NO:35:

Met Asp Ile Asn Cys Leu Thr Arg Glu Glu Leu Gly Asp Asp Ala Gln
1               5                   10                  15

Ala Trp Ser Arg Phe Ser Phe Glu Ile Glu Pro Arg Ala Gln Glu Asn
                20                  25                  30

Ala Asp Pro Thr Thr Asn Val Leu Phe Asn Gln Gly Ala Thr Thr Arg
            35                  40                  45

Asn Ser Phe Ser Asp Gly
            50

(2) INFORMATION FOR SEQ ID NO:36:

(i) SEQUENCE CHARACTERISTICS:
        (A) LENGTH: 54 amino acids
        (B) TYPE: amino acid
        (D) TOPOLOGY: linear (xi) SEQUENCE DESCRIPTION: SEQ ID NO:36:

Met Asp Ile Asp Cys Leu Thr Arg Glu Glu Leu Gly Asp Asp Ser Gln
1               5                   10                  15

Ala Trp Ser Arg Phe Ser Phe Glu Ile Glu Ala Arg Ala Gln Glu Asn
                20                  25                  30

Ala Asp Ala Ser Thr Asn Val Asn Phe Ser Arg Gly Ala Ser Thr Arg
            35                  40                  45

Ala Gly Phe Ser Asp Arg
            50

(2) INFORMATION FOR SEQ ID NO:37:

(i) SEQUENCE CHARACTERISTICS:
        (A) LENGTH: 82 amino acids
        (B) TYPE: amino acid
        (D) TOPOLOGY: linear (xi) SEQUENCE DESCRIPTION: SEQ ID NO:37:

Asn Gly Phe Gly Asn Gly Pro Asn Ala Ser Phe Asn Arg Gly Leu Asn
1               5                   10                  15

Thr Ile Ile Gly Phe Gly Ser Gly Ser Asn Thr Ser Asn Gly Phe Thr
                20                  25                  30

Gly Glu Pro Asn Thr Gly Ser Ser Phe Ser Asn Gly Pro Ser Ser Ile
            35                  40                  45

Val Gly Phe Ser Gly Gly Pro Ser Thr Gly Ala Gly Phe Cys Ser Gly
            50              55                  60

Pro Ser Thr Gly Gly Phe Gly Gly Gly Pro Ser Thr Gly Pro Gly Phe
65                  70                  75                  80

Gly Gly (2) INFORMATION FOR SEQ ID NO:38:

(i) SEQUENCE CHARACTERISTICS:
        (A) LENGTH: 82 amino acids
        (B) TYPE: amino acid
        (D) TOPOLOGY: linear (xi) SEQUENCE DESCRIPTION: SEQ ID NO:38:

Asp Gly Phe Gly Ser Arg Pro Asn Ala Ser Phe Asp Arg Gly Leu Ser
1               5                   10                  15

Thr Ile Ile Gly Phe Gly Ser Gly Ser Asn Thr Ser Thr Gly Phe Thr

```
            20                  25                  30
Gly Glu Pro Ser Thr Ser Thr Gly Phe Ser Ser Gly Pro Ser Ser Ile
            35                  40                  45

Val Gly Phe Ser Gly Gly Pro Ser Thr Gly Val Gly Phe Cys Ser Gly
 50                  55                  60

Pro Ser Thr Ser Gly Phe Ser Gly Gly Pro Ser Thr Gly Ala Gly Phe
 65                  70                  75                  80

Gly Gly (2) INFORMATION FOR SEQ ID NO:39:

(i) SEQUENCE CHARACTERISTICS:
        (A) LENGTH: 150 amino acids
        (B) TYPE: amino acid
        (D) TOPOLOGY: linear (xi) SEQUENCE DESCRIPTION: SEQ ID NO:39:

Phe Gly Val Ala Pro Ser Thr Ser Ala Ser Phe Ser Asn Thr Ala Ser
 1               5                  10                  15

Ile Ser Phe Gly Gly Thr Leu Ser Thr Ser Ser Ser Phe Ser Ser Ala
            20                  25                  30

Ala Ser Ile Ser Phe Gly Cys Ala His Ser Thr Ser Thr Ser Phe Ser
            35                  40                  45

Ser Glu Ala Ser Ile Ser Phe Gly Gly Met Pro Cys Thr Ser Ala Ser
 50                  55                  60

Phe Ser Gly Gly Val Ser Ser Phe Ser Gly Pro Leu Ser Thr Ser
 65                  70                  75                  80

Ala Thr Phe Ser Gly Gly Ala Ser Ser Gly Phe Gly Gly Thr Leu Ser
            85                  90                  95

Thr Thr Ala Gly Phe Ser Gly Val Leu Ser Thr Ser Thr Ser Phe Gly
            100                 105                 110

Ser Ala Pro Thr Thr Ser Thr Val Phe Ser Ser Ala Leu Ser Thr Ser
            115                 120                 125

Thr Gly Phe Gly Gly Ile Leu Ser Thr Ser Val Cys Phe Gly Gly Ser
            130                 135                 140

Pro Ser Ser Ser Gly Ser
145                 150

(2) INFORMATION FOR SEQ ID NO:40:

(i) SEQUENCE CHARACTERISTICS:
        (A) LENGTH: 149 amino acids
        (B) TYPE: amino acid
        (D) TOPOLOGY: linear (xi) SEQUENCE DESCRIPTION: SEQ ID NO:40:

Phe Gly Ser Val Pro Asn Thr Ser Ala Asn Phe Ser Ser Ala Pro Ser
 1               5                  10                  15

Ile Ser Phe Gly Asp Thr Pro Asn Thr Ser Thr Ser Phe Ser Gly Gly
            20                  25                  30

Ala Asn Ser Ser Phe Ser Gly Thr Pro Ser Thr Ser Ala Pro Phe Cys
            35                  40                  45

Asn Ala Ala Ser Ile Ser Phe Gly Gly Ala Pro Ser Thr Ser Thr Ser
 50                  55                  60

Phe Ser Thr Ala Ser Ile Ser Phe Gly Gly Ala Pro Ser Thr Ser Thr
 65                  70                  75                  80

Ser Leu Ser Thr Ala Ser Ile Ser Phe Gly Gly Ala Pro Ser Thr Ser
```

-continued

```
                  85                  90                  95
Thr Ser Phe Ser Thr Ala Ser Ile Ser Phe Gly Gly Ala Pro Ser Thr
            100                 105                 110

Ser Thr Ser Leu Ser Thr Ala Ser Ile Ser Phe Gly Gly Ala Pro Ser
            115                 120                 125

Ile Asn Ser Ser Ser Gly Gly Ser Ser Val Ser Phe Gly Gly Ala Pro
    130                 135                 140

Thr Thr Ser Thr Ser
145

(2) INFORMATION FOR SEQ ID NO:41:

(i) SEQUENCE CHARACTERISTICS:
        (A) LENGTH: 145 amino acids
        (B) TYPE: amino acid
        (D) TOPOLOGY: linear (xi) SEQUENCE DESCRIPTION: SEQ ID NO:41:

Pro Ser Ser Thr Ser Thr Ser Pro Ser Ser Thr Ser Thr Ser Ser Ser
1               5                   10                  15

Ser Thr Ser Thr Ser Ser Ser Ser Thr Ser Thr Ser Ser Ser Ser Thr
            20                  25                  30

Ser Thr Ser Pro Ser Ser Thr Ser Thr Ser Ser Ser Leu Thr Ser Thr
            35                  40                  45

Ser Ser Ser Ser Thr Ser Thr Ser Gln Ser Ser Thr Ser Thr Ser Ser
    50                  55                  60

Ser Ser Thr Ser Thr Ser Pro Ser Ser Thr Ser Thr Ser Ser Ser Ser
65                  70                  75                  80

Thr Ser Thr Ser Pro Ser Ser Lys Ser Thr Ser Ala Ser Ser Thr Ser
            85                  90                  95

Thr Ser Ser Tyr Ser Thr Ser Thr Ser Pro Ser Leu Thr Ser Ser Ser
            100                 105                 110

Pro Thr Leu Ala Ser Thr Ser Pro Ser Ser Thr Ser Ile Ser Ser Thr
            115                 120                 125

Phe Thr Asp Ser Thr Ser Ser Leu Gly Ser Ser Ile Ala Ser Ser Ser
    130                 135                 140

Thr
145
```

TROPHININ, TROPHININ-ASSISTING PROTEINS AND METHODS TO INHIBIT IMPLANTATION

This application is a continuation-in-part of Ser. No. 08/439,818, filed May 12, 1995 now U.S. Pat. No. 5,654,145, which is a continuation-in-part of Ser. No. 08/317,522, filed Oct. 4, 1994 now U.S. Pat. No. 5,599,918.

This work was supported by grant number DK37016 and HD 34108 awarded by the National Institutes of Health. The United States government has certain rights in this invention.

BACKGROUND OF THE INVENTION

This invention relates generally to the fields of biochemistry and molecular biology and more specifically to cell adhesion molecules and embryo implantation.

The early stages of pregnancy involve fertilization of an egg by a sperm, followed by cell division and implantation of the embryo into the uterine cell wall. The inability of the embryo to properly implant in the uterus is a significant cause of pregnancy failure following in vitro or in vivo fertilization. The early events of implantation are characterized by an initial attachment of the embryo's external cell lining (trophoblast layer) to the cells lining the uterus (endometrial epithelium), followed by or in parallel with adhesion of these two cell types. The molecular events involved in the early steps of implantation are not well understood.

Embryo attachment and adhesion to the uterine endometrium is unusual in that cells from these two sources adhere at their apical surfaces. In contrast, most other epithelial cell interactions adhere at their basal and lateral cell surfaces. The unique ability of trophoblast and endometrial cells to adhere may result from apical display of adhesion molecules normally located at basal and lateral surfaces. Alternatively, adhesion of these cell types during implantation may be mediated by unique cell surface molecules.

Recent experiments suggest that certain endometrial tumor cell lines express characteristics associated with implantation-receptive endometrial tissue. In these experiments, trophoblast cells derived from germ cell tumors adhered to monolayers of endometrial adenocarcinoma cells via their apical cell surfaces. Morphological analysis of the adhering cell surfaces showed characteristics in common with early stage implantation. However, the molecules involved in the critical early adhesion step of embryo implantation were not identified. Thus, a need exists to identify the molecules responsible for adhesion of the embryo to the uterine lining and to exploit such molecules for purposes of inhibiting or augmenting embryo implantation. The present invention satisfies this need and provides related advantages as well.

SUMMARY OF THE INVENTION

The present invention provides a method to vaccinate an individual to prevent pregnancy by administering an effective dose of a trophinin vaccine, which can elicit an immune response against trophinin in the individual. The method utilizes mammalian trophinin polypeptides for immunization including trophinin obtained from a human or mouse, or a peptide fragment of trophinin. The invention also utilizes an adjuvant or a carrier protein to enhance the immune response to the trophinin vaccine.

The method further provides a nucleic acid molecule that encodes trophinin or fragments thereof as the trophinin vaccine, which is expressed by cells in the individual administered the vaccine. The nucleic acid encoding trophinin vaccine can further contain nucleic acid encoding a trophinin-assisting protein, which can be expressed with that of trophinin in cells of the individual administered the vaccine.

The invention also provides a method to prevent adhesion between a trophoblast cell and a uterine epithelial cell in an individual by administering a trophinin vaccine containing full length trophinin or a peptide fragment thereof. The invention further provides mammalian trophinin peptide fragments and antibodies to the fragments. The invention also provides nucleic acid molecules encoding a mammalian trophinin or a peptide fragment thereof as well as nucleic acid probes that can specifically hybridize under relatively stringent conditions to the encoding nucleic acid molecules.

BRIEF DESCRIPTION OF FIGURES

FIG. 1 shows the amino acid sequence of mouse trophinin (SEQ ID NO: 24). The lettering at left indicates the amino acid position. The cytoplasmic domain at the amino terminus is shown in italics while the cell surface domain is shown in boldface. The sequence is presented in a form that identifies the individual tandem repeats beginning at position 51 to 1156 (see, also, SEQ ID NO: 3, showing the tandem repeats in human trophinin; amino acid positions 69 to 749 of SEQ ID NO: 1). Single-letter amino acid symbols are shown.

FIGS. 2A and 2B present an amino acid sequence alignment between a portion of mouse (M) and human (H) trophinin. A vertical line indicates identity of amino acid residues at each position while a colon indicates a conservative substitution. Single-letter amino acid symbols are shown.

FIG. 2A shows an alignment of the amino terminus of mouse (SEQ ID NO: 35) and human trophinin (SEQ ID NO: 36) from position 1 to 54. Serine and threonine residues in the context of potential casein kinase II and protein kinase C phosphorylation sites are shown by bold and by bold/underline, respectively.

FIG. 2B presents an alignment between the mouse trophinin (SEQ ID NO: 37) cell surface domain and the third external membrane domain of human trophinin (SEQ ID NO: 38). Potential N-glycosylation sites are shown in italics. Three epitopes recognized by anti-GST553 antibody in human trophinin are underlined.

DETAILED DESCRIPTION OF THE INVENTION

Figure 3:
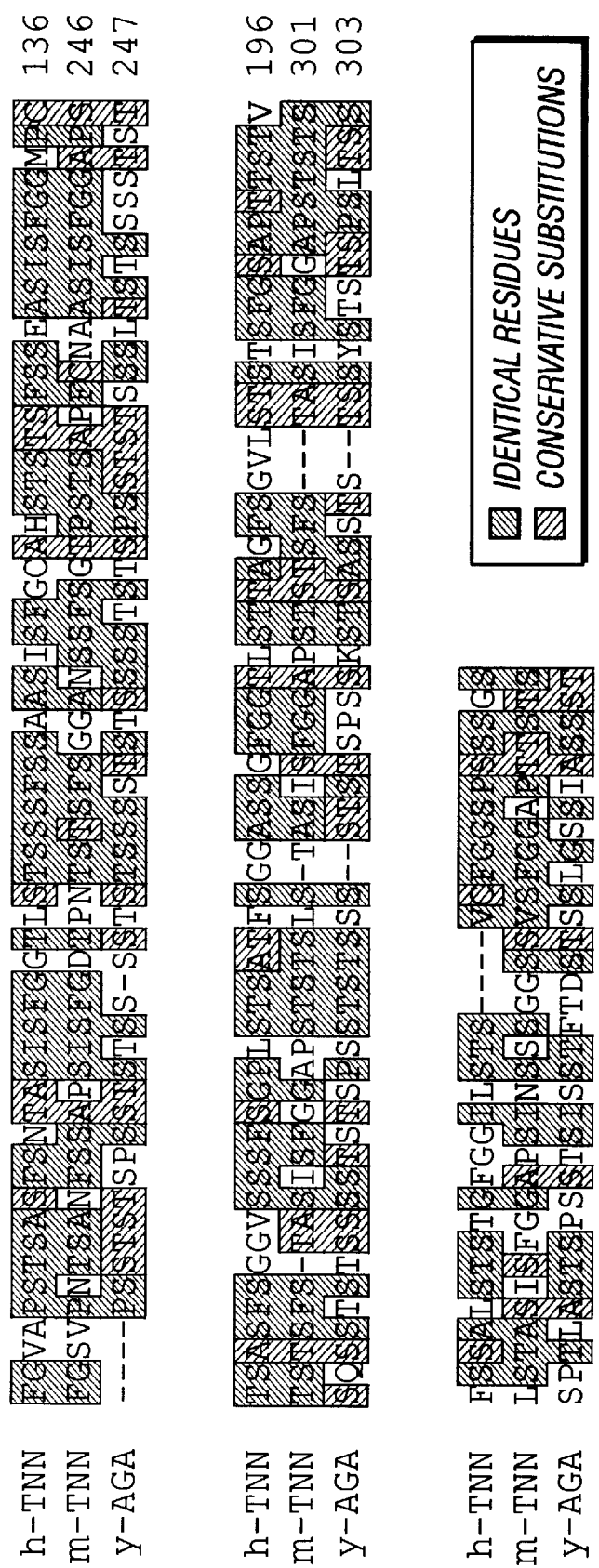
FIG. 3 shows alignment of a conserved region of mouse (SEQ ID NO: 40) and human trophinin (SEQ ID NO: 39) and the a-agglutinin subunit of the yeast AGA1 protein (SEQ ID NO: 41). Single-letter amino acid symbols are shown. Numbers indicate the position of the amino acids in human trophinin (h-TNN), mouse trophinin (m-TNN) and yeast a-agglutinin subunit of the AGA1 protein (Y-AGA). Identical residues are outlined in black while conservative substitutions are outlined in grey.

The present invention provides a method to inhibit pregnancy in an individual by administering an immunogenic trophinin vaccine, which elicits an immune response that blocks embryo implantation. The invention also provides a method to inhibit cell adhesion between a trophoblast cell and a uterine epithelial cell by administering a trophinin vaccine, which elicits an immune response to trophinin expressed by the cells. As used herein, the term "trophinin vaccine" means an immunogen containing a trophinin protein, polypeptide or peptide derived therefrom. The immunogen has one or more trophinin epitopes detected by the immune system. Examples of a trophinin vaccine include the human trophinin amino acid sequence shown in SEQ ID NO: 2 and the mouse trophinin sequence shown in SEQ ID NO: 24. A trophinin vaccine can also be a nucleic acid molecule encoding trophinin.

Trophinin is a cell membrane adhesion molecule that is expressed in the embryo and in the uterine cell lining and plays a critical role in implantation (International Patent No. WO 96/10414, Apr. 11, 1996; Fukuda et al., *Genes Devel.* 9:1199 (1995), U.S. Pat. No. 5,599,918, issued Feb. 4, 1997, each of which is incorporated herein by reference). A trophinin vaccine is characterized in that it can stimulate an immune response when administered to an individual such as a human, mouse, dog or other mammal. When administered to an individual, the trophinin vaccine can elicit antibodies that bind to trophinin in the individual, thereby interfering with implantation and inhibiting pregnancy.

Trophinin provides particular advantages over other anti-pregnancy vaccines that are based on hormones relevant to fertility and pregnancy. For example, an anti-human chorionic gonadotrophin (HCG) vaccine that blocks pregnancy is limited by the fact that HCG can be found in normal organs of the mother, such as the ovary (Drinhofer and Berger, *Int. Arch. Allergy Immunol.*, 108:350,352 (1995)). Thus, concerns have been raised that anti-pregnancy vaccines directed to peptide hormones may lead to unwanted autoimmune reactions (see id.). In contrast, trophinin is more limited in tissue expression than is HCG. Besides the embryo, trophinin expression is virtually absent from the adult female. Trophinin is detectable mainly in one adult organ, the uterus. Furthermore, expression by the uterus is very temporary, lasting only a few days of each menstrual cycle. Thus, trophinin provides the advantage that an anti-trophinin immune response will be less toxic than would other prior art anti-pregnancy vaccines directed to peptide hormones.

As used herein, the terms "protein" and "polypeptide" are used in their broadest sense to mean a sequence of amino acids, which can be encoded by a cellular gene or by a recombinant nucleic acid sequence or can be chemically synthesized. A protein or polypeptide can be a complete, full length gene product, which can be a core protein having no amino acid modifications or can be a post-translationally modified form of a protein such as a phosphoprotein, glycoprotein, proteoglycan, lipoprotein or nucleoprotein.

As used herein, the term "peptide" or "peptide fragment" means a fragment of a full length protein. As used herein, a peptide can be only a few amino acids in length or can be hundreds of amino acids in length, provided the peptide is smaller than the full length sequence encoded by the gene.

Trophinin is a cell membrane protein that is characterized primarily by its ability to effect cell adhesion. It is recognized that the ability of trophinin to effect cell adhesion can be due to a portion of the full length protein. For example, as discussed below, greater than 90% of trophinin is composed of a repeating sequence primarily decapeptide in character that can be involved in binding to another trophinin molecule. Thus, a polypeptide that contains only a portion of the full length trophinin protein can be useful for mediating cell adhesion or for eliciting an immune response to trophinin.

As used herein, the term "trophinin" means the full length trophinin protein or a peptide fragment derived therefrom. A trophinin vaccine of the present invention can also be a active fragment of the trophinin, such as an external membrane domain of trophinin. The human trophinin protein has three external membrane domains that are hydrophilic in character. An external domain can be expressed, for example, as a fusion protein to glutathionine-S-transferase (GST) and used to elicit antibodies that react with trophinin expressed on the surface of cells (Example I). The first trophinin external membrane domain, referring to human trophinin protein (SEQ ID NO: 2), is located from amino acid position 278 to 364 (SEQ ID NO: 20), the second from position 441 to 512 (SEQ ID NO: 21) and the third from position 634 to 719 (SEQ ID NO: 22).

A trophinin vaccine of the present invention includes one or more trophinin epitopes that can elicit an anti-trophinin antibody. A trophinin epitope can be derived from human trophinin and can have, for example, the amino acid sequence Phe-Asp-Arg-Gly-Leu-Ser-Thr-Ile-Ile (SEQ ID NO: 25), Thr-Ile-Ile-Gly-Phe-Gly-Ser-Gly-Ser (SEQ ID NO: 26), Phe-Asp-Arg-Gly-Leu-Ser-Thr-Ile-Ile-Gly-Phe-Gly-Ser-Gly-Ser (SEQ ID NO: 27) or Ser-Ile-Val-Gly-Phe-Ser-Gly-Gly-Pro (SEQ ID NO: 28). Alternatively, the epitope can be derived from a non-human trophinin such as from mouse trophinin, for example, the sequence Phe-Asn-Arg-Gly-Leu-Asn-Thr-Ile-Ile (SEQ ID NO: 29) or Phe-Asn-Arg-Gly-Leu-Asn-Thr-Ile-Ile-Gly-Phe-Gly-Ser-Gly-Ser (SEQ ID NO: 30). Trophinin epitopes useful as a trophinin vaccine can be identified using the methods disclosed in Example III.

A trophinin active fragment can be obtained by recombinant expression using vectors and host cells well known in the art and commercially available (see, for example, *Meth. Enzymol.* vol. 185 (D. Goeddel ed.), Academic Press, NY (1990), which is incorporated by reference; see, also, WO 96/10414, supra; U.S. Pat. No. 5,599,918, supra). Such methods include the ability to construct vectors, that allow expression of polypeptides in a variety of cells, for example, mammalian, bacterial or yeast cells, and can control where in the cell the product is expressed. For example, *Escherichia coli* (*E. coli*), vectors are well known that can direct expression of a polypeptide to the cytoplasm, the periplasm or the medium (see *Meth. Enzymol.*, supra, 1990).

A trophinin active fragment can also be recombinantly expressed as a fusion protein, which contains a trophinin polypeptide fused to a foreign polypeptide, for example, a bacterial ligand binding sequence such as GST or Staphylococcal Protein A. Trophinin expressed as a fusion to GST provides an efficient means to purify the fusion product (Example I; see, also, Uhlen and Moks, in *Meth. Enzymol.*, supra, 1990; pages 129–144). The nucleic acid encoding the non-trophinin gene can be fused to the gene encoding trophinin at either the N-terminus, C-terminus or somewhere else within the trophinin gene.

A trophinin vaccine containing a trophinin fusion protein is useful to provide an adjuvant effect, whereby the resulting immune response to trophinin is enhanced by the addition of the non-trophinin polypeptide in the fusion protein. Alternatively, the trophinin polypeptide can be isolated free from the non-trophinin polypeptide of the fusion protein by encoding in the DNA a unique sequence between the two fusion products that is susceptible to site specific enzymatic cleavage and treating the fusion protein with the appropriate enzyme. Such cleavage sites and enzymes are well known in the art.

A trophinin polypeptide such as a trophinin active fragment also can be obtained by peptide synthesis using methods well known in the art. Trophinin polypeptides made by peptide synthesis can contain either L-amino acids or D-amino acids or a combination thereof, as desired, and the polypeptide can be linear or circular.

A trophinin vaccine of the present invention can also include the entire trophinin protein sequence, such as human trophinin shown in SEQ ID NO: 2 or mouse trophinin as shown in SEQ ID NO: 24. Such native trophinin molecules can be obtained, for example, by recombinant expression from a nucleic acid molecule encoding the trophinin (see, for example, *Meth. Enzymol.*, supra, 1990). In addition, the trophinin vaccine can include the native trophinin protein that is post-translationally modified by a mammalian cell.

A trophinin vaccine can be characterized in reference to the amino acid sequence of the trophinin vaccine and the sequence of trophinin expressed by the individual to be administered the vaccine. For example, an individual can be administered a trophinin vaccine having an amino acid sequence identical with trophinin normally expressed by the individual. Such a self-trophinin vaccine is advantageous in that antibodies raised in response to the vaccine will likely bind to trophinin of the individual administered the vaccine because trophinin of the individual and of the vaccine share the same amino acid sequence. An example of a self-trophinin vaccine is the administration to a human of the human trophinin protein shown in SEQ ID NO: 2.

The immunogenicity of a trophinin vaccine can be enhanced by chemically coupling trophinin to a suitable immunogenic carrier protein. Carrier proteins useful for the present invention have molecular weights of at least about 20,000 Daltons, preferably at least about 40,000 Daltons and more preferably at least about 60,000 Daltons. Carrier proteins useful in the present invention include, for example, GST, hemocyanins such as from the keyhole limpet, serum albumin or cationized serum albumin, thyroglobulin, ovalbumin, various toxoid proteins such a tetanus toxoid or diptheria toxoid, immunoglobulins or heat shock proteins. The immunogenicity of a self-trophinin vaccine can also be enhanced by conjugating trophinin to a carrier protein. Methods to use a carrier protein chemically conjugated to a self-peptide to elicit antibodies to a self protein are well known in the art (see, for example, U.S. Pat. No. 4,608,251, issued Aug. 26, 1986; U.S. Pat. No. 4,161,519, issued Jul. 17, 1979, each of which is incorporated herein by reference).

Methods to chemically couple a polypeptide to a carrier protein are well known in the art and include, for example, conjugation by a water soluble carbodiimide such as 1-ethyl-3-(3dimethylaminopropyl)carbodiimide hydrochloride, conjugation by a homobifunctional cross-linker having, for example, NHS ester groups or sulfo-NHS ester analogs, conjugation by a heterobifunctional cross-linker having, for example, and NHS ester and a maleimide group such as sulfosuccinimidyl-4-(N-maleimidomethyl) cyclohexane-1-carboxylate and, conjugation with gluteraldehyde (see, for example, Hermanson, *Bioconjugate Techniques*, Academic Press, San Diego, Calif. (1996), which is incorporated herein by reference; see, also, U.S. Pat. Nos. 4,608,251 and 4,161, 519, supra).

The choice of conjugation technique will depend on the carrier protein used and the trophinin polypeptide employed. It is important that the conjugation method not destroy antibody defined epitopes normally expressed by the trophinin used for the conjugation and also shared by trophinin of the individual to be administered the vaccine. Methods to evaluate epitope expression by proteins or peptides are well known in the art and include, for example, enzyme-linked immunoadsorbant antibody binding assay (ELISA) or a radioimmunoassay (Harlow and Lane, *Antibodies: A laboratory Manual* Cold Spring Harbor Laboratory Press, (1988), which is incorporated herein by reference; see, also, Examples I and II).

A trophinin vaccine composed of a trophinin active fragment is particularly effective if it contains epitopes that can be recognized by both B cells and T cells and lacks epitopes to which the host immune response is tolerized. Such effective trophinin active fragments useful for a trophinin vaccine can be identified by the Tsites computer program (Feller and Cruz, *Nature* 349:720 (1991); Disis et al, *Cancer Res.* 54:16 (1994), each of which is incorporated herein by reference; Medimune Inc., Gaithersburg Md.). Self-trophinin polypeptides containing T cell and B cell epitopes are generally at least about 10 amino acids to about 30 amino acids in length and, more preferably, are about 15 amino acids to about 18 amino acids in length.

A trophinin vaccine can also be characterized by having a trophinin amino acid sequence that differs from all similar length sequences that are present in trophinin expressed by the individual to be administered the vaccine. Such a non-self trophinin vaccine is also useful in that it can be more immunogenic than a closely related self-trophinin sequence. The mouse trophinin sequence shown in SEQ ID NO: 24, when administered to a human, is an example of a non-self trophinin vaccine. A particularly effective non-self trophinin vaccine can be obtained by mutating the sequence of a self-trophinin vaccine. Methods are well known in the art to mutate a polypeptide sequence at particular positions to optimize the immunogenicity of the polypeptide (Berzofsky, *Ann. NY Acad. Sci.* 690:256, (1993); Margalit et al., *J. Immunol.* 138:2213 (1987), each of which is incorporated herein by reference).

A trophinin vaccine can also contain trophinin active fragments that are presented as a multiple antigen complex, wherein the fragments are combined in a single polypeptide such as described by Tan et al., *Proc. Natl. Acad. Sci., USA* 85:5409 (1988), which is incorporated herein by reference). Such a polypeptide can have multiple copies of the same trophinin active fragment or contain different trophinin active fragments within a single polypeptide.

A trophinin vaccine of the present invention can be administered as a formulation that contains an adjuvant, which enhances the immune response to the trophinin. As used herein, the term "adjuvant" means a chemical that, when administered with the vaccine, enhances the immune response to the vaccine. An adjuvant is distinguished from a carrier protein in that the adjuvant is not chemically coupled to the immunogen or the antigen, i.e. trophinin. Adjuvants are well known in the art and include, for example, mineral oil emulsions (U.S. Pat. No. 4,608,251, supra) such as Freund's complete or Freund's incomplete adjuvant (Freund, *Adv. Tuberc. Res.* 7:130 (1956), which is incorporated herein by reference; Calbiochem, San Diego Calif.), aluminum salts, especially aluminum hydroxide or ALLOHYDROGEL (approved for use in humans by the U.S. Food and Drug Administration), muramyl dipeptide (MDP) and its analogs such as [Thr$^1$]-MDP (Byers and Allison, *Vaccine* 5:223 (1987), which is incorporated herein by reference) and monophosphoryl lipid A (Johnson et al., *Rev. Infect. Dis.* 9:S512 (1987), which is incorporated herein by reference).

A trophinin vaccine can be administered in a microencapsulated or a macroencapsulated form using methods well known in the art. Trophinin can be encapsulated, for example, into liposomes (see, for example, Garcon and Six, *J. Immunol.* 146:3697 (1991), which is incorporated herein by reference), into the inner capsid protein of bovine rotavirus (Redmond et al., *Mol. Immunol.* 28:269 (1991), which is incorporated herein by reference), into immune stimulating molecules (ISCOMS) composed of saponins such as Quil A (Morein et al., *Nature* 308:457 (1984); Morein et al., in *Immunological Adjuvants and Vaccines* (G. Gregoriadis al. eds.) pp.153–162, Plenum Press, NY (1987), each of which is incorporated herein by reference) or into controlled-release biodegradable microspheres composed, for example, of lactide-glycolide compolymers (O'Hagan et al., *Immunology* 73:239 (1991); O'Hagan et al., *Vaccine* 11:149 (1993), each of which is incorporated herein by reference).

A trophinin vaccine can also include trophinin adsorbed to the surface of lipid microspheres containing squalene or squalane emulsions prepared with a PLURONIC block-copolymer such as L-121 and stabilized with a detergent such as TWEEN 80 (see Allison and Byers, *Vaccines: New Approaches to Immunological Problems* (R. Ellis ed.) pp. 431–449, Butterworth-Hinemann, Stoneman N.Y. (1992), which is incorporated herein by reference). A microencapsulated or a macroencapsulated trophinin vaccine can also include an adjuvant.

A trophinin vaccine can also be a nucleic acid molecule encoding trophinin, which can be incorporated into an expression vector so as to enable expression of trophinin in cells of the individual administered the vaccine. The expression of trophinin in cells that take up the vector provides a source of immunogen that elicits anti-trophinin antibodies that can crossreact with trophinin expressed by the uterus of the individual and the fertilized egg. The DNA expression vector can be administered to a subject by intradermal or intramuscular injection (Sato et al., *Science*, 273:352 (1996), which is incorporated herein by reference) or by a hand-held biolistic system, which can propel DNA-coated gold microprojectiles directly into the cells of the individual (see, for example, Sanford et al., *Meth. Enzymol.* vol. 217, pp. 483–510 (R. Wu ed.), Academic Press, NY (1993), which is incorporated by reference; Williams et al., *Proc. Natl. Acad. Sci., USA*, 88:2726 (1991), which is incorporated herein by reference).

A trophinin vaccine can also include a biological vector such as a live or attenuated virus or bacteria that is engineered to express trophinin. An immunogenic biological vector that expresses trophinin acts as an adjuvant and enhances the immune response to trophinin. Methods to express polypeptides from biological vectors are well known in the art and include, for example, expression from a recombinant vaccinia virus vector (see, for example, Bernards et al., *Proc. Natl. Acad. Sci., USA* 84:6854 (1987), which is incorporated herein by reference) or from Salmonella containing an appropriate vector (Schödel et al., *Vaccine* 11:143 (1990), which is incorporated herein by reference).

In order to stimulate an immune response against trophinin, an effective dose of the vaccine is administered to the individual. As used herein, the term "effective dose" means an amount of immunogen required to stimulate an immune response that can block trophinin mediated adhesion between embryonic trophoblast cells and uterine epithelial cells, thereby inhibiting embryo implantation. The amount of trophinin vaccine that constitutes an effective dose will vary, depending, for example, on whether the vaccine is administered as a primary or booster administration, whether adjuvant is used, the size of mammal being immunized and the route of administration. In general, an effective dose of vaccine for a human is about 50 µg to about 500 mg, preferably about 500 µg to about 5 mg. Methods for determining a therapeutically effective dose of an immunogen are routine and well known in the art (See, for example, Powell and Newman, *Vaccine Design: The subunit and adjuvant approach* (Plenum Publ. Corp.; 1994) which is incorporated herein by reference).

The schedule of administration of a vaccine to elicit an effective immune response also is well known in the art (see, for example, Harlow and Lane, supra, 1988). A trophinin vaccine can be administered by various routes such as intradermaly, intramuscularly, intravenously or orally. The choice of route will vary, depending, for example, on the type of formulation, the presence of adjuvant and whether the vaccine is administered as a primary or booster administration. The need to administer one or more booster immunizations can be determined experimentally by measuring the immune response to trophinin that occurs in response to administration of the vaccine. For example, the immune response can be evaluated by obtaining a sample of serum from the individual administered the vaccine and measuring the titer of antibodies to trophinin using cell binding or ELISA assays as disclosed herein (see, for example, Harlow and Lane, supra, 1988). Long term immunity to trophinin and protection against pregnancy by such immunity can be maintained by occasional booster administrations of the trophinin vaccine. By stopping further administration of the vaccine, the immune response to trophinin can decline over time thus allowing the individual to become pregnant.

The present invention also provides a substantially purified trophinin active fragment having an amino acid sequence such as Phe-Asp-Arg-Gly-Leu-Ser-Thr-Ile-Ile (SEQ ID NO: 25), Thr-Ile-Ile-Gly-Phe-Gly-Ser-Gly-Ser (SEQ ID NO: 26), Phe-Asp-Arg-Gly-Leu-Ser-Thr-Ile-Ile-Gly-Phe-Gly-Ser-Gly-Ser (SEQ ID NO: 27), Ser-Ile-Val-Gly-Phe-Ser-Gly-Gly-Pro (SEQ ID NO: 28), Phe-Asn-Arg-Gly-Leu-Asn-Thr-Ile-Ile (SEQ ID NO: 29) or Phe-Asn-Arg-Gly-Leu-Asn-Thr-Ile-Ile-Gly-Phe-Gly-Ser-Gly-Ser (SEQ ID NO: 30). Such trophinin active fragments are useful, for example, as a trophinin vaccine to elicit antibodies that react with trophinin, or can be used to evaluate the specificity of antibodies produced in an individual administered a trophinin vaccine. Methods to evaluate the specificity of antibodies to peptides are well known in the art and include, for example, liquid phase or solid phase assays such as ELISA or radioimmunoassay (see, for example, Harlow and Lane, supra, 1988; see, also, Example III).

The present invention also provides a substantially purified mammalian trophinin having the amino acid sequence of human trophinin shown in SEQ ID NO: 2 or of mouse trophinin as shown in SEQ ID NO: 24. The amino acid sequence of human and mouse trophinin were derived from the nucleotide sequence shown in SEQ ID NO: 1 and SEQ ID NO: 23, respectively.

The present invention also provides mammalian trophinin that is similar in sequence to that of SEQ ID NO: 2 and SEQ ID NO: 24, but has one or more amino acid additions, deletions or substitutions that do not substantially alter the ability of the encoded protein to function like a trophinin and, for example, mediate cell adhesion or elicit trophinin specific antibodies. In general, an amino acid sequence having at least 65% sequence homology with the residues of SEQ ID NO: 2 is considered a trophinin sequence provided it is characterized, in part, by having a greater sequence homology with other mammalian trophinins as compared with other cell adhesion type molecules, by expression primarily in reproductive tissues and, by mediating cell adhesion between embryonic and trophoblastic cells.

It is well recognized that various amino acids in a polypeptide can be replaced by other naturally- or non-naturally-occurring L- or D-amino acids having equivalent reactive side chains or by other chemical compounds without substantially changing the biological activity of the polypeptide. For example, a hydrophobic amino acid such as leucine can be replaced by another hydrophobic amino acid such as alanine without substantially changing the amino acid sequence or activity of a trophinin polypeptide. In addition, the N-terminus or C-terminus or a reactive side chain of an amino acid can be modified, for example, by acetylation or amidation, without substantially changing the activity of a trophinin polypeptide. Such modified proteins can have advantageous properties including, for example, increased stability in vivo or in vitro, and the present invention includes mammalian trophinin so modified.

As used herein, the term "substantially purified" means a protein that is in a form that is relatively free from contaminating lipids, proteins, nucleic acids or other material normally associated with a protein in a cell. Substantially purified trophinin can be obtained, for example, using well known biochemical methods of purification or by expressing a recombinant nucleic acid molecule encoding a trophinin such as the nucleic acid molecule shown in SEQ ID NO: 1. In addition, an amino acid sequence consisting of at least a portion of the amino acid sequence of SEQ ID NO: 2, can be chemically synthesized or can be produced by expressing a portion of the nucleotide sequence shown in SEQ ID NO: 1 (see Example I).

A substantially purified protein also includes a protein produced in an environment that is separate or distinct from it's native cellular environment. For example, the substantially purified protein includes a protein expressed in a cell that does not normally express the protein or can be expressed in the cell at a level higher than normally expressed by the cell. The ability to manipulate a cell to express a recombinant form of a protein of the present invention provides distinct advantages such as increased cell adhesion.

As used herein, the term "active fragment" means a portion of a full length protein, provided the portion retains at least one activity that is characteristic of the full length protein. For example, an active fragment of trophinin can be a portion of the full length trophinin protein that can effect cell adhesion or can elicit specific antibodies to trophinin. An active fragment of trophinin can be identified, for example, by expressing a portion of the trophinin protein and determining if it can bind anti-trophinin antibodies (see Examples I and II).

The complete amino acid sequence of human trophinin was deduced from the nucleotide sequence of a cDNA clone encoding human trophinin. The human trophinin cDNA (SEQ ID NO: 1) contains an open reading frame coding for 749 amino acids. In vitro translation of trophinin cDNA and analysis using sodium dodecyl sulfate polyacrylamide gel electrophoresis (SDS-PAGE) showed that trophinin is synthesized as a major product of 61 kiloDaltons (kDa; WO 96/10414, supra, FIG. 4). This experimentally determined molecular mass is in agreement with the predicted molecular mass of 69.29 kDa based on the cDNA open reading frame.

Hydropathy analysis (Kyte and Doolittle, *J. Mol. Biol.* 157:105–132 (1982)) indicates that human trophinin is an intrinsic membrane protein having eight separate transmembrane domains (WO 96/10414, supra, FIG. 5A). The relative proportion of human trophinin localized in the cytoplasm, in the membrane bilayer and on the cell surface is about 10%, 56% and 34%, respectively. The amino terminal portion of trophinin is likely located in the cytoplasm because the first putative membrane spanning domain (amino acids 66 to 120) follows an arginine residue at position 54, which can function as a stop transfer signal during translocation into the endoplasmic reticulum, and because antibodies raised to an amino terminal peptide of human trophinin (residues 23 to 31) react only with cells that have had their membranes permeabilized by detergent treatment (Example I).

The amino terminal region of human and mouse trophinin contains many serine and threonine residues that can function as potential phosphorylation sites for enzymes such as casein kinase II (Kemp and Pearson, *Trends Biochem. Sci.* 15:342–346 (1990)), protein kinase C, and cAMP/cGMP dependent kinases (WO 96/10414, supra, FIG. 3; SEQ ID NO: 1). In addition, four potential N-glycosylation sites and thirteen potential O-glycosylation sites are present within the predicted cell surface domains of human trophinin (WO 96/10414, supra, FIG. 3).

Greater than 90% of human trophinin is composed of a tandemly repeated motif primarily decapeptide in character. There are 69 such repeat sequences, which exhibit some variation in sequence and length (WO 96/10414, supra, FIG. 5B). Portions of the repeat motifs are contained within three regions of trophinin that are hydrophilic in character and are exposed on the external side of the cell plasma membrane. The human trophinin external membrane domains are located, referring to the sequence of human trophinin (SEQ ID NO: 2), from amino acid positions 278 to 364 (SEQ ID NO: 20), 441 to 512 (SEQ ID NO: 21) and 634 to 719 (SEQ ID NO: 22; WO 96/10414, supra, FIG. 3, bold lettering). Protein secondary structure algorithms (Garnier et al., *J. Mol. Biol.* 120:97–120 (1978); Gascuel and Golmard, *Comput. Appl. Biosci.* 4:357–365 (1988)) predict that the decapeptide repeats conform to a repeated β-turn structure, which can be involved in homophilic adhesion.

In addition to trophinin, a cell can require the expression of a trophinin-assisting protein in order to effect cell adhesion which include human tastin (SEQ ID NO: 5), human bystin (SEQ ID NO: 7) and a portion of human lastin (SEQ ID NO: 9). A trophinin-assisting protein can enable adhesion of cells that express trophinin. As used herein, the term "substantially the amino acid sequence" means the disclosed amino acid sequence of human tastin (SEQ ID NO: 5), human bystin (SEQ ID NO: 7) or human lastin (SEQ ID NO: 9) as well as amino acid sequences that are similar to SEQ ID NO: 5, SEQ ID NO: 7 or SEQ ID NO: 9, respectively, but have one or more amino acid additions, deletions or substitutions that do not substantially alter the ability of the encoded protein to function like a trophinin-assisting protein and, for example, assist trophinin in mediating cell adhesion or elicit a trophinin-assisting protein specific antibody.

As used herein, the term "trophinin-assisting protein" is used generally to mean a member of the trophinin-assisting protein family of proteins as defined by their ability to assist trophinin in mediating adhesion of cells. Trophinin-assisting proteins include such family members as tastin, bystin or lastin and can be a full length trophinin-assisting protein or an active fragment of a trophinin-assisting protein. For example, amino acids 1 to 675 of lastin are a portion of the full length protein and can assist trophinin in mediating cell adhesion. While not necessarily structurally related, trophinin-assisting protein family members are characterized, in part, by having the property of assisting trophinin mediated cell adhesion.

Trophinin and a trophinin-assisting protein can interact directly or indirectly to effect cell adhesion. For example, cell adhesion can be mediated by the direct binding of a trophinin-assisting protein to trophinin. Cell adhesion also can be due to a trophinin-assisting protein binding to another cellular molecule which then directly or indirectly binds to trophinin. Alternatively, a trophinin-assisting protein can interact indirectly with trophinin by binding to and eliminating the function of a negative regulator of trophinin activity in the cell.

A substantially purified trophinin-assisting protein can be obtained, for example, using well known biochemical methods of purification or by expressing a recombinant nucleic acid molecule encoding a trophinin-assisting protein such as the nucleic acid molecules shown in SEQ ID NO: 4, SEQ ID NO: 6 or SEQ ID NO: 8. In addition, an amino acid sequence consisting of at least a portion of the amino acid sequences of SEQ ID NO: 5, SEQ ID NO: 7 or SEQ ID NO: 9 can be chemically synthesized or can be produced by expressing a portion of the nucleotide sequence shown in SEQ ID NO: 4, SEQ ID NO: 6 or SEQ ID NO: 8, respectively.

The complete amino acid sequence of tastin (SEQ ID NO: 5) was deduced from the nucleotide sequence of the tastin cDNA clone (as shown in FIG. 6 of WO/10414, supra). The open reading frame of the tastin cDNA encodes a protein having 778 amino acids. Tastin exhibits an apparent molecular mass of about 80 kDa based on SDS-PAGE analysis of in vitro translated tastin cDNA (WO 96/10414, supra, FIG. 4). This mass is consistent with a molecular weight of 83.75 kDa calculated from the tastin cDNA open reading frame. Tastin lacks a consensus signal sequence characteristic of a secreted protein and contains no transmembrane helices as assessed by hydropathy analysis (Kyte and Doolittle, supra, 1982). Thus, tastin has the characteristics of a cytoplasmic protein.

Tastin is rich in proline residues, which account for 15.3% of the total amino acids of the protein, and in cysteine residues. The majority of the cysteines are located between position 516 to 650 and occur primarily within four tandemly repeated sequences of 33 amino acids each (WO 96/10414, supra, FIG. 6, see region denoted by italics). Tastin contains many serine and threonine residues that are potential sites for phosphorylation, including two potential sites for cAMP/cGMP dependent kinase, sixteen sites for protein kinase C (Kemp and Pearson, supra, 1990), eleven sites for casein kinase II and two sites for MAP kinase (Gonzalez et al., *J. Biol. Chem.* 266:22159–22163 (1991); see WO 96/10414, supra, FIG. 6). Specifically, tastin contains two cAMP/cGMP-dependent phosphorylation sites located at position 234 and 350 and sixteen protein kinase C phosphorylation sites, among which the threonine at position 179 most closely matches the consensus sequence (Kemp and Pearson, supra, 1990). Tastin also contains eleven serine and threonine residues that are potential casein kinase II phosphorylation sites and two threonines at positions 177 and 363 that are within a consensus MAP kinase phosphorylation site (Gonzalez et al., supra, 1991).

Nucleotide sequence homology analysis of tastin identified the sequence HFBCL29 (Genbank accession number M85643), which was derived from a human fetal brain cDNA library. HFBCL29 shows DNA base complementarity to a portion of tastin cDNA (positions 2057 to 2340). Thus, the HFBCL29 sequence can be homologous to a portion of the tastin sequence if HFBCL29 was recorded in the data base in the antisense direction. The protein sequence deduced from HFBCL29 is related to Y box binding protein-1 (Adams et al., *Nature* 355:632–634 (1992)). However, the entire nucleotide sequence and deduced amino acid sequence of tastin are not homologous overall to the Y-box binding protein-1.

The complete amino acid sequence of bystin was deduced from the nucleotide sequence of the bystin cDNA clone and is shown in SEQ ID NO: 7. The open reading frame of the bystin cDNA codes for a protein of 306 residues. Bystin contains threonine and serine residues within potential sites for phosphorylation by protein kinase C (underlined) and casein kinase II (bolded). In addition, bystin contains tyrosine residues (bolded) that are potential sites of phosphorylation by tyrosine kinase and glycine residues within potential sites for myristoylation (bolded). Amino acid residues 1 to 88 of bystin show a significant degree of sequence homology to the bys gene previously identified in Drosophila (Stuart et al., *Mol. Cell. Biol.* 13:2524 (1993)).

A partial amino acid sequence of lastin was deduced from a partial nucleotide sequence of the lastin cDNA clone and is shown in SEQ ID NO: 9. The lastin cDNA clone does not contain the 3' end of the gene, including the stop codon and the poly-A tail. The open reading frame of the partial cDNA encodes for 675 amino acids. Lastin contains threonine and serine within potential sites for phosphorylation by protein kinase C (underlined) and casein kinase II (bolded). Lastin also contains potential sites for myristoylation of glycine residues.

The present invention provides antibodies that are specifically reactive with trophinin or with a trophinin-assisting protein. As used herein, the term "antibody" is used in its broadest sense to include polyclonal and monoclonal antibodies, as well as polypeptide fragments of antibodies that retain a specific binding affinity for trophinin or a trophinin-assisting protein of at least about $1 \times 10^5$ $M^{-1}$. One skilled in the art would know that antibody fragments such as Fab, F(ab')$_2$ and Fv fragments can retain specific binding activity for their target antigen and, thus, are included within the definition of an antibody to trophinin or to a trophinin-assisting protein. In addition, the term "antibody" as used herein includes naturally occurring antibodies as well as non-naturally occurring antibodies such as domain-deleted antibodies (Morrison and Oi, WO 89/07142, issued Aug. 10, 1989, which is incorporated herein by reference) or single chain Fv (Ladner and Bird, U.S. Pat. No. 5,250,203, issued Nov. 9, 1993, which is incorporated herein by reference). Such non-naturally occurring antibodies can be constructed using solid phase peptide synthesis, can be produced recombinantly or can be obtained, for example, by screening combinatorial libraries consisting of variable heavy chains and variable light chains as described by Huse et al., *Science* 246:1275–1281 (1989), which is incorporated herein by reference.

Particularly useful non-naturally occurring antibodies include chimeric antibodies and humanized antibodies. Methods to produce chimeric antibodies and humanized antibodies by the method of CDR grafting are known in the art (see, for example, Winter, U.S. Pat. No. 5,225,539, Jul. 6, 1993, which is incorporated herein by reference).

As used herein, the term "chimeric antibody" means an antibody having a human constant region and a variable region from an organism other than a human. For example, a chimeric antibody useful in the invention can consist of a human IgG constant region and a variable region obtained from a mouse anti-human trophinin antibody. As used herein, the term "humanized antibody" means an antibody having constant and framework regions derived from human and hypervariable regions derived from an organism other than a human. For example, a humanized antibody useful in the invention can consist of the amino acids that form the hypervariable region of a mouse anti-human trophinin antibody and the amino acids that form the framework region and constant regions of a human IgG class antibody.

Chimeric antibodies and humanized antibodies are particularly useful for administration to a human subject, since the likelihood of an immune response by the subject against the antibody is minimized. Other non-naturally occurring antibodies within the present invention include bispecific antibodies, in which the antibody contains at least two different binding specificities that can be univalent or multivalent for each particular binding specificity. Methods for producing bispecific antibodies by chemical crosslinking or by heterohybridoma formation are well known in the art (for trivalent antibodies, see, for example, Ahlem and Huang, U.S. Pat. No. 5,273,743, issued Dec. 28, 1993), which is incorporated herein by reference).

An anti-trophinin antibody or an anti-trophinin-assisting protein antibody can be prepared using substantially purified trophinin or a trophinin-assisting protein, respectively, either of which can be obtained from natural sources or produced by recombinant DNA methods or chemical synthesis. For example, recombinant DNA methods can be used to express trophinin alone or as a fusion protein, which can facilitate purification of the antigen and enhance its immunogenicity (Example I). Similarly, an active fragment of trophinin or of a trophinin-assisting protein also can be obtained as described above and can be used as an immunogen (Example I). If not sufficiently immunogenic, such fragments or peptides can be made immunogenic by expressing the hapten as a fusion protein or by coupling the hapten to an immunogenic carrier molecule such as bovine serum albumin or keyhole limpet hemocyanin (KLH). Various other carrier molecules and methods for coupling a non-immunogenic peptide to a carrier molecule are well known in the art (see, for example, Harlow and Lane, supra, 1988). Methods for raising an antibody and measuring the extent of the immune response are also routine (Harlow and Lane, supra, 1988).

An antiserum containing polyclonal antibodies to trophinin or to a trophinin-assisting protein can be raised in rabbits, goats or other animals. The resulting antiserum can be processed by purification of an IgG antibody fraction using protein A SEPHAROSE chromatography and, if desired, can be further purified by affinity chromatography using, for example, Sepharose conjugated with a peptide antigen (Example I). The ability of polyclonal antibodies to specifically bind to a given molecule can be manipulated, for example, by dilution or by adsorption to remove crossre-acting antibodies to a non-target molecule. Methods to manipulate the specificity of polyclonal antibodies are well known to those in the art (See, for example, Harlow and Lane, supra, 1988).

A monoclonal anti-trophinin or anti-trophinin-assisting protein antibody can be produced using methods well known in the art (see, for example, Harlow and Lane, supra, 1988). Essentially, spleen cells from a trophinin- or a trophinin-assisting protein-immunized animal can be fused to an appropriate myeloma cell line such as SP2/0 myeloma cells to produce hybridoma cells. Cloned hybridoma cell lines can be screened using a labeled trophinin or trophinin-assisting protein polypeptide to identify clones that secrete an appropriate monoclonal antibody. A trophinin or a trophinin-assisting protein polypeptide can be labeled as described below. A hybridoma that expresses an antibody having a desirable specificity and affinity can be isolated and utilized as a continuous source of monoclonal antibodies. Methods for identifying an anti-trophinin or anti-trophinin-assisting protein antibody having an appropriate specificity and affinity and, therefore, useful in the invention are known in the art and include, for example, enzyme-linked immunoadsorbance assays, radioimmunoassays, precipitin assays and immunohistochemical analyses (see, for example, Harlow and Lane, supra, 1988, chapter 14).

An anti-trophinin antibody can be characterized by its ability to bind a portion of a mammalian trophinin protein, such as the portion of trophinin that is exposed on the external side of the plasma membrane of a cell (see, for example, WO 96/10414, supra, FIG. 1D; see, also Example I and II). An anti-trophinin-assisting protein antibody can also be characterized by its ability to bind to an epitope that is unique to one or more members of the trophinin-assisting protein family of proteins (Example III).

The present invention also provides nucleic acid molecules encoding mammalian trophinin. For example, the invention provides a substantially purified nucleic acid molecule encoding human trophinin having substantially the nucleotide sequence shown in SEQ ID NO: 1 or mouse trophinin having substantially the nucleic sequence shown in FIG. 1 (SEQ ID NO: 23). As used herein in the context of a nucleic acid, the term "substantially purified" means that the nucleic acid is relatively free from contaminating materials such as lipids, proteins, carbohydrates or cellular material normally associated with a nucleic acid in a cell. For example, a nucleic acid molecule that is chemically synthesized is considered substantially purified. Recombinant DNA methods for producing a substantially purified nucleic acid are well known in the art and include cloning a sequence or polymerase chain reaction (PCR) amplification of a sequence (see Sambrook et al., *Molecular Cloning: A laboratory manual* Cold Spring Harbor Laboratory Press (1989), which is incorporated herein by reference; see, also, Erlich, *PCR Technology: Principles and applications for DNA amplification* Stockton Press (1989), which is incorporated herein by reference).

A substantially purified nucleic acid also includes a nucleic acid produced in an environment that is separate or distinct from the nucleic acid in it's native cellular environment. For example, the substantially purified nucleic acid is a nucleic acid expressed by recombinant techniques in a cell that does not normally express the nucleic acid or expressed at levels that are higher than normally expressed by the cell. The ability to manipulate a cell to express the nucleic acids of the present invention provides distinct advantages such as increased cell adhesion.

The nucleic acid molecules of the present invention include a sequence that contains, for example, different nucleotides than shown in SEQ ID NO: 1 but that, as a result of the degeneracy of the genetic code, encodes substantially the same amino acid sequence as shown in SEQ ID NO: 2. Such nucleotide sequences can be either DNA or RNA and can encode either the coding or non-coding nucleotide strand.

The cloned nucleic acid molecule encoding human trophinin (SEQ ID NO: 1) contains 2524 nucleotides with an open reading frame encoding 749 amino acids. The 3'-untranslated region of human trophinin consists of 250 nucleotides and contains a polyadenylation signal located twelve nucleotides upstream of the poly-A tail. Among the ATC codons in the 5'-region, the sequence around the ATG at position 1 in SEQ ID NO: 1 closely matches a Kozak sequence optimal for translation initiation (Kozak, *Nucleic*

Acids Res. 12:857–872, (1984)). No other ATG codon near the 5' end conforms to the consensus sequence for translation initiation. In vitro translation of the human trophinin cDNA confirms that the ATG beginning at position 1 in SEQ ID NO: 1 encodes the initiation methionine in trophinin.

The mouse trophinin gene was cloned from a genomic library by screening for cloned sequences that hybridize with a probe made from the human trophinin cDNA (Example V). A BamHI restriction fragment from the mouse genomic clone that cross-hybridized with human trophinin cDNA was sequenced and a general genomic structure thus determined. The mouse genomic fragment contained a complete open reading frame beginning with a methionine codon located within a sequence context largely consistent with Kozak's consensus rules for mammalian translation initiation (Kozak, *J. Biol. Chem.* 266:19867 (1991)). The mouse trophinin gene has an intronless open reading frame as does the human trophinin gene.

The predicted amino acid sequence of mouse trophinin deduced from the open reading frame encodes an 1160 residue protein with a calculated molecular weight of 107 kDa. Mouse trophinin consists of two distinct regions: a short sequence containing the amino-terminal portion of the molecule from residue 1 to about residue 50, and the tandem repeat region that represents the remainder of the molecule, from about residue 51 to residue 1160. The majority of the repeat sequences representing about 76% are decapeptide repeat sequences (FIG. 1).

The mouse and human trophinin proteins share significant structural features. The overall amino acid sequence homology between mouse and human trophinin is 45%. Prediction of protein secondary structure performed using the TMpred program (Hofman and Stoffel, *Biol. Chem. Hoppe-Seylor.* 374:166 (1993)) indicates that mouse trophinin is a transmembrane protein with the amino-terminal region in the cytoplasm, as is disclosed for human trophinin.

The amino-terminal 50 residues of mouse and human trophinin are highly conserved showing 78% homology based on identical residues and 85% homology based on identical residues plus conservative substitutions (see FIG. 2A). In particular, three serine and threonine residues that are potential phosphorylation sites by protein kinases are located in the mouse and human trophinin N-terminal sequences at nearly identical positions (FIG. 2A; bold and underlined/bold).

Residues 972 to 1053 of mouse trophinin and residues 635 to 716 of human trophinin (within the human trophinin third extracellular domain) are also highly conserved. The degree of homology in this region is 81% based on identical residues and 84% based on identical residues plus conservative substitutions (see FIG. 2B). This high degree of homology of the mouse sequence at position 972 to 1053 to the human extracellular domain indicates the mouse sequence is located extracellularly.

Homology between the amino acid sequence of mouse and human trophinin was also observed for a region containing residues 187 to 335 of the a-agglutinin subunit of the yeast AGA1 protein (FIG. 3)(BLASTP P-value, $5.8 \times 10^{-16}$). Like trophinin, the yeast AGA1 molecule is involved in cell-cell adhesion of a-type and α-type yeast during mating. The yeast AGA1 gene is regulated by sex hormones (Herman et al., *Mamm. Genome* 5:S276–S288 (1994)) and, like the mouse and human trophinin gene has an intronless open reading. Sequence alignments of the most homologous regions from human trophinin, mouse trophinin, and yeast AGA1 a-agglutinin subunit show a great deal of homology (FIG. 3). These data show that human trophinin, mouse trophinin and the yeast AGA1 a-agglutinin subunit constitute a new gene family of cell surface molecules involved in reproductive cell adhesion.

The invention also provides a nucleotide sequence that can hybridize to a portion of the nucleic acid molecule encoding trophinin under relatively stringent hybridization conditions but does not hybridize to the mRNA from COS-1 cells or to human trophinin. Relatively stringent hybridization conditions can be determined empirically or can be estimated based, for example, on the relative GC:AT content of the hybridizing nucleotide sequence and the target sequence, the length of the hybridizing nucleotide sequence and the number, if any, of mismatches between the hybridizing nucleotide sequence and the target sequence (See, for example, Sambrook et al., supra, 1989, pages 11.45 to 11.57). The extent of hybridization can be controlled, for example, by the temperature, pH or ionic strength of the hybridization reaction mixture or the subsequent wash solutions (see, for example, Sambrook et al., supra, 1989, see chapters 9–11).

A nucleotide sequence useful for hybridizing to a nucleic acid molecule encoding trophinin should generally be at least about 14 nucleotides in length, preferably about 16 to 20 nucleotides in length and, preferably about 30 to 50 nucleotides in length or greater. The choice of probe length can vary depending on the hybridization method employed. For example, a probe as short as about 10 nucleotides can be useful as a primer in PCR if combined with a longer primer that is specific to trophinin. Nucleic acid molecules that can be used for hybridization can be prepared, for example, by restriction endonuclease digestion of a cloned nucleic acid molecule, such as the nucleic acid molecule shown in SEQ ID NO: 1, by PCR amplification of a portion of a nucleic acid encoding trophinin or by chemical synthesis using well known methods. A nucleotide sequence can be labeled with a detectable moiety and can be used as a probe to detect a nucleic acid molecule or as a primer for PCR. Methods for detectably labeling a nucleic acid are well known in the art (see, for example, Sambrook et al., supra; Ausubel et al., *Current Protocols in Molecular Biology* (John Wiley & Sons 1987), which is incorporated herein by reference).

The cloned nucleic acid molecule encoding human tastin (SEQ ID NO: 4) contains 2,577 nucleotides having an open reading frame encoding 778 amino acids (see WO 96/10414, supra, FIG. 6). The 3' untranslated region contains 133 nucleotides and has a polyadenylation signal located eleven nucleotides upstream of the poly-A tail. The nucleotide sequence around the ATG beginning at position 111 conforms to the consensus sequence for the translation initiation site (Kozak, supra, 1984). In vitro translation of the tastin cDNA confirms that the ATG beginning at position ill in SEQ ID NO: 4 encodes the initiation methionine in tastin.

The cloned nucleic acid molecule encoding human bystin (SEQ ID NO: 6) contains 1,293 nucleotides having an open reading frame encoding 306 amino acids (WO 96/10414, supra, FIG. 7). The 3'-untranslated region contains 306 nucleotides.

The cloned nucleic acid molecule encoding a portion of human lastin is based on the sequence of a partial cDNA clone (SEQ ID NO: 8) that contains 2,223 nucleotides having an open reading frame encoding 675 amino acids beginning at the ATG start site (WO 96/10414, supra, FIG. 8). The 5' untranslated region contains 198 nucleotides. The nucleotide sequence around the ATG at position 199 conforms to the consensus sequence for the translation initiation site (Kozak, supra, 1984).

The invention provides vectors containing a nucleic acid molecule encoding a mammalian trophinin or a mammalian trophinin-assisting protein and host cells containing the vectors. Vectors are well known in the art and include, for example, cloning vectors and expression vectors, as well as plasmids or viral vectors (see, for example, *Meth. Enzymol.* vol. 185, supra, 1990). For example, an expression vector that contains a nucleic acid molecule encoding trophinin can be particularly useful for expressing large amounts of trophinin protein, which can be purified and used as an immunogen to raise anti-trophinin antibodies. A baculovirus vector is an example of a vector that can be used to express large amounts of trophinin or a trophinin-assisting protein. A vector containing a nucleic acid molecule encoding a trophinin or a trophinin-assisting protein can also contain a promoter or enhancer element, which can be constitutive or inducible and, if desired, can be tissue specific. Host cells also are known in the art and can be selected based on the particular vector. An appropriate host cell can be selected based, on the particular vector used, for example, baculovirus transfer vectors can be used with baculovirus DNA to infect insect cell lines such as SF21 cells.

Methods for introducing expression vectors into cells are well known in the art (see, for example, Sambrook et al., supra, 1989; Kriegler M. *Gene Transfer and Expression: A Laboratory Manual* W. H. Freeman and Co. New York N.Y. (1990), which is incorporated herein by reference) and, include, for example, transfection methods such as calcium phosphate, electroporation or lipofection, or viral infection.

Recombinant viral vectors are available for introducing exogenous nucleic acid molecules into mammalian cells and include, for example, adenovirus, herpesvirus and retrovirus-derived vectors. For example, a viral vector encoding trophinin or a trophinin-assisting protein can be packaged into a virus to enable delivery of the genetic information and expression of these proteins in endometrial cells following infection by the virus.

Recombinant viral infection can be more selective than direct DNA delivery due to the natural ability of viruses to infect specific cell types. This natural ability for selective viral infection can be exploited to limit infection to specific cell types within a mixed cell population. For example, adenoviruses can be used to restrict viral infection principally to cells of epithelial origin. In addition, a retrovirus can be modified by recombinant DNA techniques to enable expression of a unique receptor or ligand that provides further specificity to viral gene delivery. Retroviral delivery systems can also provide high infection rates, stable genetic integration, and high levels of exogenous gene expression.

As described above, recombinant viral delivery systems exist that provide the means to deliver genetic information into a selected type of cell. The choice of viral system will depend on the desired cell type to be targeted, while the choice of vector will depend on the intended application. Recombinant viral vectors are readily available for those in the art and can be easily modified by one skilled in the art using standard recombinant DNA methods.

The invention also provides methods to detect trophinin or a nucleic acid molecule encoding trophinin in a sample using an agent that specifically binds to trophinin or to a nucleic acid molecule encoding trophinin. As used herein the term "agent" means a chemical or biological molecule that can specifically bind to trophinin or to a trophinin-assisting protein or to a nucleic acid molecule encoding trophinin or a trophinin-assisting protein. For example, an agent specific for trophinin can be another trophinin molecule or can be an anti-trophinin antibody. In addition, an agent can be a nucleotide sequence that binds to a nucleic acid molecule encoding trophinin or a trophinin-assisting protein.

As used herein, "sample" means a specimen such as a cell, tissue or an organ, which can be obtained, for example, by biopsy from a subject or can be a serum, urine or mucin specimen obtained from a subject. A sample containing trophinin can be used directly or can be processed prior to testing. For example, a biopsy tissue sample can be cut into tissue sections for histologic examination or can be further processed to release trophinin from cells within the tissue. Methods to process a sample such as a tissue, cells or a biological fluid for detecting a protein are known in the art (see, for example, Harlow and Lane, supra, 1988).

The presence of trophinin in a sample can be determined by contacting the sample with an agent that can bind to trophinin under suitable conditions, which allow the agent to specifically bind to trophinin. Suitable conditions can be achieved using well known methods and can be optimized, for example, by varying the concentration of reactants or the temperature of the reaction. After the agent specifically binds to trophinin in a sample, the presence of trophinin can be determined by detecting specific binding of the agent.

An agent that can be detectably labeled can be used as a probe. For example, a probe for detecting the presence of trophinin in a sample can be an anti-trophinin antibody that is detectably labeled or that can be bound by a second antibody that is detectably labeled. In addition, a probe for detecting a nucleic acid molecule encoding trophinin or a trophinin-assisting protein can be an agent such as a nucleotide sequence that can hybridize to the nucleic acid molecule and that can be detected directly, for example, by a radioactive moiety incorporated into the nucleotide sequence, or indirectly, for example, by PCR analysis.

As used herein, "detectable label" means a molecule whose presence can be detected due to a physical, chemical or biological characteristic of the molecule. Detectable labels include, for example, radioisotopes, fluorescent molecules, enzyme/substrate systems, or visually detectable molecules. Methods to produce a probe for detecting a protein are well known in the art (see, for example, Harlow and Lane, supra, 1988) and include, for example labeling the agent with a radioisotope, fluorescence molecule or histochemically useful enzyme or visible particle or colloid. Methods to produce a probe for detecting a nucleic acid molecule are also well known in the art (see, for example, Sambrook et al., supra; *Nucleic acid Hybridization: A Practical approach*, (Hames and Higgins eds.) IRL press, New York, (1985), which is incorporated herein by reference).

An agent often can bind to a limited but detectable level with non-target substances, for example, the assay container or other proteins unrelated to trophinin and can result in background binding. Thus, to properly conclude that the presence of an agent binding in a sample represents the presence of trophinin, it is necessary to determine what is the contribution of background binding to the assay. The level of background binding of an agent can be determined using a control sample, which is similar in composition to the sample being tested but which contains a defined amount of trophinin, no trophinin or proteins unrelated to trophinin.

COS-1 cells do not express detectable trophinin and, therefore, a sample containing nucleic acids from COS-1 cells provides a useful control to determine background binding of the agent. Specific detection of trophinin by the agent occurs when the agent binds to a greater extent with the experimental sample than it does to a control sample having no trophinin. Quantification of the amount of trophinin detected in a sample by an agent that binds to trophinin can be estimated by comparison of the extent of reaction with that obtained using samples containing known amounts of trophinin. Standard curves relating the extent of binding of the agent with samples containing known amounts of trophinin can be used to estimate the quantity of trophinin in a sample.

A nucleic acid molecule encoding trophinin can be detected in a sample using an agent such as an antisense nucleotide sequence that is specific for trophinin as described above. The target nucleic acid molecule can be extracted from a sample by methods well known in the art (See, for example, Sambrook et al., supra). Methods to detect the presence of a particular nucleic acid molecule within a population of nucleic acid molecules are well known to those in the art and include, for example, Southern blotting, northern blotting, slot blotting and PCR amplification (see, for example, Sambrook et al., supra, 1989). In situ hybridization also can be particularly useful for identifying nucleic acids in a sample (see, for example, Pardue, *Nucleic Acid Hybridization: A Practical Approach* (B. D. Hames and S. J. Higgins eds.) IRL Press, Washington D.C. (1991), which is incorporated herein by reference).

To detect a nucleic acid molecule encoding trophinin in a sample, the sample is contacted with a nucleotide sequence probe that can hybridize to a nucleic acid molecule encoding trophinin under relatively stringent conditions. The presence of a nucleic acid molecule encoding trophinin in the sample can be determined, for example, by detecting the presence of a specifically bound nucleotide sequence probe. The degree of background binding of the probe also can be determined in a control sample to confirm that binding seen in the sample is due to the presence of the target nucleic acid molecule.

A combination of both protein detecting and nucleic acid detecting methods, when used together, can provide more information than either method used alone. For example, when the expression of RNA encoding human trophinin and tastin was evaluated in samples of human tissues by northern blotting of poly A RNA. Low but significant levels of trophinin mRNA and tastin mRNA were observed in placenta, lung and liver while nothing was detected in heart, brain, muscle, kidney and pancreas with either probes (WO 96/10414, supra; Example V). However, immunofluorescence analysis of these tissues using anti-trophinin antibodies and anti-tastin antibodies was negative for these tissues. Thus, the combination of nucleic acid hybridization and immunofluorescence techniques together demonstrate that trophinin and tastin are not expressed by the majority of cell types in the body.

The expression of trophinin in vivo indicates that trophinin has a role in human embryo implantation. The expression of trophinin and tastin in human and other mammalian tissues was determined by immunofluorescence of tissue sections prepared and treated with anti-trophinin or anti-trophinin assisting protein antibodies as described in detail elsewhere (WO 96/10414, supra; Example VI). Immunofluorescence analysis showed the absence of trophinin in term placental tissues and in the majority of placental tissues from early (7–10 week) pregnancy. However, trophinin was readily detected in focal regions in the apical plasma membranes of syncytiotrophoblasts of chorionic villi at 7 weeks pregnancy (WO 96/10414, supra, FIG. 10A). Trophinin was also found in cytoplasmic vesicles of syncytiotrophoblasts in the chorionic villi from 7–10 week pregnancy (WO 96/10414, supra, FIG. 10B). Double immunostaining with the lamp-1 lysosome marker (Fukuda, *J. Biol. Chem.* 266:21327–21330 (1991), which is incorporated herein by reference) showed co-localization of trophinin and lamp-1 in these vesicles, indicating that trophinins are present in lysosomes or endosomes. These results indicate that trophinin expression is strictly regulated in vivo and is present on the surface of syncytiotrophoblasts at early stages of pregnancy but not at later stages of pregnancy. Trophinins that are present in lysosomes of syncytiotrophoblasts at later stages of pregnancy can be undergoing degradation following removal from the cell surface. Tastin was not detected in most of the chorionic villi from 7–10 week pregnancy, except that a weak signal was observed in the lysosomes of the syncytiotrophoblasts.

In addition to expression by the embryo, trophinin also is expressed in the uterus at the apical plasma membrane of the surface epithelium on day 16/17 endometrium (WO 96/10414, supra, FIG. 10C), but not in endometrium during the proliferation stage (day 6–13) or ovulation stage (day 14). Endometrial biopsy samples taken from the late secretory phase (day 20–28) showed staining for trophinin in the mucin. Tastin could not be detected in any of the above endometrial samples except for mucin. These results, like those for the embryo, demonstrate that trophinin expression is strictly regulated in endometrial tissue and is present for only a short time on the cell surface. The expression of trophinin is consistent with the concept of an implantation window for embryo implantation (Yoshinaga, *Biochem. Biophys. Res. Comm.* 181:1004–1009 (1988); Harper, *Ballieres Clin. Obstet. Gynaecol.* 6:351–371 (1992)).

Because of the high degree of sequence conservation between trophinin of different species, anti-trophinin antibodies are also useful to detect trophinin in tissues from other mammals. For example, antibodies to the N-terminal peptide of trophinin showed immunofluorescent staining of trophoblasts and endometrial epithelial cells at the implantation site of a Macaque monkey (WO 96/10414, supra, FIGS. 11C and 11D). Trophinin positive cells were seen among those anchoring villi and cytotrophoblasts of the blastocyst and in plaque cells or hypertrophic endometrial epithelium (not shown). The most intense staining for trophinin was observed among trophoblast and endometrial epithelial cells located at the site of adhesion between these two tissues (id.). These results with non-human primate embryos together with the studies on human and mouse endometrial and implantation site tissues provide strong support for the conservation of trophinin as a mediator of implantation among all mammals.

The level of trophinin or of a trophinin-assisting protein in a sample of endometrial tissue can be diagnostic of infertility due to failure of implantation. For example, insufficient expression of trophinin in endometrial epithelial cells or in trophoblast cells of the embryo can result in a failure of implantation. As described above, agents to detect trophinin or a trophinin-assisting protein can be used to detect the level of these proteins or can be used to detect the level of nucleic acid molecules encoding these proteins at various times during the menstrual cycle. For example, immunofluorescence staining with anti-trophinin antibodies showed that trophinin was present in mucin shed from endometrial epithelium of late secretory phases (day 20–28; WO 96/10414, supra, FIG. 10D). With implantation of the embryo, mucin shedding from the endometrial epithelium does not occur. Thus, the disclosed methods to detect trophinin are useful for testing for the absence of pregnancy since detection of trophinin shed into body fluids, for example, in cervical mucus or in serum, can provide an early indication that implantation had not occurred and therefore, that the individual was not pregnant.

The level of trophinin or a trophinin-assisting protein can also be used to diagnose the peak of fertility of a mammal. For example, the diagnosis of fertility is useful to determine the optimal time when the uterus of the mammal is most receptive for implanting a fertilized embryo. A source of body fluids or biopsy tissues is tested to determine the amount of trophinin or trophinin-assisting proteins or nucleic acids encoding such proteins that is produced by the uterus. The time point when trophinin expression or trophinin-assisting protein expression in the uterus is maximal or approaches the maximum identifies the optimal time for introduction of a fertilized embryo to maximize the chances for adherence and subsequent implantation of the embryo in the uterus.

The ability to adhere cells at their apical surfaces using the methods described in the present invention can have a significant effect on cell morphology and function as exemplified by adhesion of HT-H cells to SNG-M cells. Initial cell attachment of HT-H to SNG-M cells is associated with the extension of the microvilli from one cell to another (WO 96/10414, supra, FIGS. 2A and 2B). Within 6 hours (hr) after co-culture, each microvillus becomes flattened into the plasma membrane (WO 96/10414, supra, FIG. 2C) and adherent junctions appear after 20 hr of co-culture. Desmosomes are formed between HT-H and SNG-M cells at sites in the plasma membrane that were originally the upper (apical) surface of these cells (WO 96/10414, supra, FIG. 2D). This finding contrasts to the situation in typical epithelial cells where desmosomes normally form in plasma membranes located at the lateral or basal sides of the cell. The ability to form desmosomes at a new membrane surface can result from a sequential reorganization of the proteins that control the structure and polarity of epithelial cells.

Trophinin is expressed on the surfaces of HT-H and SNG-M cells in a unique lace-like pattern (WO 96/10414, supra, FIGS. 9A and 9B). This expression indicates that trophinin proteins cluster to form patches in the plasma membrane. Trophinin contains decapeptide repeats that form multiple β-turn structures (WO 96/10414, supra, FIG. 5A and 5B). This unique structure can be responsible for self-aggregation of trophinin in the cell membrane and for mediating cell adhesion. The subcellular localization of tastin in HT-H and SNG-M cells (WO 96/10414, supra, FIGS. 9C and 9D) indicates that tastin can associate with cytoskeletal elements such as cytokeratins present in these cells. Thus, trophinin-assisting proteins can function to segregate trophinin molecules into clusters on the apical plasma membrane by interacting with trophinin in cells.

Evidence from recent studies on cell adhesion molecules indicates that their function is regulated by association with cytoplasmic proteins and cytoskeletal structures (Gumbiner, *Neuron* 11:551–564 (1993); Stappert and Kemler, *Curr. Opin. Neurol.* 3:60–66 (1993); Garrod, *Curr. Opin. Cell Biol.* 5:30–40 (1993; Hynes, *Cell* 69:11–25 (1992)). Such molecular organization is important for cell-to-cell adhesion and cell movement. Cytoplasmic proteins involved in regulating cell adhesion molecules are associated with kinases that play a role in signal transduction, which occurs upon binding of cell adhesion molecules at the cell surface. Both trophinin and tastin contain serine and threonine residues that can serve as potential phosphorylation sites for protein kinases. For example, the amino terminal region of human trophinin contains three serine and threonine residues that are potential phosphorylation sites (FIG. 2A). The presence of phosphorylation sites in trophinin and trophinin-assisting proteins indicates that the adhesion of trophinins expressed on one cell to those on another cell can be involved in triggering phosphorylation of trophinin and trophinin-assisting proteins as a signal to initiate the morphological changes occurring subsequent to trophinin-mediated cell adhesion.

The invention provides methods to modify the ability of cells to adhere to each other. Cell adhesion can allow the cells to undergo subsequent physiological changes associated with cell adhesion. Such physiological changes can result from an increase in the adherence between cells due to increasing the level of trophinin expressed on the cell surface. An increase in adherence can be achieved by introducing an exogenous nucleic acid molecule encoding trophinin into cells and allowing the cells to adhere under appropriate conditions (WO 96/10414, supra; Example VII). This method of increasing adherence between cells can be used with any cell that can express functional trophinin proteins. Such cells include, for example, cells obtained from human or non-human primates or other mammalian cells, such as bovine, ovine, porcine or murine cells.

A nucleic acid molecule encoding trophinin can be introduced into a population of first cell types, which can be allowed to adhere to each other. In addition, a cell from the population of first cell types, which contain a nucleic acid molecule encoding trophinin, can be combined with a second cell type, wherein a DNA molecule encoding a trophinin binding protein has been introduced into the second cell type. In this case, adhesion between the first cell type and the second cell type can occur due to binding of trophinin on one cell to the trophinin binding protein of the other cell. Similarly, a third or additional cell types expressing trophinin or a trophinin binding protein can be included so as to provide adhesion among three or more cell types. As used herein, the term "trophinin binding protein" means a molecule that can bind to trophinin with an affinity of about $1 \times 10^{-5}$ M or greater as measured, for example, by ELISA. A trophinin binding protein can include, for example, trophinin itself, an anti-trophinin antibody or a trophinin-assisting protein.

Cell types that naturally express trophinin can adhere to a cell type that has been modified to express trophinin (WO 96/10414, supra; Example VII). In some cases, the expression of trophinin alone in cells may not enable cell adhesion. In such cases, adhesion may require the expression of a trophinin-assisting protein in addition to trophinin. The present invention also provides nucleic acid molecules encoding members of the trophinin-assisting protein family of proteins as well as methods for introducing such exogenous nucleic acid molecules into cells to obtain expression of a trophinin-assisting protein. This method of increasing adherence between cells by introducing an exogenous nucleic acid molecule can be used with any cell that can express functional trophinin-assisting proteins. Such cells include, for example, human and non-human primates or other mammalian cells, as described above.

The level of expression of trophinin in a cell can be increased on the cell surface by contacting the cell with a trophinin agonist. As used herein, "trophinin agonist" means a chemical or biological molecule such as a simple or complex organic molecule, a peptide, peptido-mimetic, protein, carbohydrate or nucleotide sequence that can increase the expression level of functional trophinin in a cell and, thereby, increase the capacity of the cell for trophinin-mediated cell adhesion. A nucleic acid encoding trophinin is an example of a trophinin agonist. An expression vector that contains an exogenous nucleic acid molecule encoding trophinin can also be used as a trophinin agonist. For example, the introduction of an expression vector encoding trophinin into a cell can result in increased expression of trophinin and increased ability of the cell to undergo trophinin-mediated cell adhesion. Another example of a trophinin agonist can be a trophinin-assisting protein or an expression vector that contains an exogenous nucleic acid molecule encoding a trophinin-assisting protein. For example, a cell that can express trophinin but cannot efficiently mediate cell adhesion can be due to the inability of the cell to express a level of trophinin-assisting protein sufficient to interact with trophinin or a trophinin binding protein. In such cells, a trophinin agonist can, for example, be a trophinin-assisting protein or an expression vector encoding a trophinin-assisting protein.

Particular types of trophinin agonists also can include hormones, cytokines or other types of molecules that interact directly or indirectly, for example, with genetic regulatory elements that control the expression level of trophinin or a trophinin-assisting protein. Genetic regulatory elements include, for example, promoters, enhancers, or intronic sequences that can regulate protein expression at the transcriptional or translational level. For example, a trophinin agonist can increase the expression of trophinin in a cell by binding to the promoter region of a trophinin gene and increase the efficiency of transcription. A trophinin agonist also can increase the expression of trophinin indirectly by binding to a regulatory protein, which, in turn, can activate an enhancer sequence to increase transcription of the trophinin gene.

Trophinin mediated cell adhesion also can be increased by directly contacting a cell with purified trophinin. The ability of cells to adsorb a protein such as trophinin by an active or a passive process can result in a greater level of trophinin available on the cell surface for contact with another cell, thus, increasing the likelihood of trophinin-mediated cell adhesion.

Trophinin agonists, which are useful for increasing trophinin-mediated cell adherence, are useful, for example, for preventing or minimizing the likelihood of implantation failure. Humans or other mammals that exhibit implantation failure can be tested for the level of trophinin or a trophinin-assisting protein expressed by endometrial cells using the methods described herein. Subjects having cells that fail to express sufficient levels of trophinin or trophinin-assisting proteins to achieve trophinin-mediated adhesion or express an aberrant or non-functional form of trophinin or a trophinin-assisting protein can be identified and a trophinin agonist can be used to achieve cell adhesion.

The invention also provides methods to reduce or inhibit trophinin-mediated cell adhesion by contacting a cell with a trophinin antagonist, which can reduce or inhibit trophinin binding. Such methods can be used with human or other mammalian cells that express trophinin. For example, methods to reduce or inhibit trophinin-mediated cell adhesion can be used to block or terminate embryo implantation in humans or other mammals. As used herein, "trophinin antagonist" means a chemical or biological molecule such as a simple or complex organic molecule, a peptide, peptidomimetic, protein, carbohydrate, antibody or nucleotide sequence that can reduce or inhibit the ability of trophinin to mediate cell adhesion.

A trophinin antagonist can act by binding to a trophinin molecule of a first cell and, as a result of such binding, inhibit binding to a trophinin molecule on a second cell. Thus, the binding between two trophinin molecules is reduced or inhibited by the trophinin antagonist to a level below that required for a biological activity. An antibody molecule that binds to a portion of trophinin exposed on the external side of the cell membrane is an example of a trophinin antagonist. The present invention provides methods to produce such antibodies and to evaluate such antibodies for their ability to act as trophinin antagonists in an in vitro cell binding assay (see Example I and II).

An active fragment trophinin antagonist is another example of a trophinin antagonist that can bind to trophinin on a cell and prevent the cell from binding to a second cell that expresses a trophinin binding protein. As used herein, an "active fragment trophinin antagonist" means a portion of trophinin or a trophinin binding protein that is ineffective in promoting cell adhesion but can bind to a trophinin molecule. Such active fragment trophinin antagonists can be peptides as small as about five amino acids and can be identified, for example, by screening a peptide library (see, for example, Ladner et. al., U.S. Pat. No. 5,223,409, Jun. 29, 1993, which is incorporated herein by reference) to identify peptides that bind to trophinin but do not mediate cell adhesion.

A trophinin antagonist also can interfere with the interaction of a trophinin-assisting protein with trophinin. Thus, a chemical or biological molecule such as a simple or complex organic molecule, a peptide, peptido-mimetic, protein, carbohydrate or nucleotide can be a trophinin antagonist by binding to the site on a trophinin-assisting protein or on a trophinin molecule that is involved in the interaction between a trophinin-assisting protein and trophinin.

A trophinin antagonist need not bind directly to the site in trophinin that binds to another trophinin molecule or the site in trophinin that binds to a trophinin-assisting protein, in order to inhibit cell adhesion. Thus, for example, a trophinin antagonist of sufficient size, when bound to a region in trophinin that is near the trophinin binding site can physically block another trophinin molecule from binding to the site. Also, a trophinin antagonist can bind to trophinin and change the structure of the trophinin binding site rendering it unsuitable for adhesion to another trophinin molecule. Thus, a trophinin antagonist can act like an allosteric inhibitor of an enzyme. A trophinin antagonist can also function to inhibit trophinin-mediated cell adhesion by binding to a trophinin-assisting protein in a cell, thereby inhibiting the ability of the trophinin-assisting protein to assist trophinin in mediating cell adhesion.

A trophinin antagonist also can function by reducing the level of expression of trophinin or a trophinin-assisting protein, thereby reducing or inhibiting cell adhesion. For example, nucleic acid molecules encoding an antisense nucleotide sequence or encoding a ribozyme for a trophinin or a trophinin-assisting protein can be incorporated into vectors and introduced into cells by methods well known to those in the art as described above. The level of trophinin or trophinin-assisting protein expression also can be reduced by treating cells with hormones, cytokines or other type molecules that interact directly or indirectly with genetic regulatory elements controlling the expression level of trophinin or a trophinin-assisting protein in a cell. A trophinin antagonist can effect trophinin-mediated cell adhesion by reducing the level of expression of trophinin in the cell by blocking regulatory elements involved in maintaining expression of trophinin. A trophinin antagonist can also reduce the level of trophinin expression by acting directly or indirectly as a negative regulator.

Reducing or inhibiting adhesion of cells by trophinin-mediated cell adhesion can be useful in vivo or in vitro. In vitro, trophinin antagonists can be identified and compared to each other to determine potency, which can be derived from concentration versus activity curves and can be represented as the concentration of antagonist that achieves 50% inhibition of activity. In vitro potency can be one criterion for selecting trophinin antagonists that can be useful in vivo. The in vitro method for measuring potency is based on the adhesion assay used to discover trophinin and trophinin-assisting protein molecules (WO 96/10414, supra, FIG. 1C; see, also, Example I). In this method, a radiolabeled cell line expressing trophinin and a trophinin-assisting protein (e.g. HT-H cells) is contacted with the antagonist to be tested, then the mixture is added to a paraformaldehyde fixed-monolayer of trophinin and trophinin-assisting protein expressing cells (e.g. SNG-M cells). After a period of time, the unbound cells are removed by washing and the percentage of attached cells determined by counting the bound radioactivity. A potent trophinin antagonist can be identified by its ability to significantly reduce or to inhibit trophinin-mediated cell adhesion.

The ability of trophinin to mediate cell adhesion can have other in vitro uses besides that of a trophinin antagonist. For example, trophinin can be used to bind trophinin-expressing cells to a solid support, which is useful, for example, to purify a population of trophinin expressing cells from a mixed population containing trophinin expressing and non-trophinin expressing cells or to purify a trophinin expressing embryo. Also, trophinin attached to a prosthetic device can be used to bind a layer of trophinin expressing cells to the device to render the device more suitable for introduction in vivo.

Trophinin can be bound to a solid support using methods known in the art (see, for example, Harlow and Lane, supra, 1988). For example, purified trophinin in phosphate buffered saline (PBS: 20 mM phosphate buffer, pH 7.4 and 0.15 M NaCl) can be directly adsorbed to a plastic tissue culture surface, a polyvinyl chloride surface or a nitrocellulose surface. Trophinin also can be covalently coupled to beads such as, for example, agarose or polyacrylamide that had been previously activated by a coupling agent such as glutaraldehyde or cyanogen bromide. In addition, trophinin can be attached indirectly to a solid support, for example, by first coating or coupling an agent that can specifically bind to trophinin.

A population of trophinin-expressing cells can be enriched from a mixed population of trophinin-expressing and cells that do not express trophinin by applying the mixed cell population to a solid support or surface containing trophinin. After a period of time sufficient to allow the trophinin-expressing cells to adhere to the solid support, cells that do not express trophinin can be washed from the support. The enriched population of trophinin expressing cells can be used directly on the solid support or can be removed from the solid support by vigorous washing or by treating the cells with a trophinin antagonist.

A trophinin antagonist or agonist can be used to prepare a medicament for the treatment of a condition such as infertility, for treatment of a disease or for intervening in a potential pregnancy. A trophinin vaccine can also be used to prepare a medicament to block implantation and to inhibit pregnancy. For example, a trophinin antagonist can be administered to a subject to block embryo implantation following fertilization by inhibiting binding of the embryo trophoblast cell layer to the uterine epithelial cell layer. A trophinin antagonist also can be used to terminate implantation after it has already occurred by administering a trophinin antagonist to effect detachment of the embryo from the uterine cell lining. In contrast, a trophinin agonist can be administered to a subject to alleviate implantation failure by enhancing the binding between the trophoblast cell layer of the embryo and the endothelial cell layer of the uterus. Trophinin antagonists and agonists of the invention are particularly useful when administered as a pharmaceutical composition containing the trophinin antagonist or agonist and a pharmaceutically acceptable carrier. Pharmaceutically acceptable carriers are well known in the art and include, for example, aqueous solutions such as physiologically buffered saline or other solvents or vehicles such as glycols, glycerol, oils such as olive oil or injectable organic esters.

A pharmaceutically acceptable carrier can contain physiologically acceptable compounds that act, for example, to stabilize or to increase the absorption of a trophinin antagonist or agonist. Such physiologically acceptable compounds include, for example, carbohydrates, such as glucose, sucrose or dextrans, antioxidants, such as ascorbic acid or glutathione, chelating agents, low molecular weight proteins or other stabilizers or excipients. One skilled in the art would know that the choice of a pharmaceutically acceptable carrier, including a physiologically acceptable compound, depends, for example, on the route of administration of the composition.

One skilled in the art would know that a pharmaceutical composition containing a trophinin antagonist or agonist can be administered to a subject by various routes including, for example, by intra-uterine instillation, orally or parenterally, such as intravenously, intramuscularly, subcutaneously or intraperitoneally. The composition can be administered by injection or by intubation. The pharmaceutical composition also can be incorporated, if desired, into liposomes or microspheres or can be microencapsulated in other polymer matrices (Gregoriadis, *Liposome Technology*, Vol. 1 (CRC Press, Boca Raton, Fla. 1984), which is incorporated herein by reference). Liposomes, for example, which consist of phospholipids or other lipids, are nontoxic, physiologically acceptable and metabolizable carriers that are relatively easy to make and administer.

In order to inhibit embryo implantation, the trophinin antagonist is administered in an effective dose that can effectively block a cell adhesion event. For example, in the case of implantation, an effective dose is that which blocks embryo implantation. In the case of a trophinin agonist, the "effective dose" means the amount of agonist that can effectively increase the level of trophinin-mediated cell adhesion. For example, in implantation failure, an effective dose of a trophinin agonist is the amount that allows for successful implantation. An effective amount of a trophinin antagonist or agonist in a subject can be determined using methods known to those in the art.

The total effective dose can be administered to a subject as a single administration, either as a bolus or by infusion over a relatively short period of time, or can be administered using a fractionated treatment protocol, in which the multiple treatments are administered over a more prolonged period of time. One skilled in the art would know that the concentration of trophinin antagonist or agonist required to obtain an effective dose in a subject depends on many factors including the age and general health of the subject as well as the route of administration and the number of treatments to be administered and the chemical form of the antagonist or agonist. In view of these factors, the skilled artisan would adjust the particular amount so as to obtain an effective dose for the subject being treated.

The cadherin and integrin families of adhesion molecules, which are involved in cell-cell and cell-matrix adhesion, are implicated in epithelial differentiation, carcinogenesis and metastasis. A further understanding of how such adhesion receptors exert their biological effects on the cell was accomplished through the discovery of a cell adhesion regulator gene (Pullman and Bodmer, Nature 356:529–533 (1992)). The cell adhesion regulator gene codes for a protein that is located in the cytoplasm and functions as a signal transduction molecule for integrin adhesion receptors. The cell adhesion receptor gene has the characteristics of a tumor suppressor gene because inactivation of the gene can result in loss of differentiation induction of a cell and subsequent acquisition of invasive and metastatic character. The genes encoding the trophinin-assisting proteins of the present invention also can function as tumor suppressor genes. For example, the structural features of the trophinin-assisting proteins, as derived from the deduced amino acid sequences (see SEQ ID NO: 5, SEQ ID NO: 7 and SEQ ID NO: 9), are consistent with a cytoplasmic regulatory protein that can mediate intracellular signaling of trophinin or other cell adhesion molecules.

The present invention provides methods to increase the level of expression of trophinin-assisting proteins, thus increasing the tumor suppressor activity of a cell. Such methods can, for example, be useful for the treatment of cancer. As used herein, a trophinin-assisting protein agonist means a chemical or biological molecule such as a simple or complex organic molecule, a peptide, peptido-mimetic, protein, carbohydrate or nucleotide sequence that can increase the expression level of a trophinin-assisting protein in a cell. Particular types of trophinin-assisting protein agonists can include hormones, cytokines or other types of molecules that interact either directly or indirectly with genetic regulatory elements controlling the expression level of a trophinin-assisting protein.

The following examples are intended to illustrate but not limit the present invention.

EXAMPLE I

Identification of Active Fragments of Trophinin and a Trophinin Assisting Protein (Tastin)

A. Detection of Active Fragments Based on Production of Specific Antibodies

Peptide sequences of human trophinin and tastin were analyzed to predict useful antigenic sites using the method of Hopp and Wood, Mol. Immunol. 20:483–489 (1983), which is incorporated herein by reference. A short sequence from the amino terminal end of human trophinin and from tastin were selected as antigens. The sequence Phe-Glu-Ile-Glu-Ala-Arg-Ala-Gln-Glu (SEQ ID NO: 10), representing residues 23 to 31 of human trophinin, and Asp-Gln-Glu-Asn-Gln-Asp-Pro-Arg-Arg (SEQ ID NO: 11), representing residues 41 to 49 of tastin, were chemically synthesized with a cysteine residue added to the amino terminus to facilitate protein conjugation. The peptides were conjugated to KLH using meta-maleimidobenzoyl N-hydroxysuccinimide ester (Sigma Chemical Co., St. Louis, Mo.) as described by Kitagawa and Aikawa (J. Biochem. 79:342–346 (1976), which is incorporated herein by reference).

New Zealand white rabbits were immunized with the peptide-KLH conjugates according to the following procedure. On day 1, animals were injected subcutaneously with peptide conjugate emulsified in Freund's complete adjuvant. On day 14, the animals were boosted by subcutaneous injection of peptide conjugate emulsified in Freund's incomplete adjuvant. Animals were bled (30 ml) on days 24, 31 and 38 to obtain a source of antisera. Anti-peptide antibodies were purified from rabbit antisera by protein A affinity chromatography and trophinin or tastin peptide affinity chromatography using the affinity chromatography approach described by Richardson (J. Virol. 54:186–193 (1985), which is incorporated herein by reference). Rabbit antibodies to human trophinin and tastin were used to detect these molecules in samples of cells and tissues (see WO 96/10414, supra, Example VI).

To raise antibodies specific for portions of the trophinin molecule that are expressed on the external surface of the cell membrane, the three hydrophilic domains of human trophinin containing the repeat motifs were separately expressed in bacteria as a fusion to glutathionine S-transferase (GST). The human trophinin cDNA from the aspartic acid residue at position 278 to the serine residue at position 364 was amplified by PCR using the oligonucleotide primers 5'-GGAATTCATGGATGGCTCTCCCA GCACTGGTG-3' (SEQ ID NO: 14) and 5'-GCAGCTGAGTGCTGGTGCTTAGTGTACCACC-3' (SEQ ID NO: 15) to produce the fusion protein GST551. The trophinin cDNA from the proline residue at position 441 to the serine residue at position 512 was amplified by PCR using the oligonucleotide primers 5'-GGAATT CATGCCCAGCAACAGCATTGGC-3' (SEQ ID NO: 16) and 5'-GCAGCTGAGTACTGGTGCTGGGTCCAT CACAAAAAC-3' (SEQ ID NO: 17) to produce the fusion protein GST552. The trophinin cDNA from amino acid residues serine at position 634 to asparagine at position 719 was amplified by PCR using oligonucleotide primers 5'-GGAATTCATGAGCGATGGCTTTGGCAGTAG-3' (SEQ ID NO: 12) and 5'-CGTCGACTCAGTTTGGTC CACCGCCGAAGCCAG-3' (SEQ ID NO: 13) to produce the fusion protein GST553. The trophinin cDNA from the methionine residue at position 1 to the serine residue at position 66 was amplified by PCR using the oligonucleotide primers 5'-GGAATTCATGGATATCGACTGCCTA-3' (SEQ ID NO: 18) and 5'-GCAGCTGAGTCTGGAGCT GGGTGCACCAT-3' (SEQ ID NO: 19) to produce the fusion protein GST-N-terminal trophinin.

The amplified DNA fragments of the fusion proteins were ligated into the pGEX-4T-1 vector (Pharmacia, Piscataway N.J.) at the EcoRI and XhoI sites. E. coli HB101 was transformed with the plasmid vectors and the GST fusion proteins were produced as described by the manufacturer. The fusion proteins were initially purified by affinity chromatography on glutathionine-agarose beads (Pharmacia).

For immunization to produce antibodies to the external domains of human trophinin, GST551, GST552 and GST553 fusion proteins were electrophoresed in SDS-PAGE, the gel was stained with Coomassie blue, and the band containing the fusion protein excised from the gel. The polyacrylamide gel containing the purified fusion proteins were injected into rabbits to produce antibodies according to the procedure described previously for the synthetic peptides, except that antibodies were not purified from the antisera.

Cultured human cells that express trophinin were used to evaluate the specificity of anti-trophinin antibodies by immunofluorescence analysis. HT-H and SNG-M cells which express trophinin were grown on glass coverslips in Falcon 3005 tissue culture dishes for 2–3 days as described in detail elsewhere (WO 96/10414, supra). The cells were fixed at room temperature (RT) for 15 minutes (min) with 1% paraformaldehyde in PBS, then washed 4x with PBS. Fixed cells were incubated in PBS containing 5% bovine serum albumin (IIF buffer) plus 0.1% saponin at RT for 30 min, then incubated 45 min at RT with anti-trophinin or anti-tastin antibody diluted in IIF buffer plus 0.1% saponin to permeabilize the cells. After further washing with IIF buffer plus 0.1% saponin, cells were incubated for 30 min at RT with fluorescein isothiocyanate (FITC)-conjugated goat anti rabbit IgG F(ab')$_2$ (Cappel, Durham, N.C.) diluted in IIF buffer. Coverslips containing the cells were washed 3x with IIF buffer and 1x with PBS, then placed upside down on a slide glass in an aliquot of 95% glycerol and 5% PBS. Micrographs were obtained with a Zeiss Axioplan fluorescence microscope or a Zeiss LSM410 confocal laser scanning microscope.

Antibodies to an N-terminal peptide of human trophinin (residue 23 to 31) showed staining of permeabilized HT-H and SNG-M cells that appears as a lace-like pattern due to clustering of the fluorescence over the cell surface (WO 96/10414, supra, FIGS. 9A and 9B). A tangential view by confocal microscopy showed that the majority of trophinin is detected in the upper plasma membranes of these cells. A small amount of trophinin staining is detected inside the cells and in their basal plasma membranes.

Antibody to an N-terminal peptide of tastin exhibited a diffuse staining consistent with detection of fibers in the cytoplasm of permeabilized HT-H and SNG-M cells (WO 96/10414, supra, FIGS. 9C and 9D). The fibers spread from the perinuclear region toward the edge of the cells indicating that tastin likely associates with the cytoskeleton in HT-H and SNG-M cells. Thus, tastin containing fibers that associate with the cytoskeleton can be involved in organizing trophinin as patches in the plasma membranes to effect efficient cell adhesion.

Antibodies to the hydrophilic external membrane domains GST551, GST552 and GST553 were tested for staining the cell surfaces of unpermeabilized HT-H cells. For these experiments, cells were processed as for permeabilized cells except that saponin was not used. The staining pattern observed for all three antibodies was similar to that obtained when permeabilized cells were stained by antibodies to the N-terminal domain of trophinin (residue 23 to 31, see WO 96/10414, supra, FIG. 9A). Similar results were obtained using SNG-M cells as the cell targets (WO 96/10414, supra, FIG. 9B). These results demonstrate that all three hydrophilic domains of trophinin are exposed on the cell surface of HT-H and SNG-M cells.

Staining for cell surface expresesion of trophinin was also evaluated using COS-1 cells transfected with human trophinin cDNA as described (WO 96/10414, supra; Example VI; COS-1 available under access No. CRL 1650, American Type Culture Collection, Rockville, Md.). The transfected cells showed weak and diffuse staining on the surface with all three antisera to the hydrophilic domains of trophinin. In contrast, COS-1 cells transfected with a mixture of human trophinin and tastin cDNA showed stronger and more clustered staining with the antisera. These results indicate that tastin functions to create multivalent patches of trophinin on the cell surface. Such clustering of trophinin provides a basis for the observed requirement of COS-1 cells to be transfected with cDNA encoding for trophinin and a trophinin-assisting protein in order to undergo trophinin-mediated cell adhesion.

B. Identification of Active Fragments of Trophinin that Mediate Cell Adhesion

To identify hydrophilic extracellular domains of human trophinin that mediate cell adhesion, individual domains were expressed and evaluated for specific binding to trophinin expressing cells. The trophinin extracellular domain fusion proteins GST551, GST552 and GST553, the GST-N-terminal trophinin domain (residue 1 to 66) and GST were labeled with biotin succinamide (Sigma). SNG-M, HT-H and COS-1 cells transfected with a mixture of human trophinin and tastin cDNA were grown on coverslips and processed for cell staining with the biotinylated proteins essentially as was described for the antibodies to the external domains of trophinin, except that avidin-FITC (Cappel) was used in place of a FITC-secondary antibody.

Immunofluorescence analysis showed that all three biotinylated human trophinin extracellular domain fusion proteins bound to unpermeabilized HT-H, SNG-M and the COS-1 cells transfected with trophinin and tastin cDNA. In contrast, no staining was seen when the cells were reacted with biotinylated GST or the biotinylated GST-N-terminal domain of trophinin. These results indicate that the soluble trophinin external membrane domains can bind trophinin exposed on the surface of the cells and, therefore, that such trophinin domains can be used as a trophinin vaccine and are useful to detect trophinin expressing cells.

EXAMPLE II

Identification of Trophinin Active Fragments Useful for a Trophinin Vaccine

This example provides methods to identify external membrane domains of trophinin and to identify epitopes within these domains that are useful as an anti-pregnancy vaccine.

COS-1 cells were transfected with a mixture of human trophinin and tastin cDNA in Hanks balanced salt solution (HBSS) and evaluated for cell adhesion capability. Transfected cells that were suspended in HBSS with 1 mM EDTA and maintained at RT formed distinct cell aggregates after about 10–20 min, whereas untransfected COS-1 cells formed few if any aggregates under the same conditions. The results indicate that expression of both human trophinin and tastin in COS-1 cells provided the cells with the ability to aggregate together in suspension.

The ability of various cells to adhere to a monolayer of COS-1 cells transfected with trophinin and tastin cDNA was evaluated in the adhesion cell assay in the presence of 1 mM EDTA. COS-1 cells transfected with human trophinin and tastin cDNA adhered to the monolayer, whereas COS-1 cells transfected with the control pcDNA1 vector failed to show significant binding. In contrast, when the monolayer was pretreated for 1 hr at RT with antisera to GST551, GST552 or GST553 human trophinin external domain fusion proteins, the ability of the monolayer to adhere to COS-1 cells transfected with human trophinin and tastin cDNA was greatly diminished. These results indicate that transfection with both trophinin and tastin, a trophinin-assisting protein, confers the ability to undergo cell adhesion. The inhibition of cell adhesion by antibodies to the hydrophilic external domains of trophinin confirms the role of these domains in trophinin-mediated cell adhesion and identifies candidate epitopes suitable for an anti-pregnancy vaccine.

Antibody inhibition of trophinin-mediated cell adhesion can also be evaluated using cultured cells that express trophinin. Cell adhesion assays between HT-H suspension cells and a monolayer of SNG-M cells or between SNG-M cells and a monolayer of SNG-M cells were performed as described in detail elsewhere (WO 96/10414, supra). In these assays, pretreatment of the monolayer cells with antiserum to GST553 (WO 96/10414, supra, FIG. 1D) or with Fab fragments of antibodies to GST553 significantly inhibited the amount of cell adhesion. Similar results were obtained when SNG-M cells were added to an SNG-M cell monolayer. In contrast to those results, pretreatment of the SNG-M cell monolayer with preimmune rabbit sera or with antibodies to a synthetic peptide of the amino terminal region of trophinin (residues 23 to 31) failed to inhibit adhesion of SNG-M or HT-H cells.

These results provide evidence for the role of the external hydrophilic domains of trophinin in trophinin-mediated cell adhesion and identify candidate epitopes useful for an anti-pregnancy vaccine.

EXAMPLE III

Identification of Trophinin Epitopes Defined by Anti-trophinin Antibodies

This example provides methods to identify the specific epitopes in trophinin detected by an anti-trophinin antibodies.

A. Epitope Analysis of Anti-GST553

Epitopes recognized by anti-GST553 were identified by evaluating antibody binding to a series of overlapping undecapeptides of known sequence. The peptides were synthesized and absorbed to nitrocellulose membranes using a SPOTS kit (Genosys Biotechnologies, The Woodlands, Tex.), following the manufacturer's instructions. The epitope was determined by detecting which peptides bound to anti-GST553 antibody.

Anti-GST553 detected multiple epitopes in the human trophinin; these epitopes are conserved in mouse trophinin protein (FIG. 2B). The first epitope represents the sequence Phe-Asp-Arg-Gly-Leu-Ser-Thr-Ile-Ile (SEQ ID NO: 25) present at positions 645–653 of human trophinin while the second epitope has the sequence Thr-Ile-Ile-Gly-Phe-Gly-Ser-Gly-Ser (SEQ ID NO: 26), which represents positions 651–659 of human trophinin. The three amino acid overlap, Thr-Ile-ILe, between the first and second GST553 epitopes indicates that GST553 detects two distinct 9-mer epitopes and one 15-mer epitope having the sequence Phe-Asp-Arg-Gly-Leu-Ser-Thr-Ile-Ile-Gly-Phe-Gly-Ser-Gly-Ser (SEQ ID NO: 27).

An additional GST553 epitope is nine residues in length and represents the sequence Ser-Ile-Val-Gly-Phe-Ser-Gly-Gly-Pro (SEQ ID NO: 28) located at positions 681–689 of human trophinin (FIG. 2B). All the epitopes detected by anti-GST553 in humans are localized to the third extracellular domain of human trophinin (see WO 96/10414, supra, FIG. 3).

The epitopes detected by anti-GST553 are also highly conserved in mouse trophinin. The first epitope detected by anti-GST553 in mouse trophinin represents the sequence Phe-Asn-Arg-Gly-Leu-Asn-Thr-Ile-Ile (SEQ ID NO: 29) found at positions 982 to 990. This epitope of mouse trophinin shares 78% sequence identity with the corresponding segment of human trophinin (FIG. 2B). The second crossreactive epitope detected by anti-GST553 in mouse trophinin is located at position 988 to 996 (SEQ ID NO: 26) and is identical with the corresponding segment of human trophinin (FIG. 2B). Anti-GST553 detects a nine residue epitope at mouse trophinin positions 988 to 986 (SEQ ID NO: 26) that overlaps the epitope detected at position 981 to 986, thus resulting in the 15 residue epitope Phe-Asn-Arg-Gly-Leu-Asn-Thr-Ile-Ile-Gly-Phe-Gly-Ser-Gly-Ser (SEQ ID NO: 30). Anti-GST553 also detects an epitope in mouse trophinin located at position 1018 to 1026 that is also identical in sequence with the corresponding segment of human trophinin (SEQ ID NO: 28; FIG. 2B).

B. Crossreaction of anti-GST553 Antibodies with Mouse Trophinin

Immunoblotting (western blotting) was used to demonstrate that the anti-GST553 antibodies, originally raised against the third extracellular domain of human trophinin, detected the portion of mouse trophinin containing the epitopes detected by anti-GST553. A portion of mouse trophinin representing residues 976 to 1047, which contains the epitopes recognized by anti-GST553 was expressed as a fusion protein with GST. A DNA fragment encoding mouse residues 976 to 1047 was amplified by PCR using the 5.1 kb BamHI fragment of the mouse trophinin gene subcloned into pBluescript as a template. The PCR reaction included one upstream forward primer 5'-AA GGATCCAATGGGCCTAATGCCAGCT-3' (SEQ ID NO: 31)(BamHI site underlined), and one down stream reverse primer 5'-AT<u>CTCGAG</u>TGTACTTGGTCCACCACCGA-3' (SEQ ID NO: 32)(XhoI site underlined). The amplified fragment was digested with BamHI and XhoI and ligated into BamHI and XhoI sites of pGEX-KG vector (Pharmacia).

As a control for the assay, the N-terminal portion of mouse trophinin that is located inside the cell and represents residues 1 to 50 was expressed as a fusion to GST. A DNA fragment encoding residues 1 to 50 of mouse trophinin was obtained by PCR amplification using the 1.2 kb BamHI fragment of the mouse trophinin gene that was subcloned into pBluescript vector as template. The primers used in the PCR reaction included one upstream forward primer 5'-TT <u>GGATCC</u>ACATGGATATTAACTGCCTAA-3' (SEQ ID NO: 33; BamHI site underlined) and one down stream reverse primer 5'-CCA <u>GAATTC</u>AAGCTATTTCTGGTAGTAGCT-3' (SEQ ID NO: 34)(EcoRI site underlined). The amplified fragment was digested with BamHI and EcoRI and ligated into BamHI and EcoRI sites of pGEX-3X vector (Pharmacia, Piscataway, N.J.). The vector was used to transform *E. coli* DH5α and a GST fusion protein was produced and purified by affinity chromatography using glutathione-Sepharose 4B.

The immunoblotting results demonstrated that anti-GST553 detected the GST fused to mouse trophinin residues 976 to 1047. The antibody, however, did not detect the GST fused to mouse trophinin residues 1 to 50 or the GST alone.

These results show that anti-GST553 antibodies detect essentially the same epitopes in human trophinin as in mouse trophinin. The results also demonstrate that homology in the external domains of trophinin is sufficiently high and that antibodies produced against trophinin from one species of mammal can identify the external domain of trophinin from a different species of mammal.

EXAMPLE IV

Inhibition of Pregnancy using Anti-trophinin Antibodies

This example demonstrates the usefulness of anti-trophinin antibodies to inhibit embryo implantation.

A. Detection of Trophinin Protein Expression in Mouse Adult and Fetal Tissue

CD-1 mice were intercrossed to provide sources of fertilized egg and female reproductive organs, including ovary, oviduct, and uterus representing various stages of early pregnancy to be evaluated for expression of mouse trophinin. Tissues collected on days 2 to 5 of pregnancy (day 0.5=vaginal plug) were immersion-fixed in freshly prepared 1% paraformaldehyde/PBS, pH 7.4, at 4° C. overnight, dehydrated, embedded in paraffin, and serially sectioned at 5 µM thickness. Tissue samples from infant mice were collected and processed in the same manner. The deparaffinized tissue sections were subjected to antigen retrieval treatment based on microwave heating (Shi et al., *J. Histochem. Cytochem.* 39:741 (1991), which is incorporated herein by reference). The slides of every tenth section were stained with hematoxylin and eosin and examined under a microscope to identify sections containing eggs or blastocysts. Tissue sections adjacent to the identified sections were stained with anti-trophinin antibodies followed by FITC-conjugated goat anti-rabbit IgG (Cappel, Durham, N.C.) and were examined under a Zeiss Axioplan fluorescence microscope. Controls not treated with the first antibodies were taken in each immunostaining experiment.

For immunostaining of the outer surface of pre-implanted mouse blastocysts, blastocysts were collected from the uterus of C57BL/6 mice on day 3.5 of pregnancy. After removal of the zona pellucida by acidic Tyrode's solution (Sigma, St. Louis, Mo.), the blastocysts were fixed using 1% paraformaldehyde/PBS at RT for 15 min and washed with PBS. For the detection of trophinin, fixed embryos were subjected to immunostaining in glass cavity blocks using the above described antibodies. For detection of sialic acids, fixed embryos were stained using the monoclonal antibody specific to NeuAcα2-3Galβ1-4GlcNAc structure, which was produced and characterized as described by Suzuki et al. (*J. Biochem.* (Japan) 109:354–360 (1991), which is incorporated herein by reference) and FITC-conjugated goat anti-mouse IgM (Cappel). The embryos were mounted on glass slides and examined under a Zeiss fluorescence microscope.

The anti-GST553 antibody staining results showed that mouse trophinin was not expressed in female reproductive organs prior to day 3 of pregnancy. Both unfertilized eggs in the ovary and fertilized eggs at 8-cell stage in the oviduct failed to express trophinin. Trophinin positive cells were detected by anti-GST553 staining in mouse embryos and in the surface epithelium of the mouse endometrium on day 3.5 of pregnancy, the stage characterized by morula entry into the uterus. On day 4.5 of pregnancy, when the blastocysts were hatched and implanted in the uterus, mouse trophinin expression was increased over day 3.5 in blastocysts and the luminal epithelia of the uterus. On day 5 of pregnancy, when embryos were fully surrounded by the endometrial stroma, trophinin staining was no longer detectable in the uterus or the embryo. Trophinin expression detected by anti-GST553 immunostaining was not detectable in adult mouse brain, stomach, kidney, thymus, or intestine. These results indicate that mouse trophinin expression in female pregnant mice parallels expression in humans and that the trophinin gene plays a critical role during early implantation in mammals.

B. Inhibition of Pregnancy with Anti-Trophinin Antibody Fab Fragments

Anti-GST553 antibody raised to the third extramembrane domain of human trophinin was tested for immunostaining of unpermeabilized blastocysts to verify that the epitopes detected in mouse trophinin by the antibodies were accessible on the external side of the cell. Anti-GST553 showed strong staining at the apical plasma membranes of the trophoectoderm cells of a Rhesus monkey blastocyst that had been treated to remove the exterior zona pellucida. More intense staining for trophinin was observed on trophoblast cells located at the embryonic pole as opposed to the mural pole (WO 96/10414, supra, FIGS. 11A and 11B). Such polarized staining is consistent with the observation that the embryonic pole of both primate and human blastocysts is the site of attachment to the endometrial epithelium (Enders et al., *Cell. Molec. Aspects Implant.* (S. R. Glasser and D. W. Bullock eds.) pp.365–382 (1981); Knoth and Larson, *Acta. Obstet. Gynecol. Scand.* 51:385 (1972); Lindenberg et al., *Hum. Reprod. Fertil.* 83:149 (1986)). Anti-GST553 also binds to the surface of mouse embryos, but the polarity of immunostaining observed with the monkey embryo is not observed for the mouse embryo.

Inhibition of pregnancy was evaluated using univalent Fab fragments. The Fab fragment of anti-GST553 was prepared by papain digestion. Papain (Calbiochem-Behring; La Jolla Calif.) was dissolved at 1–2 mg/ml in 0.1 M Tris-HCl, pH 8.0, containing 2 mM EDTA and 1 mM dithiothreitol, and incubated at 37° C. for 15 min. One one-hundredth volume of the papain solution was added to about 5 mg/ml of the anti-GST553 antibodies (IgG fraction) in the same buffer and incubated at 37° C. for 1 hr. The digestion was terminated by the addition of 20 mM iodoacetamide. The mixture was then incubated on ice and in the dark for 1 hr, dialyzed overnight at 4° C. against sterilized PBS, and passed through a 0.2 mm filter. The complete digestion of IgG, which should produce the Fab and Fc fragments, was confirmed by SDS-PAGE. As a control, the preimmune IgG fraction, isolated from serum from the same rabbit later immunized with GST553, was also processed to generate Fab fragments.

Blastocysts were obtained from Female C57BL/6 mice that had been injected with human chorionic gonadotropin to induce superovulation, then mated with fertile males. On day 3.5 of pregnancy, blastocysts were collected from the uterine horn by flushing with M2 culture medium as described in detail elsewhere (Hogan et al., *Manipulating the Mouse Embryo. A Laboratory Manual* 2nd Ed., Cold Spring harbor Lab. Press, New York, N.Y., (1994), which is incorporated herein by reference; see p.497). Blastocysts were washed with M2 medium to remove contaminating materials such as red blood cells and epithelial cells and then examined under a binocular microscope (Model SMZ-10A, Nikon).

Blastocysts that were morphologically normal and unhatched were selected from the remainder and divided into several groups for further experimentation. One group containing 13–16 blastocysts was transferred using glass capillary tubes to a solution containing anti-GST553 Fab antibody solution to yield a 25 ml volume with an antibody concentration of 1.3 mg/ml. The embryo-antibody mixture was placed as a 25 ml droplet in a 32 mm plastic petri dish (Falcon No. 1008, Becton Dickinson, Lincoln Park, N.J.), then incubated in the dark at 33° C. for 15 min. Changes in pH, temperature, and exposure to light were minimized to avoid damaging the blastocysts during the antibody incubation process. The second group of blastocysts was treated with preimmune Fab immunoglobulin at 1.3 mg/ml and the third group treated with dialyzed mouse ascitic fluid containing monoclonal antibody NS24. Groups 2 and 3 were processed in the same manner as the anti-GST553 Fab group. Pseudopregnant CD-1 female mice on day 2.5 of their pseudopregnancy were implanted with the treated blastocysts as described by Hogan et al. (supra) by injecting the embryo-antibody mixture (total volume, less than 10 µl) into both horns of the uterus. The implanted embryos were allowed to develop to term. On parturition day, the pups were counted and the reproductive organs were collected from the recipient mice. These organ samples were fixed, embedded in paraffin, sectioned, the sections stained with hematoxylin and eosin and evaluated by light microscopy.

No pups were born from the female mice who were implanted with blastocysts treated with Fab anti-GST553 antibody (Table 1).

TABLE 1

|  | Antibody (mg/ml) | Blastocysts transferred | Pups born | Percent mothers pregnant |
|---|---|---|---|---|
| Anti-GST553 | 1.3* | 16 | 0 | 0 |
|  | 1.3 | 13 | 0 | 0 |
| Pre-immune | 1.3 | 13 | 7 | 54 |
| IgG | 1.3 | 11 | 7 | 64 |
| NS24 antibody | 0.47 | 16 | 13 | 81 |
|  | 4.7 | 13 | 8 | 62 |

*Each line represents an experiment. The % mothers pregnant was about 65% for untreated Blastocysts.

Histological evaluation of the uterus from mothers treated with anti-GST553 showed no evidence of decidual cell reaction, one of the earliest responses of the endometrium to implanting embryo (Whyte, Biol. Trophoblast (Loke and Whyte eds.) Elsevier Sci. Pub., Amsterdam p.513 (1983)) or any evidence of necrosis or acute cell injury was detected. These observations indicate that treatment of the blastocysts with Fab anti-GST553 antibody effectively blocked implantation in the uterus. The absence of uterine toxicity in the anti-trophinin treated animals is consistent with the observation that cultured human trophoblastic HT-H cells, which express trophinin on their cell surface, show no evidence of toxicity after incubation with Fab anti-GST553 antibody for 72 hours in culture. HT-H cells were grown as a monolayer in a 3.5 cm tissue culture dish, and were overlayed with whole antibody (protein A purified IgG fraction) at 1 mg/ml concentration, and heated for one hour. Then DME medium was added to the cells and continued in culture for seven days. Cells were examined under a microscope every day for their growth and morphology.

Blastocysts treated with the Fab fragments prepared from the preimmune immunoglobulin showed an efficiency of pregnancy comparable to that obtained from the no pretreatment group or the control group treated with monoclonal antibody NS24, specific to NeuAca2-3Galb1-4GlcNAc (Table 1).

The embryo implantation experiments indicate that Fab fragments of anti-trophinin antibody that binds to an extramembrane domain of trophinin accessible on the outer surface of blastocysts effectively blocked embryo implantation in vivo. The ability of anti-trophinin antibody to block implantation was mediated through the specificity of the antibody binding site because pretreatment of blastocysts with the pre-immune IgG fraction or the monoclonal antibody NS24 to sialic acid had no discernable effect on implantation (Table 1). The inhibition of implantation by anti-GST553 was not due to simple coating of the surface with antibody because the NS24 antibody, like anti-GST553, showed strong staining of the apical surfaces of nonpermeabilized mouse blastocysts taken on day 3.5 of pregnancy. However, unlike the anti-GST553 antibody, the NS24 antibody could not block cell adhesion between human HT-H and SNG-M cells despite the ability of NS24 to bind to the surfaces of these cells.

These results demonstrate that trophinin is involved in the initial adhesive step of embryo implantation and that antibodies to trophinin can effectively inhibit embryo implantation and prevent pregnancy.

EXAMPLE V

Isolation and Characterization of the Mammalian Trophinin Gene

This example provides methods to isolate, characterize and detect the trophinin gene in genomic DNA.

A. Cloning the Mouse trophinin Gene

A genomic mouse library representing the 129/SvJ strain was constructed in the lambda FIX II vector (Stratagene, San Diego, Calif.), plated on E. coli XL-1-Blue MRX host cells and screened by plaque hybridization using the 2.5 kb human trophinin cDNA (SEQ ID NO:1) as a probe. Phage lifts were prepared with Magna NT nylon filters (Micron Separations, Westboro, MA). The cDNA was labeled with [$\alpha$-$^{32}$P]dCTP using the Prime-It II kit (Stratagene; San Diego Calif.). Filters were prehybridized at 35° C. for 5 hr in 6×SSPE (0.62 M NaCl, 0.06 M $NaH_2PO_4$•$H_2O$, 0.075 M EDTA, pH 7.4) containing 50% formamide, 5×Denhardt's solution, 0.1% SDS, and 200 mg/ml denatured salmon sperm DNA), then hybridized in the same solution containing [$^{32}$P]-labeled cDNA probe at 35° C. for 20 hr. The filters were washed at 35° C. for 10 min, three times, in 6×SSPE containing 0.1% SDS and subjected to autoradiography. After two rounds of screening a positive clone was isolated that hybridized to the trophinin cDNA probe.

DNA was purified from the positive clone, digested with BamHI and then subjected to Southern blotting using the [$^{32}$P]-labeled human trophinin cDNA as a probe. Two hybridization-positive fragments (5.1 kb and 1.2 kb) were detected in the blot and the corresponding fragment was isolated from the gel and subcloned into the pBluescript II KS (+) plasmid (Stratagene).

Nucleotide sequences of the subcloned mouse DNA fragments were determined using an ABI PRISM Dye Terminator Cycle Sequencing kit (Perkin Elmer; Foster City Calif.) and an Applied Biosystem 373 DNA sequencer (Perkin Elmer; Norwalk Conn.). Editing and analysis of DNA sequences were carried out by the DNASIS program (Hitachi Software Engineering, Japan). To search for homologous amino acid sequences, databases were screened by the BLAST network program (National Center for Biotechnology Information, NIH, Bethesda, Md.; Altschul et al., J. Mol. Biol. 215:403–410, (1990)), using default parameters. Alignments of amino acid sequences were undertaken with the Clustal W network program (European Molecular Biology Laboratory, Heidelberg, Germany; Thompson et al., Nucleic Acids Res. 22:4673 (1994), which is incorporated herein by reference).

B. Copy Determination of the Trophinin Gene

Southern blot analysis of mouse genomic DNA was performed to estimate whether the mouse trophinin gene is present in the genome as a single copy or as multiple copies. Southern blotting was performed as detailed elsewhere (Ausubel et al., Curr. Prot. Mol. Biol. John Wiley and Sons (1994), which is incorporated herein by reference; see sections 2.05–2.14.8). Briefly, genomic DNA was extracted from mouse liver using 10 mM Tris-HCl buffer, pH 7.5, containing 0.15 M NaCl, 10 mM EDTA, and 0.1% SDS. The extract was mixed with Proteinase K at 0.5 mg/ml of enzyme(Boehringer Mannheim, Indianapolis, Ind.), and incubated at 42° C. for 16 hr.

Genomic DNA was purified by phenol-chloroform extraction followed by ethanol precipitation. After purification, the DNA was digested with restriction enzymes, electrophoresed in a 0.7% agarose gel, and transferred onto a NYTRAN PLUS™ membrane (Schleicher & Schuell, Keene, N.H.) under alkaline conditions (0.1 M NaOH, 0.1 M NaCl). DNA was fixed to the membrane by exposure to ultraviolet light (1200 microjoules) using the "STRATALINKER" (Stratagene). The blot was prehybridized at 37° C. for 5 hr in 6×SSPE containing 50% formamide, 5×Denhardt's solution, 0.1% SDS, and 200 mg/ml denatured salmon sperm DNA and hybridized in the same solution containing a [32P]-labeled mouse trophinin genomic DNA BamHI fragment (about 5 kb and including the coding region of mouse trophinin), at 37° C. for 20 hr. The membrane was washed at 37° C. in 6×SSPE containing 0.1% SDS, then washed to a high stringency (0.1×SSPE, 0.1% SDS, 50° C.), and exposed to X-ray film at −80° C. with an intensifying screen for about 72 hr.

The Southern blot results showed detection of only a single band when various restriction enzymes were used, indicating that the mouse genome contains only a single copy of the trophinin gene. Southern blotting was also performed on human placenta DNA and probed with the full length 2.5 kb human trophinin cDNA. The human blots also revealed detection of only a single restriction fragment indicating that the human trophinin gene, like the mouse trophinin gene, is present in the human genome in a single copy.

C. Chromosomal Mapping of the Trophinin Gene

Chromosomal mapping of the mouse trophinin gene was determined using interspecific backcross progeny derived from (C57BL/6J×*M. spretus*) $F_1$ females (i.e., $N_2$ mice) and C57BL/6J males as described in detail elsewhere (Copeland et al., *Trends Genet*. 7:113–118 (1991) which is incorporated herein by reference). This interspecific backcross mapping panel has been typed for over 2000 loci that are well distributed among autosomes as well as the X chromosome (id.). The trophinin gene locus, designated Tnn, was mapped by analysis of 205 $N_2$ mice. DNA isolation, restriction enzyme digestion, agarose gel electrophoresis, Southern blot transfer, and hybridization were performed essentially as described in detail elsewhere (Jenkins et al., *J. Virol*. 43:26–36 (1982), which is incorporated herein by reference). The Southern transfer was performed with Hybond-N⁺ nylon membranes (Amersham; Arlington Heights Ill.) and the fragments probed using the 5.1 kb BamHI fragment of mouse genomic DNA, labeled with [α-$^{32}$P] dCTP using a nick translation labeling kit (Boehringer Mannheim; Indianapolis Ind.). The membranes were washed to a final stringency of 1.0×SSC, 0.1% SDS, 65° C. A fragment of 10.5 kb was detected in HincII digested C57BL/6J DNA, and a fragment of 6.3 kb was detected in HincII digested *M. spretus* DNA. The presence or absence of the 6.3 kb HincII *M. spretus*-specific fragment was followed in backcross mice.

A description of the probes and RFLPs for the loci linked to Tnn, including Bruton's agammaglobulinemia tyrosine kinase (Btk) and myelin proteolipid protein (Plp) are described in detail elsewhere (Rawlings et al., *Science* 261:358–361 (1993), which is incorporated herein by reference). Recombination distances were calculated as described elsewhere (Green, in *Genetics and Probability in Animal Breeding Experiments*, Oxford University Press, p77–113 (1981), which is incorporated herein by reference) using the computer program SPRETUS MADNESS. Gene order was determined by minimizing the number of recombination events required to explain the allele distribution patterns.

The backcross panel and parent species DNA were digested with several enzymes and analyzed by Southern blot hybridization for informative restriction fragment length polymorphisms (RFLPs) using a mouse genomic DNA probe. The 6.3 kb HincII *M. spretus* RFLP was used to follow the segregation of the Tnn locus in backcross mice. The mapping results indicated that the mouse Tnn locus is located on the distal region of the mouse X chromosome linked to Btk and Plp loci. Eighty-eight mice were typed for Btk, Plp and Tnn loci and each locus was analyzed in pairwise combinations with a second locus using recombination frequencies provided by the original group of mice as well as additional mice tested on either Btk or Plp loci. The ratios of the total number of mice exhibiting recombinant chromosomes to the total number of mice analyzed for each pair of loci and the most likely gene order are: centromere-Btk-3/92-Plp-7/89-Tnn. The recombination frequencies (expressed as genetic distances in centimorgans (± the standard error) are -Btk-3.3+/−1.9-Plp-7.9+/−2.9-Tnn.

The interspecific map of the X chromosome as defined by Btk, Plp and Tnn compared with a composite mouse linkage map that reports the map location of many uncloned mouse mutations (Mouse Genome Database, The Jackson Laboratory, Bar Harbor, Me.) indicates that Tnn maps to a region of the composite map that lacks mouse mutations.

The distal region of the mouse X chromosome, which carries the Tnn gene, is homologous to both the long and short arms of the human X chromosome. In particular, the region just proximal of the pseudoautosomal segment in the mouse X chromosome is homologous to the short arm of the human X chromosome Hofmann and Stoffel, supra, 1993). Analysis of human chromosomes by fluorescent in situ hybridization (FISH) using the human trophinin cDNA probe showed that the Tnn locus is located on the short arm of the human X chromosome. Tnn probably maps to the Xp locus in the short arm of the human X chromosome as the Xp locus is homologous to a region near where Tnn maps in the mouse X chromosome.

The results in this Example demonstrate that the methods disclosed are useful to isolate, characterize and detect the trophinin gene in genomic DNA and that the trophinin gene is contained as a single copy on the X chromosome of both humans and mice.

Although the invention has been described with reference to the examples provided above, it should be understood that various modifications can be made without departing from the spirit of the invention. Accordingly, the invention is limited only by the claims.

I claim:

1. A substantially purified nucleic acid molecule, comprising a nucleotide sequence encoding the mouse trophinin amino acid sequence shown as SEQ ID NO: 24.

2. A vector, comprising the nucleic acid molecule of claim 1.

3. A host cell, containing the vector of claim 2.

4. The nucleic acid molecule of claim 1, wherein the nucleotide sequence is SEQ ID NO:23 from mouse.

5. A vector, comprising the nucleic acid molecule of claim 4.

6. A host cell, containing the vector of claim 5.

7. A substantially purified nucleic acid molecule, comprising a nucleotide sequence that hybridizes under high stringency conditions to the nucleotide sequence of claim 4, or a complementary sequence thereof, provided the nucleic acid molecule does not hybridize under high stringency conditions to mRNA from COS-1 cells or to mRNA encoding human trophinin (SEQ ID NO:2); and wherein the high stringency conditions comprise washing with 0.1×SSPE, 0.1% SDS at 50° C.

8. A probe, comprising the nucleic acid molecule of claim 7 and a detectable label.

9. A substantially purified nucleic acid molecule encoding an active fragment of mammalian trophinin, comprising residues 972 to 1053 shown in FIG. 2B (SEQ ID NO:37).

10. A vector, comprising the nucleic acid molecule of claim 9.

11. A host cell, containing the vector of claim 10.

12. A substantially purified nucleic acid molecule, comprising a nucleotide sequence that hybridizes under high stringency conditions to the nucleotide sequence of claim 9, or a complementary sequence thereof, wherein the high stringency conditions comprise washing with 0.1×SSPE, 0.1% SDS at 50° C.

13. A probe, comprising the nucleic acid molecule of claim 12 and a detectable label.

14. A substantially purified nucleic acid molecule encoding an active fragment of mammalian trophinin, comprising an amino acid sequence selected from the group consisting of Phe-Asn-Arg-Gly-Leu-Asn-Thr-Ile-Ile (SEQ ID NO:29)

and Phe-Asn-Arg-Gly-Leu-Asn-Thr-Ile-Ile-Gly-Phe-Gly-Ser-Gly-Ser (SEQ ID NO:30).

15. A vector, comprising the nucleic acid molecule of claim 14.

16. A host cell, containing the vector of claim 15.

17. A substantially purified nucleic acid molecule, comprising a nucleotide sequence that hybridizes under high stringency conditions to the nucleotide sequence of claim 14, or a complementary sequence thereof, wherein the high stringency conditions comprise washing with 0.1×SSPE, 0.1% SDS at 50° C.

18. A probe, comprising the nucleic acid molecule of claim 17 and a detectable label.

* * * * *

UNITED STATES PATENT AND TRADEMARK OFFICE
CERTIFICATE OF CORRECTION

PATENT NO.    : 6,111,089
DATED         : August 29, 2000
INVENTOR(S)   : Fukuda It is certified that error appears in the above-identified patent and that said Letters Patent is hereby corrected as shown below:

Column 16,
Line 52, please delete "ill in" and replace with -- III in --.
Line 60, please delete "lastin" and replace with -- tastin --.

Signed and Sealed this

Ninth Day of September, 2003

JAMES E. ROGAN
*Director of the United States Patent and Trademark Office*